United States Patent
Xu et al.

(10) Patent No.: US 11,466,034 B2
(45) Date of Patent: Oct. 11, 2022

(54) COMPOUND FUNCTIONING AS BROMODOMAIN PROTEIN INHIBITOR, AND COMPOSITION

(71) Applicant: Betta Pharmaceuticals Co., Ltd., Zhejiang (CN)

(72) Inventors: Yan Xu, Beijing (CN); Xiaofeng Xu, Beijing (CN); Jiabing Wang, Beijing (CN); Lieming Ding, Zhejiang (CN)

(73) Assignee: Betta Pharmaceuticals Co., Ltd., Zhejiang (CN)

( * ) Notice: Subject to any disclaimer, the term of this patent is extended or adjusted under 35 U.S.C. 154(b) by 0 days.

(21) Appl. No.: 16/954,901

(22) PCT Filed: Dec. 20, 2018

(86) PCT No.: PCT/CN2018/122211
§ 371 (c)(1),
(2) Date: Jun. 17, 2020

(87) PCT Pub. No.: WO2019/120234
PCT Pub. Date: Jun. 27, 2019

(65) Prior Publication Data
US 2020/0385408 A1   Dec. 10, 2020

(30) Foreign Application Priority Data
Dec. 20, 2017   (WO) .............. PCT/CN2017/117451

(51) Int. Cl.
*C07D 519/00*   (2006.01)
*C07D 471/06*   (2006.01)

(52) U.S. Cl.
CPC ......... *C07D 519/00* (2013.01); *C07D 471/06* (2013.01); *C07B 2200/13* (2013.01)

(58) Field of Classification Search
CPC ........................... C07D 519/00; C07D 471/04
USPC ........................................................ 514/250
See application file for complete search history.

(56) References Cited

U.S. PATENT DOCUMENTS

2015/0148342 A1   5/2015   Yue et al.

FOREIGN PATENT DOCUMENTS

| CN | 105324379 A | 2/2016 | |
|---|---|---|---|
| CN | 105611835 A | 5/2016 | |
| CN | 107108614 A | 8/2017 | |
| CN | 107207493 A | 9/2017 | |
| CN | 105102453 B | 4/2018 | |
| CN | 106414442 B | 3/2019 | |
| CN | 105407888 B | 5/2019 | |
| EA | 028175 B1 | 10/2017 | |
| WO | 2014182929 A1 | 11/2014 | |
| WO | 2015081189 A1 | 6/2015 | |
| WO | 2015081203 A1 | 6/2015 | |
| WO | 2015164480 A1 | 10/2015 | |
| WO | WO-2015164480 A1 * | 10/2015 | .............. A61P 31/22 |
| WO | 2016077378 A1 | 5/2016 | |
| WO | 2016077380 A1 | 5/2016 | |

OTHER PUBLICATIONS

Taiwan Patent Office, First Office Action, dated Oct. 1, 2019, 6 pages.
Extended European Search Report for European Application No. 18891050.9 dated Nov. 3, 2020; 7 pgs.
Russia Patent Office, First Office Action, International Application No. 2020123254, dated Jun. 8, 2022, 17 pages.
China Patent Office, First Office Action, International Application No. 201880081489.6, dated Aug. 2, 2022, 9 pages.

* cited by examiner

*Primary Examiner* — Kahsay Habte
(74) *Attorney, Agent, or Firm* — Umberg Zipser LLP; Jason Tejani

(57) ABSTRACT

The invention relates to a bromodomain inhibitor. The invention also provides compositions and formulations comprising such compounds, and methods of using and preparing such compounds.

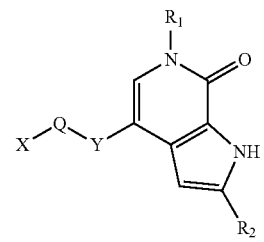

Formula (I)

22 Claims, 2 Drawing Sheets

COMPOUND FUNCTIONING AS BROMODOMAIN PROTEIN INHIBITOR, AND COMPOSITION

FIELD OF THE INVENTION

The present invention relates to compounds inhibiting or otherwise modulating the activity of bromodomain-containing proteins, compositions and formulations comprising such compounds, and methods of using and preparing such compounds.

BACKGROUND OF THE INVENTION

Bromodomain (BRD) proteins containing BET (bromodomain and extra-terminal domain) family include four types: BRD2, BRD3, BRD4, and BRDT. Proteins of BET family are epigenetic coded readers that acetylate lysine residues on histones to alter chromatin structure and gene expression. BRD2, BRD3 and BRD4 are universally expressed, while BRDT is restricted to germ cells. BET protein plays a necessary but non-overlapping role in regulating gene transcription and controlling cell growth. BET proteins are associated with large protein complexes that regulate the transcription of many genes, including RNA polymerase II (Pol II) and forward transcription elongation factor (P-TEFb). It has been confirmed that BRD2 and BRD4 proteins maintain binding to chromosomes during mitosis and are required to promote transcription of important genes (including cyclin D and c-Myc) that initiate the cell cycle (Mochizuki, J Biol. Chem. 2008 283: 9040-9048). BRD4 protein is combined with RNA polymerase II (Pol II) and positive transcription elongation factor (P-TEFb) to jointly promote the transcription and expression of many genes related to cancer cell proliferation and apoptosis, such as c-Myc, cyclin, anti apoptosis protein Bcl-2, and regulate the growth and proliferation of tumor cells (Jang et al., Mol. Cell 2005 19:523-534). In some situations, the kinase activity of BRD4 can directly phosphorylate and activate RNA polymerase II (Devaiah et al., PNAS 2012 109: 6927-6932). Cells lacking BRD4 show impaired cell cycle progression. BRD2 and BRD3 have been reported to be associated with histones and actively transcribed genes and can be involved in promoting transcription elongation (Leroy et al., Mol. Cell. 2008 30: 51-60). In addition to acetylated histones, BET proteins have been shown to selectively bind acetylated transcription factors, including the RelA subunit of NF-kB and GATA1, thereby directly regulating the transcriptional activity of these proteins to control the expression of genes involved in inflammation and hematopoietic differentiation (Huang et al., Mol. Cell Biol. 2009 29: 1375-1387; Lamonica Proc. Nat. Acad. Sci. 2011 108: E159-168).

BET proteins including BRD4 have been identified as important mediators that alter gene expression characteristics found in a number of diseases including cancer, diabetes, obesity, atherosclerosis, cardiovascular, renal disease and viral infections. Read for reference Muller, S., et al., Expert Rev. Mol. Med., 13: e29 (2011); Zhou, M., et al., J. Virol., 83: 1036-1044 (2009); Chung, C W, et al., J. Med. Chem., 54: 3827-3838 (2011). For example, Myc is involved in most human cancers, and BET protein has been identified as a regulator of c-Myc; inhibition of BET protein (including BRD4) has been shown to down-regulate Myc transcription.

Therefore, there is a great need to develop compounds for use as bromodomain inhibitors. In particular, the development of compounds for use as BET inhibitors will be highly anticipated. Although it has been reported that some small molecule BET inhibitors have been used in clinical research, there are currently no drugs approved for marketing. Therefore, still need to develop new small molecule BET inhibitors for the clinical treatment of BET-mediated diseases or illness offers a new medication option.

SUMMARY OF INVENTION

The present invention relates to compounds as bromodomain inhibitors, especially BRD4 inhibitors, and their use in the treatment of BET-mediated diseases. The present invention first provides a compound shown in formula (I) or a pharmaceutically acceptable salt thereof,

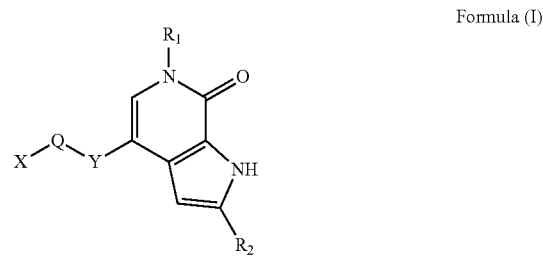

Formula (I)

Wherein, $R_1$ and $R_2$ are each independently selected from H, $C_{1-6}$ alkyl, $C_{1-6}$ alkoxy, $C_{6-10}$ aryl or $C_{5-10}$ heteroaryl, the $C_{1-6}$ alkyl, $C_{1-6}$ alkoxy, $C_{6-10}$ aryl or $C_{5-10}$ heteroaryl is optionally substituted by $C_{1-6}$ alkyl, —$NH_2$, —OH, $C_{6-10}$ aryl or $C_{5-10}$ heteroaryl; the $C_{5-10}$ heteroaryl has 1, 2, or 3 heteroatoms independently selected from nitrogen, oxygen or sulfur;

Q is absent or selected from $C_{1-6}$ alkylene, —$SO_2$— or —NH—, the $C_{1-6}$ alkylene or —NH— isoptionally substituted by halogen, $C_{1-6}$ alkyl or $C_{1-6}$ alkoxy;

X is selected from H, $C_{1-6}$ alkyl, $C_{6-10}$ aryl or $C_{5-10}$ heteroaryl, the $C_{1-6}$ alkyl, $C_{6-10}$ aryl or $C_{5-10}$ heteroaryl is optionally substituted by halogen, halo $C_{1-6}$ alkyl, $C_{1-6}$ alkyl, $C_{1-6}$ alkoxy, $C_{1-6}$ alkylthio, $C_{1-6}$ alkoxycarbonyl or $C_{1-6}$ alkyl-$SO_2$—;

Y is

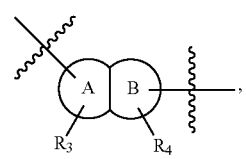

wherein ring A is a 5 or 6 membered ring containing 0, 1, 2 or 3 heteroatoms independently selected from N, O or S; ring B is phenyl or $C_{5-6}$ heteroaryl containing 0, 1, 2 or 3 heteroatoms each independently selected from N, O or S.

$R_3$ and $R_4$ are absent or are each independently selected from H, halogen, hydroxyl, amino, $C_{1-6}$ alkyl, $C_{1-6}$ alkoxy, cyano, oxo, or —$N(R_5)$—$SO_2$—$R_6$;

$R_5$ and $R_6$ are each independently selected from H, $C_{1-6}$ alkyl or $C_{1-6}$ halogenoalkyl.

As for the compounds shown in formula (I), the invention further provides some preferred technical schemes.

In some embodiments, $R_1$ is selected from H, $C_{1-4}$ alkyl, phenyl or $C_{5-6}$ heteroaryl, the $C_{1-4}$ alkyl, phenyl or $C_{5-6}$ heteroaryl is optionally substituted by $C_{1-6}$ alkyl, —$NH_2$, phenyl, or $C_{5-6}$ heteroaryl; preferably, the heteroaryl has 1, 2, or 3 heteroatoms independently selected from nitrogen or sulfur.

In some embodiments, $R_1$ is H, —$CH_3$,

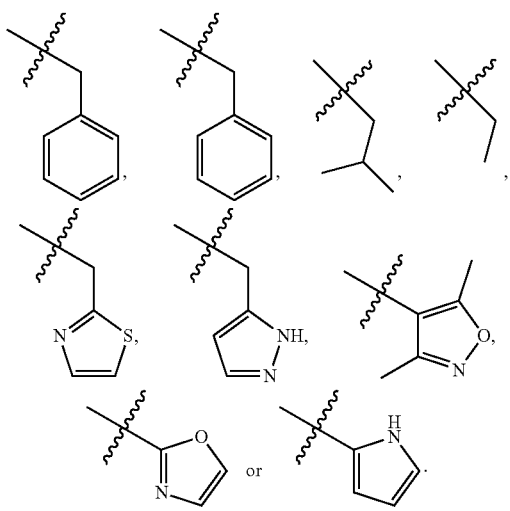

or

.

In some embodiments, $R_1$ is H, —$CH_3$,

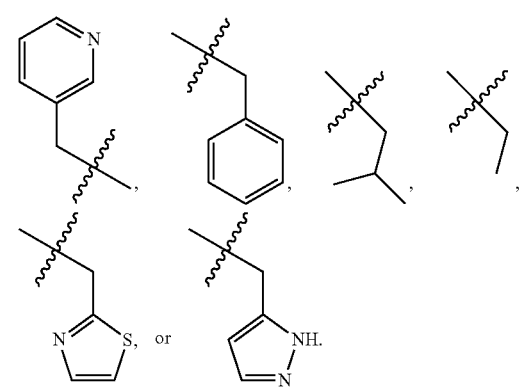

, or

.

In some embodiments, $R_2$ is H or $C_{1-3}$ alkyl.
In some embodiments, $R_2$ is H or —$CH_3$.
In some embodiments, Q is absent or is selected from —$CH_2$—,

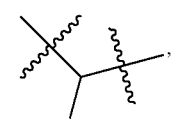 [SMILES: *C(*)C]

,

—NH— or —$SO_2$—.

In some embodiments, X is selected from H, $C_{1-3}$ alkyl or phenyl, the phenyl is unsubstituted or optionally substituted by halogen, halo $C_{1-3}$ alkyl, $C_{1-3}$ alkyl, $C_{1-3}$ alkoxy, $C_{1-3}$ alkylthio, $C_{1-3}$ alkoxycarbonyl, or $C_{1-3}$ alkyl-$SO_2$—.

In some embodiments, X is selected from H, $C_{1-3}$ alkyl or phenyl, the phenyl is unsubstituted or optionally substituted by F, Cl, methyl, trifluoromethyl, methoxy, methylthio, methoxycarbonyl or methyl-$SO_2$—.

In some embodiments, X is —$CH_3$, H,

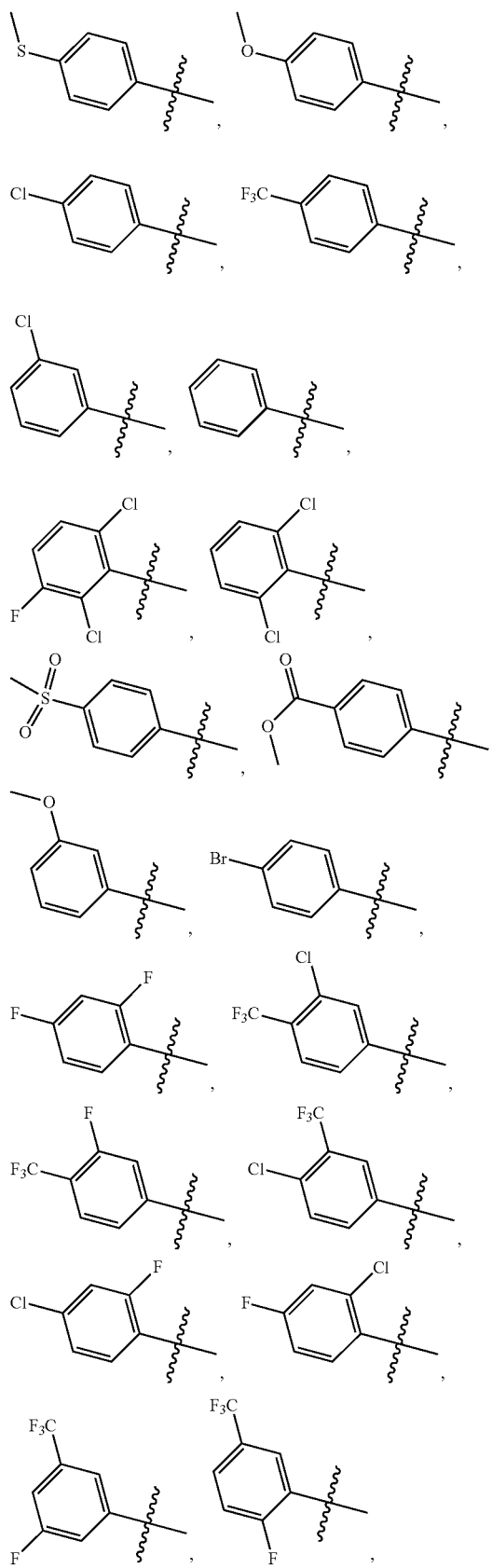

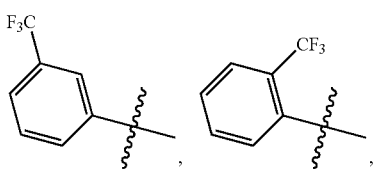

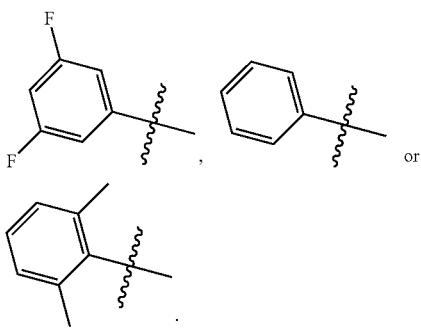

In some embodiments, Y is selected from

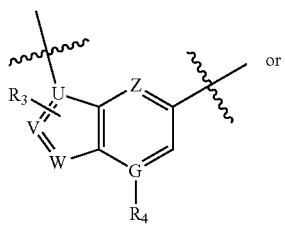

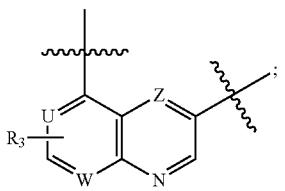

wherein, ═══ represents a single bond or a double bond, the U, V, W, G or Z is independently selected from C or N; when G is N, R₄ is absent; when G is C, R₄ is H or —N(R₅)—SO₂—R₆; wherein, R₅ and R₆ are each independently selected from H, C₁₋₆ alkyl or C₁₋₆ halogenoalkyl.

In some embodiments, Y is selected from

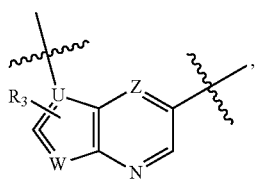

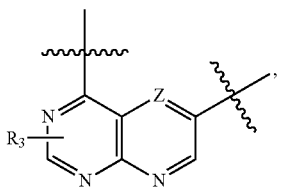

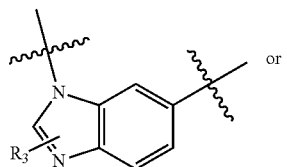

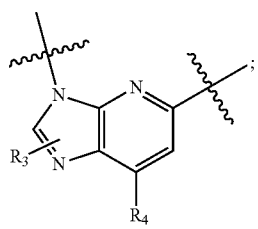

wherein, ═══ represents a single bond or a double bond, the U, W or Z is independently selected from C or N; R₃ is selected from H, halogen, hydroxyl, amino, C₁₋₆ alkyl, C₁₋₆ alkoxy, cyano or oxo; R₄ is H or —N(R₅)—SO₂—R₆; wherein R₅ and R₆ each are independently selected from H, C₁₋₆ alkyl or C₁₋₆ halogenoalkyl.

In some embodiments, R₃ is H, C₁₋₆ alkyl, C₁₋₆ alkoxy, cyano or oxo.

In some embodiments, R₃ is H, methyl or oxo.

In some embodiments, R₄ is —N(R₅)—SO₂—R₆.

In some embodiments, R₅ and R₆ are independently selected from H or C₁₋₆ alkyl.

In some embodiments, R₅ and R₆ are independently selected from H, methyl or ethyl.

In some embodiments, Y is

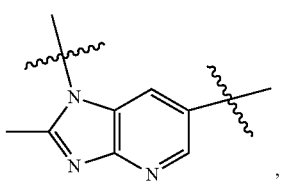

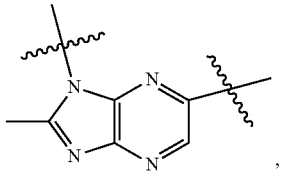

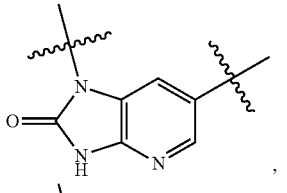

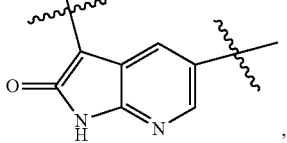

-continued

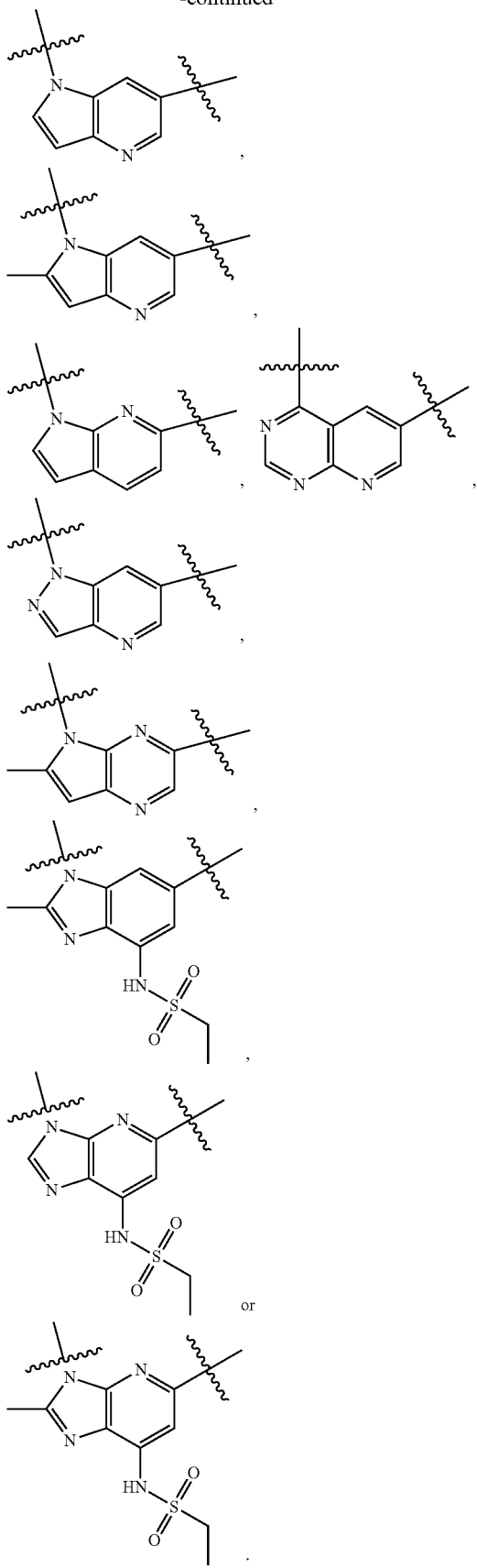

Preferably, Y is

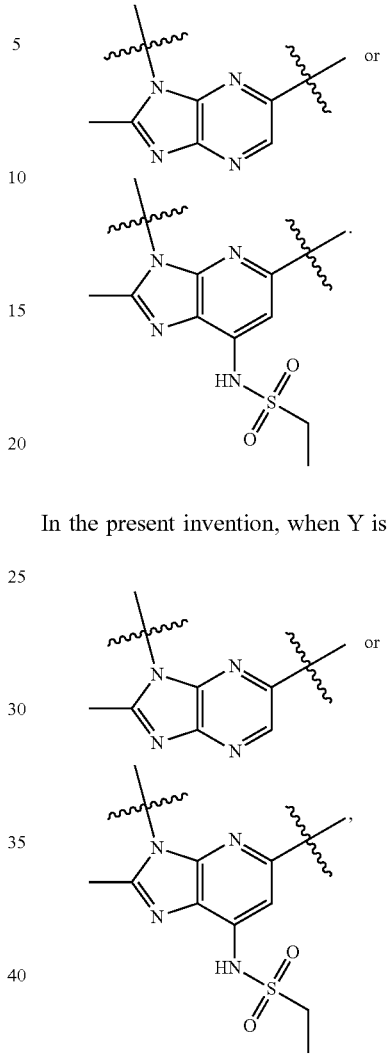

In the present invention, when Y is

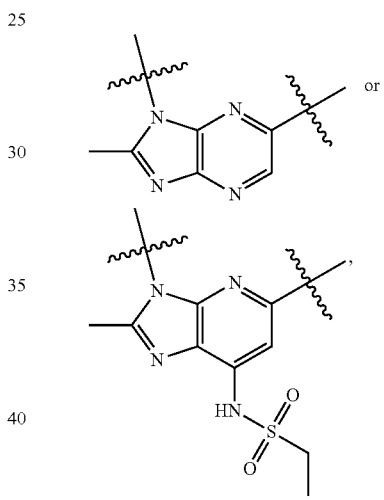

it not only maintains better potent, but also has better PK properties.

The present invention further provides a compound or a pharmaceutically acceptable salt thereof, the compound refers to:
1) 4-(1-(4-chlorobenzyl)-2-methyl-1H-imidazo[4,5-b]pyridin-6-yl)-6-methyl-1H-pyrrolo[2,3-c]pyridin-7(6H)-one;
2) 4-(1-(4-methoxybenzyl)-2-methyl-1H-imidazo[4,5-b]pyridin-6-yl)-6-methyl-1H-pyrrolo[2,3-c]pyridin-7(6H)-one;
3) 6-methyl-4-(2-methyl-1-(4-(methylthio)benzyl)-1H-imidazo[4,5-b]pyridin-6-yl)-1H-pyrrolo[2,3-c]pyridin-7(6H)-one;
4) 6-methyl-4-(2-methyl-1-(4-(trifluoromethyl)benzyl)-1H-imidazo[4,5-b]pyridin-6-yl)-1H-pyrrolo[2,3-c]pyridin-7(6H)-one;
5) 4-(1-(3-chlorobenzyl)-2-methyl-1H-imidazo[4,5-b]pyridin-6-yl)-6-methyl-1H-pyrrolo[2,3-c]pyridin-7(6H)-one;
6) 4-(1-benzyl-2-methyl-1H-imidazo[4,5-b]pyridin-6-yl)-6-methyl-1H-pyrrolo[2,3-c]pyridin-7(6H)one;
7) 4-(1,2-dimethyl-1H-imidazo[4,5-b]pyridin-6-yl)-6-methyl-1,6-dihydro-7H-pyrrolo[2,3-c]pyridin-7-one;

8) 6-methyl-4-(2-methyl-1H-imidazo[4,5-b]pyridin-6-yl)-1,6-dihydro-7H-pyrrolo[2,3-c]pyridin-7-one;
9) methyl 4-((2-methyl-6-(6-methyl-7-oxo-6,7-dihydro-1H-pyrrolo[2,3-c]pyridin-4-yl)-1H-imidazo[4,5-b]pyridin-1-yl)methyl)benzoate;
10) 6-benzyl-4-(1-(4-methoxybenzyl)-2-methyl-1H-imidazo[4,5-b]pyridin-6-yl)-1,6-dihydro-7H-pyrrolo[2,3-c]pyridin-7-one;
11) 6-isobutyl-4-(1-(4-methoxybenzyl)-2-methyl-1H-imidazo[4,5-b]pyridin-6-yl)-1,6-dihydro-7H-pyrrolo[2,3-c]pyridin-7-one;
12) 6-ethyl-4-(1-(4-methoxybenzyl)-2-methyl-1H-imidazo[4,5-b]pyridin-6-yl)-1,6-dihydro-7H-pyrrolo[2,3-c]pyridin-7-one;
13) 4-(1-(4-methoxybenzyl)-2-methyl-1H-imidazo[4,5-b]pyridin-6-yl)-2-methyl-1,6-dihydro-7H-pyrrolo[2,3-c]pyridin-7-one;
14) 4-(1-(4-methoxybenzyl)-2-methyl-1H-imidazo[4,5-b]pyridin-6-yl)-6-(thiazol-2-ylmethyl)-1,6-dihydro-7H-pyrrolo[2,3-c]pyridin-7-one;
15) 4-(1-(4-methoxybenzyl)-2-methyl-1H-imidazo[4,5-b]pyridin-6-yl)-6-(pyrazol-2-methyl)-1,6-dihydro-7H-pyrrolo[2,3-c]pyridin-7-one;
16) 4-(1-(3-methoxybenzyl)-2-methyl-1H-imidazo[4,5-b]pyridin-6-yl)-2-methyl-1,6-dihydro-7H-pyrrolo[2,3-c]pyridin-7-one;
17) 4-(1-(4-chlorobenzyl)-2-methyl-1H-imidazo[4,5-b]pyridin-6-yl)-6-(pyridin-3-ylmethyl)-1,6-dihydro-7H-pyrrolo[2,3-c]pyridin-7-one;
18) 4-(1-(4-chlorobenzyl)-2-methyl-1H-imidazo[4,5-b]pyrazin-6-yl)-6-methyl-1H-pyrrolo[2,3-c]pyridin-7(6H)-one;
19) 6-methyl-4-(2-methyl-1-(4-(trifluoromethyl)benzyl)-1H-imidazo[4,5-b]pyrazin-6-yl)-1H-pyrrolo[2,3-c]pyridin-7(6H)-one;
20) 4-(1-(4-methoxybenzyl)-2-methyl-H-imidazo[4,5-b]pyrazin-6-yl)-6-methyl-1H-pyrrolo[2,3-c]pyridin-7(6H)-one;
21) 4-(1-(1-(4-chlorophenyl)ethyl)-2-methyl-1H-imidazo[4,5-b]pyrazin-6-yl)-6-methyl-1,6-dihydro-7H-pyrrolo[2,3-c]pyridin-7-one;
22) 4-(1-benzyl-2-methyl-1H-imidazo[4,5-b]pyrazin-6-yl)-6-methyl-1H-pyrrolo[2,3-c]pyridin-7(6H)-one;
23) 4-(1-(3-trifluoromethylbenzyl)-2-methyl-1H-imidazo[4,5-b]pyrazin-6-yl)-6-methyl-1H-pyrrolo[2,3-c]pyridin-7(6H)-one;
24) 4-(1-(2-fluoro-5-trifluoromethylbenzyl)-2-methyl-1H-imidazo[4,5-b]pyrazin-6-yl)-6-methyl-1H-pyrrolo[2,3-c]pyridin-7(6H)-one;
25) 4-(1-(3-fluoro-5-trifluoromethylbenzyl)-2-methyl-1H-imidazo[4,5-b]pyrazin-6-yl)-6-methyl-1H-pyrrolo[2,3-c]pyridin-7(6H)-one;
26) 4-(1-(2-fluoro-4-chlorobenzyl)-2-methyl-H-imidazo[4,5-b]pyrazin-6-yl)-6-methyl-H-pyrrolo[2,3-c]pyridin-7(6H)-one;
27) 4-(1-(3-trifluoromethyl-4-chlorobenzyl)-2-methyl-1H-imidazo[4,5-b]pyrazin-6-yl)-6-methyl-1H-pyrrolo[2,3-c]pyridin-7(6H)-one;
28) 4-(1-(3-fluoro-4-trifluoromethylbenzyl)-2-methyl-1H-imidazo[4,5-b]pyrazin-6-yl)-6-methyl-1H-pyrrolo[2,3-c]pyridin-7(6H)-one;
29) 4-(1-(3-chloro-4-trifluoromethylbenzyl)-2-methyl-1H-imidazo[4,5-b]pyrazin-6-yl)-6-methyl-1H-pyrrolo[2,3-c]pyridin-7(6H)-one;
30) 4-(1-(4-chlorobenzyl)-2-methyl-1H-imidazo[4,5-b]pyrazin-6-yl)-6-methyl-1H-pyrrolo[2,3-c]pyridin-7(6H)-one;
31) 4-(1-(2,4-difluorobenzyl)-2-methyl-1H-imidazo[4,5-b]pyrazin-6-yl)-6-methyl-1H-pyrrolo[2,3-c]pyridin-7(6H)-one;
32) 4-(1-(4-bromobenzyl)-2-methyl-1H-imidazo[4,5-b]pyrazin-6-yl)-6-methyl-H-pyrrolo[2,3-c]pyridin-7(6H)-one;
33) 6-methyl-4-(2-methyl-1-(4-(methylsulfonyl)benzyl)-1H-imidazo[4,5-b]pyrazin-6-yl)-1H-pyrrolo[2,3-c]pyridin-7(6H)-one;
34) 1-(4-chlorobenzyl)-6-(6-methyl-7-oxo-6,7-dihydro-1H-pyrrolo[2,3-c]pyridin-4-yl)-1,3-dihydro-2H-imidazo[4,5-b]pyridin-2-one;
35) 4-(3-(1-(2,6-dichloro-3-fluorophenyl)ethyl)-2-methyl-H-pyrrolo[2,3-b]pyridin-5-yl)-6-methyl-1,6-dihydro-7H-pyrrolo[2,3-c]pyridin-7-one;
36) 4-(1-(2,6-dichlorobenzyl)-1H-pyrrolo[3,2-b]pyridin-6-yl)-6-methyl-1,6-dihydro-7H-pyrrolo[2,3-c]pyridin-7-one;
37) 4-(4-((4-chlorophenyl)amino)pyrido[2,3-d]pyrimidin-6-yl)-6-methyl-1,6-dihydro-7H-pyrrolo[2,3-c]pyridin-7-one;
38) 4-(1-(2,6-dichlorobenzyl)-2-methyl-1H-pyrrolo[3,2-b]pyridin-6-yl)-6-methyl-1,6-dihydro-7H-pyrrolo[2,3-c]pyridin-7-one;
39) 4-(1-(4-chlorobenzyl)-1H-pyrazolo[4,3-b]pyridin-6-yl)-6-methyl-1,6-dihydro-7H-pyrrolo[2,3-c]pyridin-7-one;
40) 4-(1-((4-chlorophenyl)sulfonyl)-1H-pyrrolo[2,3-b]pyridin-6-yl)-6-methyl-1,6-dihydro-7H-pyrrolo[2,3-c]pyridin-7-one;
41) N-(1-(4-chlorobenzyl)-2-methyl-6-(6-methyl-7-oxo-6,7-dihydro-1H-pyrrolo[2,3-c]pyridin-4-yl)-1H-benzo[d]imidazol-4-yl)ethanesulfonamide;
42) N-(2-methyl-6-(6-methyl-7-oxo-6,7-dihydro-1H-pyrrolo[2,3-c]pyridin-4-yl)-1-(4-(trifluoromethyl)benzyl)-1H-benzo[d]imidazol-4-yl)ethanesulfonamide;
43) N-(1-(4-methoxybenzyl)-2-methyl-6-(6-methyl-7-oxo-6,7-dihydro-H-pyrrolo[2,3-c]pyridin-4-yl)-1H-benzo[d]imidazol-4-yl)ethanesulfonamide;
44) N-(1-(1-(4-chlorophenyl)ethyl)-2-methyl-6-(6-methyl-7-oxo-6,7-dihydro-H-pyrrolo[2,3-c]pyridin-4-yl)-1H-benzo[d]imidazol-4-yl)ethanesulfonamide;
45) N-(1-benzyl-2-methyl-6-(6-methyl-7-oxo-6,7-dihydro-1H-pyrrolo[2,3-c]pyridin-4-yl)-1H-benzo[d]imidazol-4-yl)ethanesulfonamide;
46) N-(2-methyl-6-(6-methyl-7-oxo-6,7-dihydro-1H-pyrrolo[2,3-c]pyridin-4-yl)-1-(3-(trifluoromethyl)benzyl)-1H-benzo[d]imidazol-4-yl)ethanesulfonamide;
47) N-(2-methyl-6-(6-methyl-7-oxo-6,7-dihydro-1H-pyrrolo[2,3-c]pyridin-4-yl)-1-(2-fluoro-5-(trifluoromethyl)benzyl)-1H-benzo[d]imidazol-4-yl)ethanesulfonamide;
48) N-(2-methyl-6-(6-methyl-7-oxo-6,7-dihydro-1H-pyrrolo[2,3-c]pyridin-4-yl)-1-(3-fluoro-5-(trifluoromethyl)benzyl)-1H-benzo[d]imidazol-4-yl)ethanesulfonamide;
49) N-(2-methyl-6-(6-methyl-7-oxo-6,7-dihydro-1H-pyrrolo[2,3-c]pyridin-4-yl)-1-(2-fluoro-4-chlorobenzyl)-1H-benzo[d]imidazol-4-yl)ethanesulfonamide;
50) N-(2-methyl-6-(6-methyl-7-oxo-6,7-dihydro-1H-pyrrolo[2,3-c]pyridin-4-yl)-1-(3-(trifluoromethyl)-4chlorobenzyl)-1H-benzo[d]imidazol-4-yl)ethanesulfonamide;
51) N-(2-methyl-6-(6-methyl-7-oxo-6,7-dihydro-1H-pyrrolo[2,3-c]pyridin-4-yl)-1-(3-fluoro-4-(trifluoromethyl)benzyl)-1H-benzo[d]imidazol-4-yl)ethanesulfonamide;
52) N-(2-methyl-6-(6-methyl-7-oxo-6,7-dihydro-1H-pyrrolo[2,3-c]pyridin-4-yl)-1-(3-chloro-4-(trifluoromethyl)benzyl)-1H-benzo[d]imidazol-4-yl)ethanesulfonamide;

53) N-(2-methyl-6-(6-methyl-7-oxo-6,7-dihydro-1H-pyrrolo[2,3-c]pyridin-4-yl)-1-(3-chlorobenzyl)-1H-benzo[d]imidazol-4-yl)ethanesulfonamide;
54) N-(2-methyl-6-(6-methyl-7-oxo-6,7-dihydro-1H-pyrrolo[2,3-c]pyridin-4-yl)-1-(2,4-difluorobenzyl)-1H-benzo[d]imidazol-4-yl)ethanesulfonamide;
55) N-(2-methyl-6-(6-methyl-7-oxo-6,7-dihydro-1H-pyrrolo[2,3-c]pyridin-4-yl)-1-(4-bromobenzyl)-1H-benzo[d]imidazol-4-yl)ethanesulfonamide;
56) N-(2-methyl-6-(6-methyl-7-oxo-6,7-dihydro-1H-pyrrolo[2,3-c]pyridin-4-yl)-1-(4-(methylsulfonyl)benzyl)-1H-benzo[d]imidazol-4-yl)ethanesulfonamide;
57) N-(1-(2-chloro-4-fluorobenzyl)-2-methyl-6-(6-methyl-7-oxo-6,7-dihydro-1H-pyrrolo[2,3-c]pyridin-4-yl)-1H-benzo[d]imidazol-4-yl)ethanesulfonamide;
58) N-(5-(6-methyl-7-oxo-6,7-dihydro-1H-pyrrolo[2,3-c]pyridin-4-yl)-3-(4-(trifluoromethyl)benzyl)-3H-imidazo[4,5-b]pyridin-7-yl)ethanesulfonamide;
59) N-(3-(2,4-difluorobenzyl)-5-(6-methyl-7-oxo-6,7-dihydro-1H-pyrrolo[2,3-c]pyridin-4-yl)-3H-imidazo[4,5-b]pyridin-7-yl)ethanesulfonamide;
60) N-(3-(1-(4-chlorophenyl)ethyl)-5-(6-methyl-7-oxo-6,7-dihydro-1H-pyrrolo[2,3-c]pyridin-4-yl)-3H-imidazo[4,5-b]pyridin-7-yl)ethanesulfonamide;
61) N-(3-(2-fluoro-5-(trifluoromethyl)benzyl)-5-(6-methyl-7-oxo-6,7-dihydro-H-pyrrolo[2,3-c]pyridin-4-yl)-3H-imidazo[4,5-b]pyridin-7-yl)ethanesulfonamide;
62) N-(3-(3,5-difluorobenzyl)-5-(6-methyl-7-oxo-6,7-dihydro-H-pyrrolo[2,3-c]pyridin-4-yl)-3H-imidazo[4,5-b]pyridin-7-yl)ethanesulfonamide;
63) N-(5-(6-methyl-7-oxo-6,7-dihydro-H-pyrrolo[2,3-c]pyridin-4-yl)-3-(2-(trifluoromethyl)benzyl)-3H-imidazo[4,5-b]pyridin-7-yl)ethanesulfonamide;
64) N-(3-(2,4-difluorobenzyl)-2-methyl-5-(6-methyl-7-oxo-6,7-dihydro-H-pyrrolo[2,3-c]pyridin-4-yl)-3H-imidazo[4,5-b]pyridin-7-yl)ethanesulfonamide;
65) N-(2-methyl-5-(6-methyl-7-oxo-6,7-dihydro-1H-pyrrolo[2,3-c]pyridin-4-yl)-3-(4-(trifluoromethyl)benzyl)-3H-imidazo[4,5-b]pyridin-7-yl)ethanesulfonamide;
66) N-(2-methyl-5-(6-methyl-7-oxo-6,7-dihydro-1H-pyrrolo[2,3-c]pyridin-4-yl)-3-(2-(trifluoromethyl)benzyl)-3H-imidazo[4,5-b]pyridin-7-yl)ethanesulfonamide;
67) N-(3-(3,5-difluorobenzyl)-2-methyl-5-(6-methyl-7-oxo-6,7-dihydro-H-pyrrolo[2,3-c]pyridin-4-yl)-3H-imidazo[4,5-b]pyridin-7-yl)ethanesulfonamide; or
68) N-(3-(2,6-dimethylbenzyl)-2-methyl-5-(6-methyl-7-oxo-6,7-dihydro-1H-pyrrolo[2,3-c]pyridin-4-yl)-3H-imidazo[4,5-b]pyridin-7-yl)ethanesulfonamide.

The invention further provides crystalline form I of 6-methyl-4-(2-methyl-1-(4-(trifluoromethyl)benzyl)-1H-imidazo[4,5-b]pyrazin-6-yl)-1H-pyrrolo[2,3-c]pyridin-7(6H)-one (Compound 19).

Compound 19

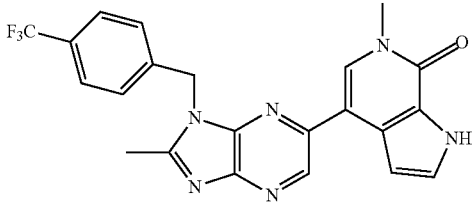

In some embodiments, the X-ray powder diffraction pattern of the above crystalline form I has characteristic peaks with diffraction angles 2θ of 13.80.2°, 18.90.2°, 26.00.2°.

In some embodiments, the X-ray powder diffraction pattern of the above crystalline form I has characteristic peaks with diffraction angles 2θ of 6.2±0.2°, 13.8±0.2°, 18.9±0.2°, 19.5±0.2°, 26.0±0.2°, 26.8±0.2°.

In some embodiments, the above crystalline form I has an X-ray powder diffraction pattern as shown in FIG. 1.

The present invention summarized the characteristic peaks in the X-ray powder diffraction pattern of the above crystalline form I, as shown in Table 1.

TABLE 1

| No. | 2θ ± 0.2 (°) | Crystal plane spacing [Å] | Relative intensity (%) |
| --- | --- | --- | --- |
| 1 | 6.2 | 14.2 | 60.8 |
| 2 | 13.8 | 6.4 | 100.0 |
| 3 | 18.9 | 4.7 | 31.6 |
| 4 | 19.5 | 4.5 | 10.4 |
| 5 | 26.0 | 3.4 | 31.8 |
| 6 | 26.8 | 3.3 | 22.1 |

In some embodiments, crystalline form I of the present invention can be identified by differential scanning calorimetry. In some embodiments, crystalline form I has a differential scanning calorimetry curve as shown in FIG. 2. In the DSC pattern, the endothermic peak of crystalline form I is about 288.9° C. Differential scanning calorimetry analysis was performed by TA instruments Q200 DSC (purge gas: nitrogen; flow rate: 40 mL/min; heating rate: 10° C./min).

In some embodiments, the crystalline form I of the present invention can be identified by $^1$HNMR, and the data of $^1$HNMR is as follows: $^1$H NMR (400 MHz, DMSO) δ 12.17 (s, 1H), 8.94 (s, 1H), 8.05 (s, 1H), 7.75 (d, J=8.0 Hz, 2H), 7.50 (d, J=8.0 Hz, 2H), 7.30 (m, 1H), 6.77 (m, 1H), 5.70 (s, 2H), 3.65 (s, 3H), 2.65 (s, 3H).

Preferably, the purity of the crystalline form I is ≥85%.
Preferably, the purity of the crystalline form I is ≥95%.
Preferably, the purity of the crystalline form I is ≥99%.
Preferably, the purity of the crystalline form I is ≥99.5%.
Preferably, the crystalline form I is anhydrous.

The crystalline form I provided by the invention has the characteristics of good crystallinity, non-hygroscopicity and good stability, and has acceptable oral bioavailability.

The present invention also provides a pharmaceutical composition comprising a therapeutically effective amount of at least one of the above compounds and a pharmaceutically acceptable excipient, such as hydroxypropyl methyl cellulose. In the composition, the said compound in a weight ratio to the said excipient within the range from about 0.0001 to about 10.

In addition, the present invention also provides a method for treating a subject suffering from a disease or disorder that responds to an inhibitory response to a bromodomain-containing protein, which comprises administering the therapeutically effective amount of the compound of formula (I) or the pharmaceutically acceptable salt thereof. In certain aspects, the bromodomain-containing protein is BRD4.

In certain aspects, the disease or disorder is selected from autoimmune diseases, inflammatory diseases, neurodegenerative diseases, cardiovascular disorders, kidney disorders, viral infections, and obesity. In certain aspects, the disease or disorder is selected from rheumatoid arthritis, osteoarthritis, atherosclerosis, psoriasis, systemic lupus erythematosus, multiple sclerosis, inflammatory bowel disease, asthma, chronic obstructive airway disease, pneumonia, dermatitis, hair loss, nephritis, vasculitis, atherosclerosis, Alzheimer's disease, hepatitis, primary biliary cirrhosis, sclerosing cholangitis, diabetes (including type 1 diabetes), acute rejection of transplanted organs. In certain aspects, the disease or disorder is cancer, including hematological cancer, lymphoma, multiple myeloma, leukemia, neoplasm, cancer, or tumor (eg, solid tumor). In certain aspects, the disease or disorder is tumor or cancer of colon, rectum, prostate (eg castrate resistant prostate cancer), lung cancer (eg non-small cell lung cancer and/or small cell lung cancer), pancreas, liver, kidney, cervix, uterus, stomach, ovary, breast (eg basal or basal-like breast cancer and/or triple negative breast cancer), skin (eg melanoma), nervous system (including brain, meninges, and central nervous system, Including neuroblastoma, glioblastoma, meningioma and medulloblastoma). In certain aspects, the disease or disorder is cancer. In certain aspects, the disease or disorder is hepatocellular carcinoma. In certain aspects, the disease or disorder is lymphoma. In certain aspects, the disease or disorder is B-cell lymphoma. In certain aspects, the disease or disorder is Burkitt's lymphoma. In certain aspects, the disease or disorder is diffuse large B-cell lymphoma. In certain aspects, the disease or disorder is multiple myeloma. In certain aspects, the disease or disorder is chronic lymphocytic leukemia. In certain aspects, the disease or disorder is NUT midline cardinoma. In certain aspects, the subject is human.

In certain aspects, the compound is administered intravenously, intramuscularly, parenterally, nasally, or orally. In one aspect, the compound is administered orally.

The present invention also provides a method for inhibiting bromodomain proteins, which comprises contacting the bromodomain proteins with a compound of formula (I) or a pharmaceutically acceptable salt thereof.

The present invention also provides the use of the compound of formula (I) or a pharmaceutically acceptable salt thereof in the preparation of a medicament for treating a disease or condition that responds to the inhibition of bromodomain proteins.

The present invention also provides a compound of formula (I) or a pharmaceutically acceptable salt thereof for treatment. Further provided is the compound of formula (I) or the pharmaceutically acceptable salt thereof for treating a subject suffering from a disease or disorder that responds to an inhibitory response to a bromodomain-containing protein. Also provided is the compound of formula (I) or pharmaceutically acceptable salts thereof for the above treatment methods.

In the present invention, unless otherwise stated, the term "halogen" refers to fluorine, chlorine, bromine or iodine. Preferably, halogen refers to fluorine, chlorine and bromine.

In the present invention, unless otherwise stated, the term "alkyl" includes a straight, branched or cyclic saturated monovalent hydrocarbon. For example, alkyl includes methyl, ethyl, propyl, isopropyl, cyclopropyl, n-butyl, isobutyl, sec-butyl, tert-butyl, cyclobutyl, n-pentyl, 3-(2-methyl)butyl, 2-pentyl, 2-methylbutyl, neopentyl, cyclopentyl, n-hexyl, 2-hexyl, 2-methylpentyl and cyclohexyl. Similarly, "$C_{1-6}$" in $C_{1-6}$ alkyl refers to a group containing 1, 2, 3, 4, 5 or 6 carbon atoms arranged in a linear or branched chain.

The alkoxy refers to oxyether formed from the above-mentioned straight chain, branch chain or cyclic alkyl.

In the present invention, unless otherwise stated, the term "heteroaryl" refers to a substituted or unsubstituted stable monocyclic or bicyclic group containing at least one aromatic ring of 5 to 10 ring atoms, the aromatic ring containing one, two or three ring heteroatoms selected from N, O and S, the remaining ring atoms are C atoms. Examples of such heteroaryl groups include, but are not limited to, pyridyl, pyrimidinyl, pyrrolyl, imidazolyl, thiazolyl, thienyl, benzimidazole.

The term "composition", as used herein, is intended to encompass a product comprising the specified ingredients in the specified amounts, as well as any product which results, directly or indirectly, from combinations of the specified ingredients in the specified amounts. Accordingly, is pharmaceutical compositions containing the compounds of the present invention as the active ingredient as well as methods of preparing the instant compounds are also part of the present invention. Furthermore, some of the crystalline forms for the compounds may exist as polymorphs and as such are intended to be included in the present invention. In addition, some of the compounds may form solvates with water (i.e., hydrates) or common organic solvents and such solvates are also intended to be encompassed within the scope of this invention.

The present invention includes within its scope the prodrugs of the compounds of this invention. In general, such prodrugs will be functional derivatives of the compounds that are readily converted in vivo into the required compound. Thus, in the methods of treatment of the present invention, the term "administering" shall encompass the treatment of the various disorders described with the compound specifically disclosed or with a compound which may not be specifically disclosed, but which converts to the specified compound in vivo after administration to the subject. Conventional procedures for the selection and preparation of suitable prodrug derivatives has been described in bools such as "Design of Prodrugs", ed. H. Bundgaard, Elsevier, 1985.

Obviously, the definition of any substituent or variable in a specific position in a molecule is independent of other positions in the molecule. It is easy to understand that a person of ordinary skill in the art can select a substituent or a substituted form of the compound of the present invention through the prior art means and the method described in the present invention to provide a chemically stable and easily synthesized compound.

The present invention includes compounds described herein can contain one or more asymmetric centers and may thus give rise to diastereomers and optical isomers. The present invention includes all such possible diastereomers as well as their racemic mixtures, their substantially pure resolved enantiomers, all possible geometric isomers, and pharmaceutically acceptable salts thereof.

The above Formula I are shown without a definitive stereochemistry at certain positions. The present invention includes all stereoisomers of Formula I and pharmaceutically acceptable salts thereof. Further, mixtures of stereoisomers as well as isolated specific stereoisomers are also included. During the course of the synthetic procedures used to prepare such compounds, or in using racemization or epimerization procedures known to those skilled in the art, the products of such procedures can be a mixture of stereoisomers.

When a tautomer of the compound of Formula I exists, the present invention includes any possible tautomers and pharmaceutically acceptable salts thereof, and mixtures thereof, except where specifically stated otherwise.

When the compound of Formula I and pharmaceutically acceptable salts thereof exist in the form of solvates or polymorphic forms, the present invention includes any possible solvates and polymorphic forms. A type of a solvent that forms the solvate is not particularly limited so long as the solvent is pharmacologically acceptable. For example, water, ethanol, propanol, acetone and similar solvents can be used.

The term "pharmaceutically acceptable salts" refers to salts prepared from pharmaceutically acceptable non-toxic bases or acids. When the compound of the present invention is acidic, its corresponding salt can be conveniently prepared from pharmaceutically acceptable non-toxic bases, including inorganic bases and organic bases. Salts derived from such inorganic bases include aluminum, ammonium, calcium, copper (ic and ous), ferric, ferrous, lithium, magnesium, manganese (ic and ous), potassium, sodium, zinc and the like salts. Particularly preferred are the ammonium, calcium, magnesium, potassium and sodium salts. Salts derived from pharmaceutically acceptable organic non-toxic bases include salts of primary, secondary, and tertiary amines, as well as cyclic amines and substituted amines such as naturally occurring and synthesized substituted amines. Other pharmaceutically acceptable organic non-toxic bases from which salts can be formed include ion exchange resins such as, for example, arginine, betaine, caffeine, choline, N',N'-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine and the like.

When the compound of the present invention is basic, its corresponding salt can be conveniently prepared from pharmaceutically acceptable non-toxic acids, including inorganic and organic acids. Such acids include, for example, acetic, benzenesulfonic, benzoic, camphorsulfonic, citric, ethanesulfonic, formic, fumaric, gluconic, glutamic, hydrobromic, is hydrochloric, isethionic, lactic, maleic, malic, mandelic, methanesulfonic, mucic, nitric, pamoic, pantothenic, phosphoric, succinic, sulfuric, tartaric, p-toluenesulfonic acid and the like. Preferred are citric, hydrobromic, formic, hydrochloric, maleic, phosphoric, sulfuric and tartaric acids, particularly preferred are formic and hydrochloric acid. Since the compounds of Formula I are intended for pharmaceutical use they are preferably provided in substantially pure form, for example at least 60% pure, more suitably at least 75% pure, especially at least 98% pure (% are on a weight for weight basis).

The pharmaceutical compositions of the present invention comprise a compound represented by Formula I (or a pharmaceutically acceptable salt thereof) as an active ingredient, a pharmaceutically acceptable carrier and optionally other therapeutic ingredients or adjuvants. Although the most suitable route in any given case will depend on the particular host to be administered, the nature of the host and severity of the conditions, the pharmaceutical of the present invention include compositions suitable for oral, rectal, topical, and parenteral (including subcutaneous, intramuscular, and intravenous) administration. The pharmaceutical compositions may be conveniently presented in unit dosage form and prepared by any of the methods well known in the art of pharmacy.

As described herein, the new crystalline forms may be identified by powder X-ray diffraction spectrum. However, persons skilled in the art know that the peak intensity and/or peak condition of powder X-ray diffraction may be different due to different experimental conditions, such as different diffraction test conditions and/or orientation priority. And because of the different accuracy of different instruments, the measured 2θ value will have an error of about ±0.2°. However, it is known that the relative strength value of the peak is more dependent on some properties of the measured sample than the position of the peak, such as the size of the crystal in the sample, the orientation of the crystal and the purity of the material to be analyzed, so the peak strength deviation shown can occur in the range of about 20% or more. However, despite the experimental error, instrument error, and orientation priority, persons skilled in the art can also obtain sufficient information to identify the crystalline form from the XRD data provided in the patent.

In practice, the compounds represented by Formula I, or a prodrug, or a metabolite, or pharmaceutically acceptable salts thereof, of this invention can be combined as the active ingredient in intimate admixture with a pharmaceutical carrier according to conventional pharmaceutical compounding techniques. The carrier may take a wide variety of forms depending on the form of preparation desired for administration, e.g., oral or parenteral (including intravenous). Thus, the pharmaceutical compositions of the present invention can be presented as discrete units suitable for oral administration such as capsules, cachets or tablets each containing a predetermined amount of the active ingredient. Further, the compositions can be presented as a powder, as granules, as a solution, as a suspension in an aqueous liquid, as a non-aqueous liquid, as oil-in-water emulsion, or as a water-in-oil liquid emulsion. In addition to the common dosage forms set out above, the compound represented by Formula I, or a pharmaceutically acceptable salt thereof, may also be administered by controlled release means and/or delivery devices. The compositions may be prepared by any of the methods of pharmacy. In general, such methods include a step of bringing into association the active ingredient with the carrier that constitutes one or more necessary ingredients. In general, the compositions are prepared by uniformly and intimately admixing the active ingredient with liquid carriers or finely divided solid carriers or both. The product can then be conveniently shaped into the desired presentation.

Thus, the pharmaceutical compositions of this invention may include a pharmaceutically acceptable carrier and a compound, or a pharmaceutically acceptable salt, of Formula I. The compounds of Formula I, or pharmaceutically acceptable salts thereof, can also be included in pharmaceutical compositions in combination with one or more other therapeutically active compounds.

The pharmaceutical carrier employed can be, for example, a solid, liquid, or gas. Examples of solid carriers include such as lactose, terra alba, sucrose, talc, gelatin, agar, pectin, acacia, magnesium stearate, and stearic acid. Examples of liquid carriers include such as sugar syrup, peanut oil, olive oil, and water. Examples of gaseous carriers include such as carbon dioxide and nitrogen. In preparing the compositions for oral dosage form, any convenient pharmaceutical media may be employed. For example, water, glycols, oils, alcohols, flavoring agents, preservatives, coloring agents, and the like may be used to form oral liquid preparations such as suspensions, elixirs and solutions; while carriers such as starches, sugars, microcrystalline cellulose, diluents, granulating agents, lubricants, binders, disintegrating agents, and the like may be used to form oral solid preparations such as powders, capsules and tablets. Because of their ease of administration, tablets and capsules are the preferred oral dosage units whereby solid pharmaceutical carriers are employed. Optionally, tablets may be coated by standard aqueous or nonaqueous techniques.

A tablet containing the composition of this invention may be prepared by compression or molding, optionally with one or more accessory ingredients or adjuvants. Compressed tablets may be prepared by compressing, in a suitable machine, the active ingredient in a free-flowing form such as powder or granules, optionally mixed with a binder, lubricant, inert diluent, surface active or dispersing agent. Molded tablets may be made by molding in a suitable machine, a mixture of the powdered compound moistened with an inert liquid diluent. Each tablet preferably contains from about 0.05 mg to about 5 g of the active ingredient and each cachet or capsule preferably containing from about 0.05 mg to about 5 g of the active ingredient. For example, a formulation intended for the oral administration to humans may contain from about 0.5 mg to about 5 g of active agent, compounded with an appropriate and convenient amount of carrier material which may vary from about 5 to about 95 percent of the total composition. Unit dosage forms will generally contain between from about 1 mg to about 2 g of the active ingredient, typically 25 mg, 50 mg, 100 mg, 200 mg, 300 mg, 400 mg, 500 mg, 600 mg, 800 mg, or 1000 mg.

Pharmaceutical compositions of the present invention suitable for parenteral administration may be prepared as solutions or suspensions of the active compounds in water. A suitable surfactant can be included such as, for example, hydroxypropylcellulose. Dispersions can also be prepared in glycerol, liquid polyethylene glycols, and mixtures thereof in oils. Further, a preservative can be included to prevent the detrimental growth of microorganisms.

Pharmaceutical compositions of the present invention suitable for injectable use include sterile aqueous solutions or dispersions. Furthermore, the compositions can be in the form of sterile powders for the extemporaneous preparation of such sterile injectable solutions or dispersions. In all cases, the final injectable form must be sterile and must be effectively fluid for easy syringability. The pharmaceutical compositions must be stable under the conditions of manufacture and storage; thus, preferably should be preserved against the contaminating action of microorganisms such as bacteria and fungi. The carrier can be a solvent or dispersion medium containing, for example, water, ethanol, polyol (e.g., glycerol, propylene glycol and liquid polyethylene glycol), vegetable oils, and suitable mixtures thereof.

Pharmaceutical compositions of the present invention can be in a form suitable for topical use such as, for example, an aerosol, cream, ointment, lotion, dusting powder, or the like. Further, the compositions can be in a form suitable for use in transdermal devices. These formulations may be prepared, utilizing a compound represented by Formula I of this invention, or a pharmaceutically acceptable salt thereof, via conventional processing methods. As an example, a cream or ointment is prepared by admixing hydrophilic material and water, together with about 5 wt % to about 10 wt % of the compound, to produce a cream or ointment having a desired consistency.

Pharmaceutical compositions of this invention can be in a form suitable for rectal administration with solid as a carrier. It is preferable that the mixture forms unit dose suppositories. Suitable carriers include cocoa butter and other materials commonly used in the art. The suppositories may be conveniently formed by first admixing the composition with the softened or melted carrier(s) followed by chilling and shaping in molds.

In addition to the aforementioned carrier ingredients, the pharmaceutical formulations described above may include, as appropriate, one or more additional carrier ingredients such as diluents, buffers, flavoring agents, binders, surface-active agents, thickeners, lubricants, preservatives (including antioxidants) and the like. Furthermore, other adjuvants can be included to render the formulation isotonic with the blood of the intended recipient. Compositions containing a compound described by Formula I, or pharmaceutically acceptable salts thereof, may also be prepared in powder or liquid concentrate form.

Generally, dosage levels on the order of from about 0.01 mg/kg to about 150 mg/kg of body weight per day are useful in the treatment of the above-indicated conditions, or alternatively about 0.5 mg to about 7 g per patient per day. For example, colon cancer, rectal cancer, mantle cell lymphoma, multiple myeloma, breast cancer, prostate cancer, glioblastoma, squamous cell esophageal cancer, liposarcoma, T-cell lymphoma melanoma, pancreatic cancer, glioblastoma or lung cancer, may be effectively treated by the administration of from about 0.01 to 50 mg of the compound per kilogram of body weight per day, or alternatively about 0.5 mg to about 3.5 g per patient per day.

However, it is understood that the specific dose level for any particular patient will depend on a number of factors, including age, weight, general health, gender, diet, timing of administration, route of administration, excretion rate, status of combination medications and the severity of the specific disease being treated.

EXAMPLES

Figure 1:
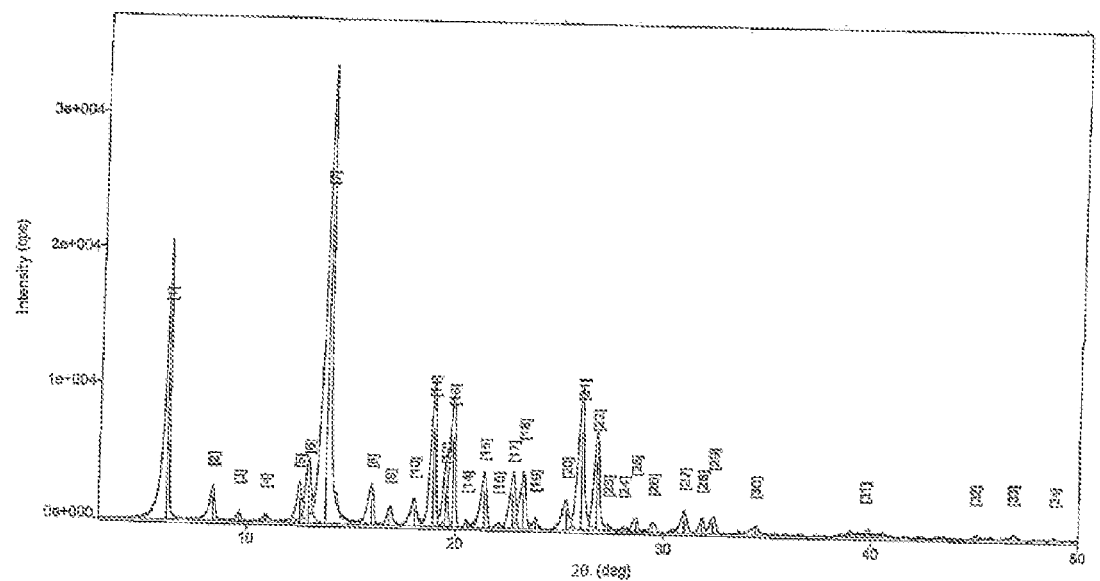
FIG. 1: XRD pattern for crystalline form I of Compound 19.
Figure 2:
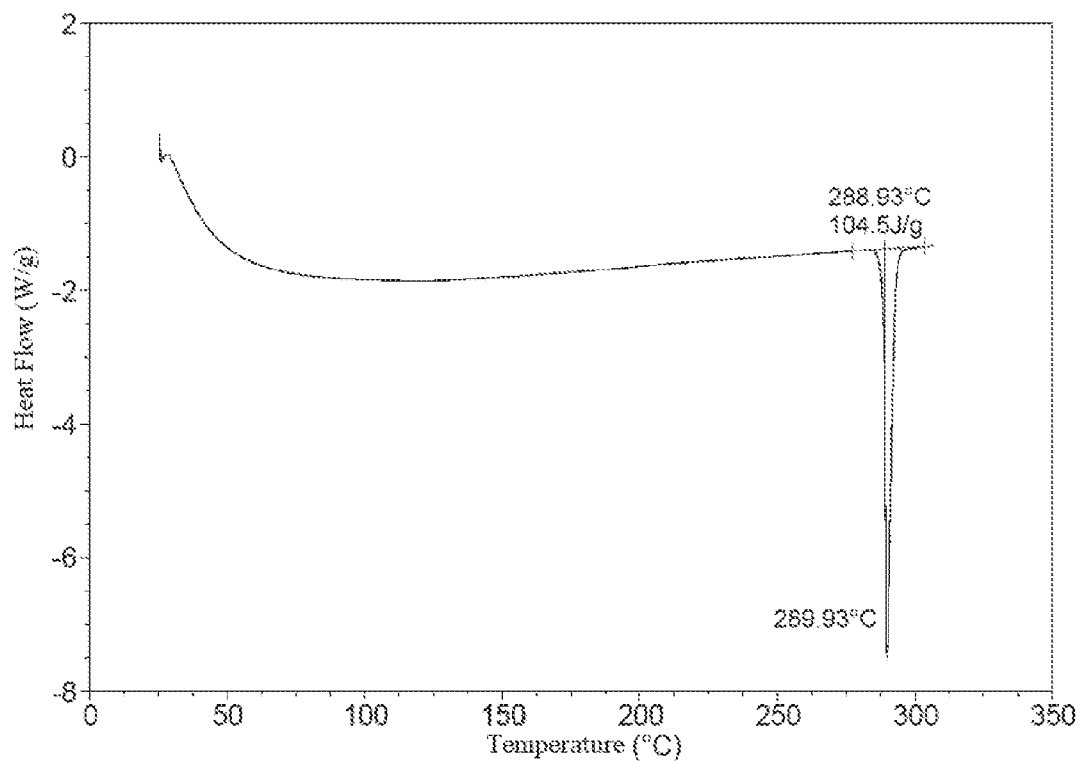
FIG. 2: DSC pattern for crystalline form I of Compound 19.

In order to make the present invention easier to understand, the present invention will be described in detail below in conjunction with examples, which are merely illustrative and not limited to the scope of application of the present invention. Specific experimental methods not mentioned in the following embodiments are generally carried out in accordance with conventional experimental methods.

Unless otherwise stated, all parts and percentages are calculated by weight, and all temperatures are in degrees Celsius.

The following abbreviations are used in the examples:
AcOH: Acetic acid;
(BPin)$_2$: Bis(pinacolato)diboron;
BRD4(D1): Bromodomain protein 4 (domain 1);
BRD4(D2): Bromodomain protein 4 (domain 2);
CDI: N,N'-Carbonyldiimidazole;
DCM: Dichloromethane;
DIEA: N,N-Diisopropylethylamine;
DMA: N, N-dimethylacetamide;
DMF: N, N-dimethylformamide;
DMSO: Dimethyl sulfoxide;
EA: Ethyl acetate;
EtOH: Ethanol;

h: hour;
¹HNMR: Proton nuclear magnetic resonance;
KAcO: Potassium acetate;
LCMS: Liquid Chromatograph Mass Spectrometer;
LDA: Lithium diisopropylamide;
MeI: Methyl iodide;
MeOH: Methanol;
min: minute;
NaBH$_4$: Sodium borohydride;
NaH: Sodium hydride;
n-Hex: n-hexane;
Pd$_2$(dba)$_3$: Tris(dibenzylideneacetone)dipalladium;
Pd(dppf) Cl2.DCM: [1,1'-Bis(diphenylphosphino)ferrocene]palladium(II)dichloride dichloromethane complex;
Pd(PPh$_3$)$_4$: Tetrakis(triphenylphosphine)palladium;
Pd(PPh$_3$)$_2$Cl$_2$: Bis(triphenylphosphine)palladium(II) chloride;
PE: Petroleum ether;
POCl$_3$: Phosphorus oxychloride;
s: second;
TEA: Triethylamine;
TfOH: Trifluoromethanesulfonic acid;
THF: Tetrahydrofuran;
TLC: Thin layer chromatography;
TsCl: P-toluenesulfonyl chloride;
XPhos: 2-Dicyclohexylphosphino-2',4',6'-triisopropylbiphenyl.

Unless otherwise stated, in the following examples, the information and method parameters of the detection instruments used are as follows:

TABLE 2

| Device name | X-ray powder diffractometer (XRD)& heating stage XRD |
|---|---|
| Equipment | Bruker D8 Advance diffractometer |
| Technical Specifications | Kα radiation (40 Kv, 40 Ma) with a copper target wavelength of 1.54 nm, θ-2θ goniometer, Mo monochromator, Lynxeye detector |
| Calibrated substance | Al$_2$O$_3$ |
| Acquisition software | Diffrac Plus XRD Commander |
| Analysis software | MDI Jade 6 |
| Method parameters | Non reflective sample plate specification 24.6 mm diameter × 1.0 mm thickness |
| | Variable temperature hot sample plate Copper plate |
| | Step length 0.02°/step |
| | Residence time 0.1 s/step |

TABLE 3

| Device name | Dynamic Vapor Sorption (DVS) | |
|---|---|---|
| Instrument | TA Instruments Q5000TGA | |
| Control software | Thermal Adventage | |
| Analysis software | Universal Analysis | |
| Sample plate | Platinum crucible | |
| Sample detection amount | 1-10 mg | |
| Protective gas | Nitrogen | |
| Gas flow rate | 10 mL/min | |
| Judgment standard | non-hygroscopic | Not more than 0.2% |
| | Mild hygroscopic | More than 0.2%, but not more than 2.0% |
| | Hygroscopic | More than 2%, but not more than 15% |
| | Extremely hygroscopic | More than 15% |

Example 1 Synthesis of Compound 1 (4-(1-(4-chlorobenzyl)-2-methyl-1H-imidazo[4,5-b]pyridin-6-yl)-6-methyl-1H-pyrrolo[2,3-c]pyridin-7(6H)-one)

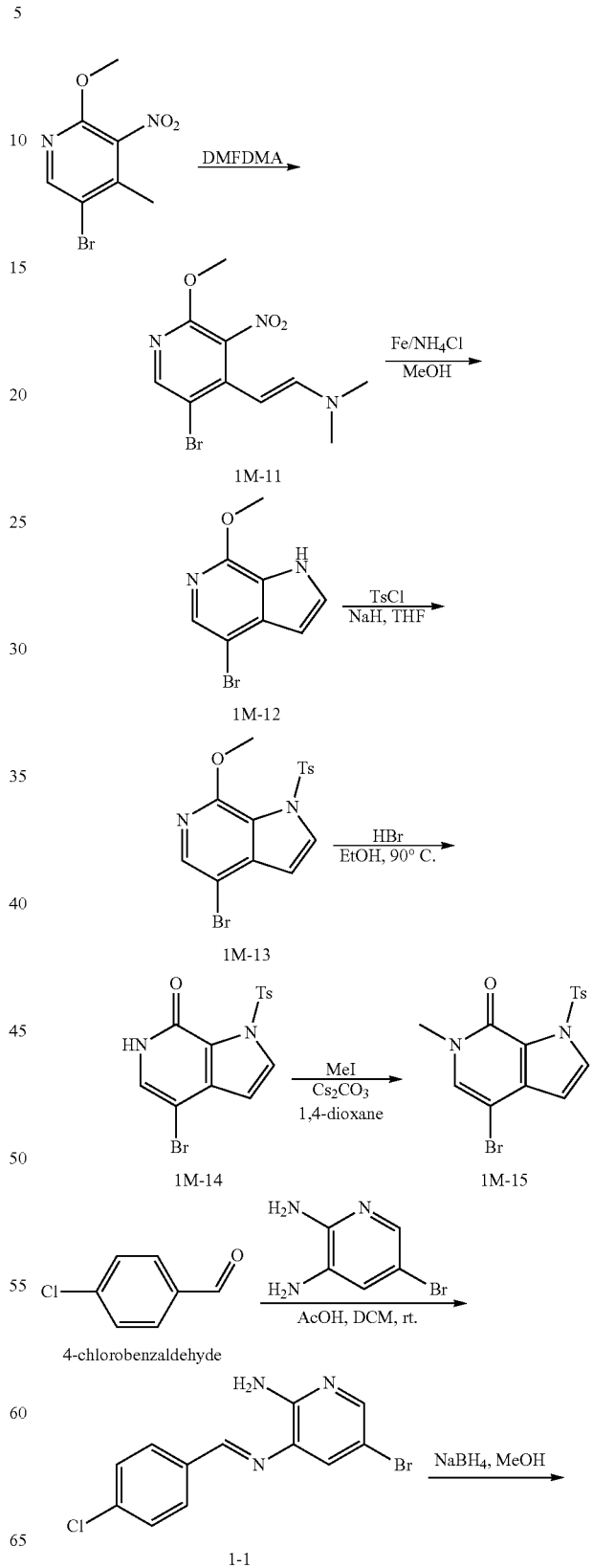

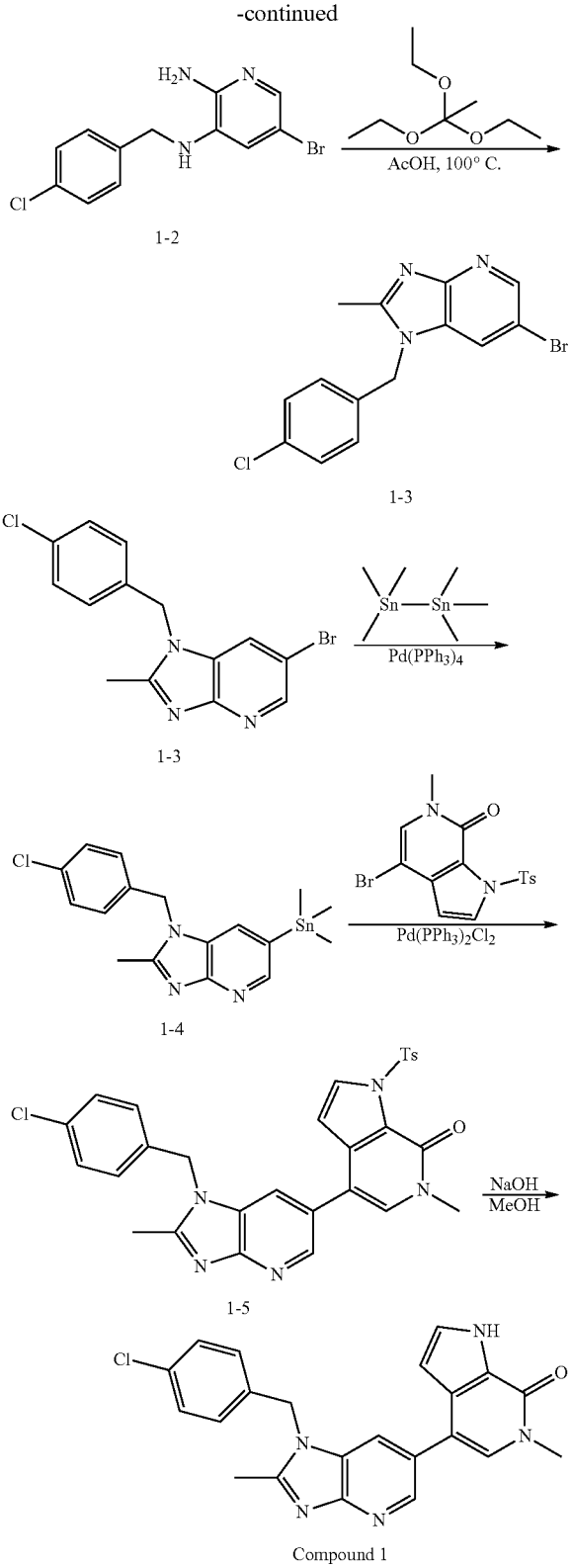

4 h. The reaction was monitored by TLC, concentrated, added with water (1 L), extracted three times with EA, the organic phases were combined, washed with water, dried over anhydrous sodium sulfate, and concentrated under reduced pressure to obtain 3.50 g crude compound 1M-11.

2. Synthesis of Compound 1M-12

Compound 1M-11 (3.50 g), iron powder (3.50 g) and ammonium chloride (3.50 g) were added to methanol (133 mL) and water (17.5 mL), the reaction was refluxed for 7 h, and the reaction was monitored by TLC to complete. Filter while hot, the cake was washed with methanol for two times while the filtrate was concentrated. Purified by column chromatography, PE:EA=5:1, to obtain 2.26 g crude compound 1M-12.

3. Synthesis of Compound 1M-13

Compound 1M-12 (2.26 g) was dissolved in THF (47 mL), protected by nitrogen, cooled to 0° C., added NaH (1.28 g), raised to room temperature for 1 h, cooled to 0° C., added TsCl solution (2.50 g TsCl dissolved in 47 mL THF), reacted for 2 h, TLC confirmed the reaction was completed, quenched by adding ice water. extracted three times with EA, the organic phases were combined, washed three times with saturated brine, dried over anhydrous sodium sulfate, and concentrated to obtain 3.80 g crude compound 1M-13.

4. Synthesis of Compound 1M-14

Compound 1M-13 (3.80 g) was dissolved in ethanol (10 mL), hydrogen bromide solution (40 mL, 40%) was added dropwise, the reaction was carried out at 90° C. for 2 h, TLC monitored the reaction was complete, cooled to 0° C., white solid precipitated, and filtered, the solid was collected, and the filter cake was washed twice with water and dried to obtain 3.60 g crude compound 1M-14.

5. Synthesis of Compound 1M-15

Compound 1M-14 (3.60 g) was dissolved in dioxane (50 mL), cesium carbonate (3.94 g) and iodomethane (5.40 g) were added, stirred at room temperature. The reaction was monitored by TLC to complete. The reaction solution was diluted with DCM (200 mL), washed three times with saturated brine, dried over anhydrous sodium sulfate, and concentrated. The crude product was slurried with a mixed solvent (20 mL) of n-Hex:EA=4:1 (V/V), and the solid was collected by filtration. The product was 3.20 g of light yellow solid.

6. Synthesis of Compound 1-1

2,3-diamino-5-bromopyridine (4.03 g) and p-chlorobenzaldehyde (3.00 g) was dissolved in DCM (350 mL), acetic acid (10 mL) was added, and stirred at room temperature overnight. After the reaction was monitored by TLC to complete, $Na_2CO_3$ solution (100 mL) was added, extracted twice with DCM, the organic phases were combined, dried over anhydrous sodium sulfate, concentrated, and purified by column chromatography PE:EA=100:15, to give a yellow solid as compound 1-1, 3.75 g.

7. Synthesis of Compound 1-2

Compound 1-1 (3.75 g) was dissolved in methanol, cooled in an ice bath, $NaBH_4$ (2.30 g) was added, and stirred at room temperature overnight. The reaction was monitored by TLC to complete, concentrated, 250 mL of water was added, extracted three times with EA, the organic phases were combined, dried over anhydrous sodium sulfate, and concentrated to obtain compound 1-2, 3.65 g.

8. Synthesis of Compound 1-3

Compound 1-2 (3.65 g) was dissolved in acetic acid (150 mL), triethyl orthoacetate (7.52 g) was added, and the temperature was raised to 100° C. for 2 h. The reaction was monitored by TLC to complete and concentrated. $Na_2CO_3$ solution (300 mL) was added, extracted twice with EA, the 1. Synthesis of Compound 1M-11

5-bromo-2-methoxy-4-methyl-3-nitropyridine (3.90 g) was dissolved in DMF (250 mL), warmed to 80° C., and was slowly added N,N-dimethylformamide dimethyl acetal (18 mL), after adding, the temperature was raised to 95° C. for organic phases were combined, dried over anhydrous sodium sulfate, and concentrated. The crude product was purified by column chromatography with PE:EA=1:1 (V/V), and the yellow solid was compound 1-3, 2.73 g.

9. Synthesis of Compound 1-4

Compound 1-3 (1.00 g), hexamethylditin (1.17 g) and tetrakis(triphenylphosphine)palladium (0.69 g) were dissolved in toluene (25 mL), replaced with nitrogen, heated at 115° C. for 2.5 h, cooled and concentrated, the crude product was purified by column chromatography, DCM:MeOH=100:2-100:3, to obtain a yellow solid, which is compound 1-4, 0.79 g.

10. Synthesis of Compound 1-5

Compound 1-4 (0.33 g), 1M-15 (0.30 g) and Pd(PPh$_3$)$_2$Cl$_2$ (0.06 mg) were dissolved in DMF (5 mL), protected by nitrogen, heated at 120° C. for 2 h, cooled and concentrated. The crude product was purified by column chromatography DCM:MeOH=100:3, to obtain a yellow solid, which is compound 1-5, 0.31 g.

11. Synthesis of Compound 1

Compound 1-5 (0.31 g) was dissolved in MeOH (10 mL) and DCM (5 mL), NaOH (0.30 g) was added, stirred at room temperature overnight, the reaction was monitored by TLC, concentrated, the crude product was purified by column chromatography DCM:MeOH=100:2, to obtain a white solid, which is compound 1, 0.13 g.

LCMS: [M+1]$^+$=404.2.

$^1$HNMR (400 MHz, DMSO) δ 12.17 (s, 1H), 8.55 (d, J=1.4 Hz, 1H), 8.04 (d, J=1.3 Hz, 1H), 7.59-7.37 (m, 3H), 7.34 (s, 1H), 7.21 (d, J=8.2 Hz, 2H), 6.29 (s, 1H), 5.58 (s, 2H), 3.58 (s, 3H), 2.59 (s, 3H).

Using a method basically similar to that of Example 1, the corresponding p-chlorobenzaldehyde derivative is used to replace

(p-chlorobenzaldehyde) in the example to prepare the example in Table 4 below. The corresponding p-benzaldehyde derivatives, such as

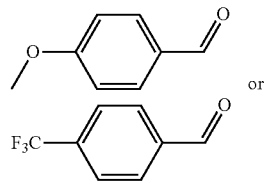

etc, can all be purchased through commercially available channels. The corresponding iodomethane derivatives, for example

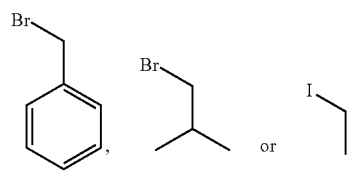

can also be purchased through commercially available channels.

TABLE 4

| Example | Structure | Chemical Name | Physical data (MS) (M + H)$^+$ |
|---|---|---|---|
| 1 | ![structure] | 4-(1-(4-chlorobenzyl)-2-methyl-1H-imidazo[4,5-b]pyridin-6-yl)-6-methyl-1H-pyrrolo[2,3-c]pyridin-7(6H)-one | 404.2 |
| 2 | ![structure] | 4-(1-(4-methoxybenzyl)-2-methyl-1H-imidazo[4,5-b]pyridin-6-yl)-6-methyl-1H-pyrrolo[2,3-c]pyridin-7(6H)-one | 400.2 |
| 3 | ![structure] | 6-methyl-4-(2-methyl-1-(4-methylthio)benzyl)-1H-imidazo[4,5-b]pyridin-6-yl)-1H-pyrrolo[2,3-c]pyridin-7(6H)-one | 416.2 |

TABLE 4-continued

| Example | Structure | Chemical Name | Physical data (MS) (M + H)+ |
|---|---|---|---|
| 4 | 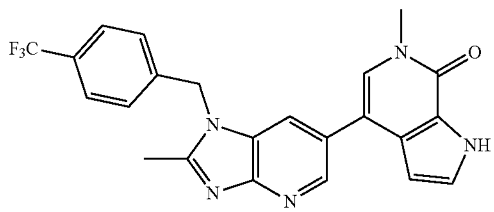 [SMILES: Cc1nc2ncc(-c3cn(C)c(=O)c4[nH]ccc34)cc2n1Cc1ccc(C(F)(F)F)cc1] | 6-methyl-4-(2-methyl-1-(4-(trifluoromethyl)benzyl)-1H-imidazo[4,5-b]pyridin-6-yl)-1H-pyrrolo[2,3-c]pyridin-7(6H)-one | 438.2 |
| 5 | 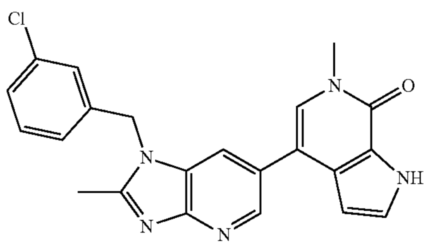 | 4-(1-(3-chlorobenzyl)-2-methyl-1H-imidazo[4,5-b]pyridin-6-yl)-6-methyl-1H-pyrrolo[2,3-c]pyridin-7(6H)-one | 405.1 |
| 6 | 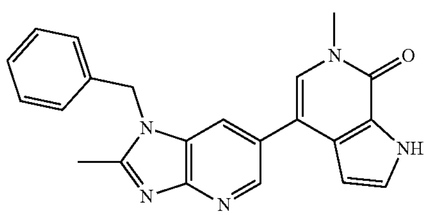 [SMILES: Cc1nc2ncc(-c3cn(C)c(=O)c4[nH]ccc34)cc2n1Cc1ccccc1] | 4-(1-benzyl-2-methyl-1H-imidazo[4,5-b]pyridin-6-yl)-6-methyl-1H-pyrrolo[2,3-c]pyridin-7(6H)-one | 370.2 |
| 7 | 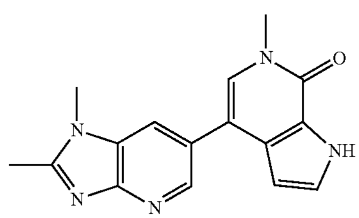 [SMILES: Cc1nc2ncc(-c3cn(C)c(=O)c4[nH]ccc34)cc2n1C] | 4-(1,2-dimethyl-1H-imidazo[4,5-b]pyridin-6-yl)-6-methyl-1,6-dihydro-7H-pyrrolo[2,3-c]pyridin-7-one | 294.1 |
| 8 | 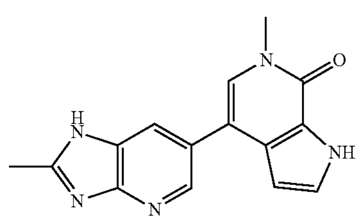 [SMILES: Cc1nc2ncc(-c3cn(C)c(=O)c4[nH]ccc34)cc2[nH]1] | 6-methyl-4-(2-methyl-1H-imidazo[4,5-b]pyridin-6-yl)-1,6-dihydro-7H-pyrrolo[2,3-c]pyridin-7-one | 280.1 |
| 9 | 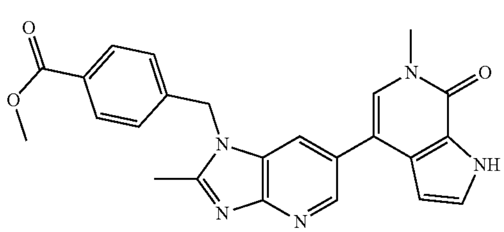 [SMILES: COC(=O)c1ccc(Cn2c(C)nc3ncc(-c4cn(C)c(=O)c5[nH]ccc45)cc32)cc1] | methyl 4-((2-methyl-6-(6-methyl-7-oxo-6,7-dihydro-1H-pyrrolo[2,3-c]pyridin-4-yl)-1H-imidazo[4,5-b]pyridin-1-yl)methyl)benzoate | 428.2 |

TABLE 4-continued

| Example | Structure | Chemical Name | Physical data (MS) (M + H)+ |
|---|---|---|---|
| 10 | 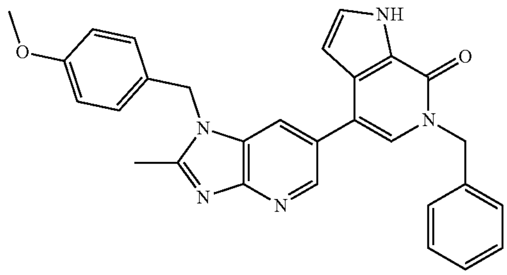 [SMILES: COc1ccc(Cn2c(C)nc3ncc(-c4cn(Cc5ccccc5)c(=O)c5[nH]ccc45)cc32)cc1] | 6-benzyl-4-(1-(4-methoxybenzyl)-2-methyl-1H-imidazo[4,5-b]pyridin-6-yl)-1,6-dihydro-7H-pyrrolo[2,3-c]pyridin-7-one | 476.2 |
| 11 | 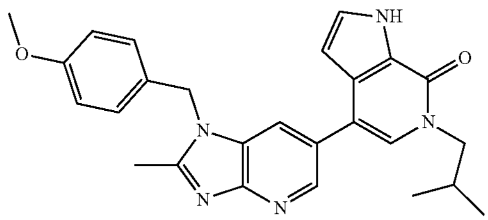 [SMILES: COc1ccc(Cn2c(C)nc3ncc(-c4cn(CC(C)C)c(=O)c5[nH]ccc45)cc32)cc1] | 6-isobutyl-4-(1-(4-methoxybenzyl)-2-methyl-1H-imidazo[4,5-b]pyridin-6-yl)-1,6-dihydro-7H-pyrrolo[2,3-c]pyridin-7-one | 442.2 |
| 12 | 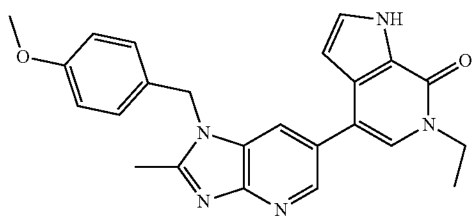 [SMILES: CCn1cc(-c2cnc3nc(C)n(Cc4ccc(OC)cc4)c3c2)c2cc[nH]c2c1=O] | 6-ethyl-4-(1-(4-methoxybenzyl)-2-methyl-1H-imidazo[4,5-b]pyridin-6-yl)-1,6-dihydro-7H-pyrrolo[2,3-c]pyridin-7-one | 414.5 |
| 13 | 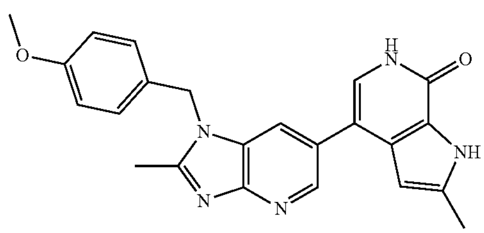 [SMILES: COc1ccc(Cn2c(C)nc3ncc(-c4c[nH]c(=O)c5[nH]c(C)cc45)cc32)cc1] | 4-(1-(4-methoxybenzyl)-2-methyl-1H-imidazo[4,5-b]pyridin-6-yl)-2-methyl-1,6-dihydro-7H-pyrrolo[2,3-c]pyridin-7-one | 400.2 |
| 14 | 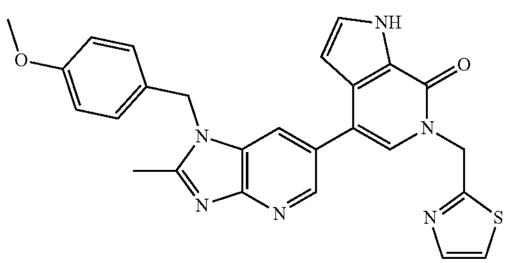 [SMILES: COc1ccc(Cn2c(C)nc3ncc(-c4cn(Cc5nccs5)c(=O)c5[nH]ccc45)cc32)cc1] | 4-(1-(4-methoxybenzyl)-2-methyl-1H-imidazo[4,5-b]pyridin-6-yl)-6-(thiazol-2-ylmethyl)-1,6-dihydro-7H-pyrrolo[2,3-c]pyridin-7-one | 483.5 |
| 15 | 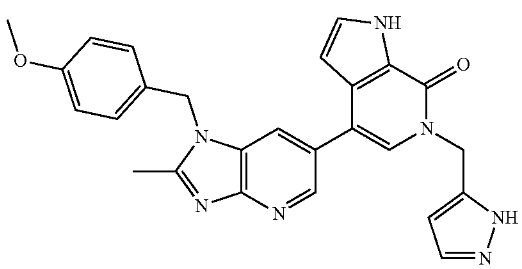 [SMILES: COc1ccc(Cn2c(C)nc3ncc(-c4cn(Cc5ccn[nH]5)c(=O)c5[nH]ccc45)cc32)cc1] | 4-(1-(4-methoxybenzyl)-2-methyl-1H-imidazo[4,5-b]pyridin-6-yl)-6-(pyrazol-2-methyl)-1,6-dihydro-7H-pyrrolo[2,3-c]pyridin-7-one | 466.5 |

TABLE 4-continued

| Example | Structure | Chemical Name | Physical data (MS) (M + H)+ |
|---|---|---|---|
| 16 | 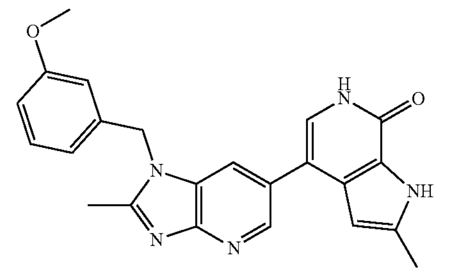 [SMILES: COc1cccc(Cn2c(C)nc3ncc(-c4c[nH]c(=O)c5[nH]c(C)cc45)cc32)c1] | 4-(1-(3-methoxybenzyl)-2-methyl-1H-imidazo[4,5-b]pyridin-6-yl)-2-methyl-1,6-dihydro-7H-pyrrolo[2,3-c]pyridin-7-one | 400.2 |
| 17 | 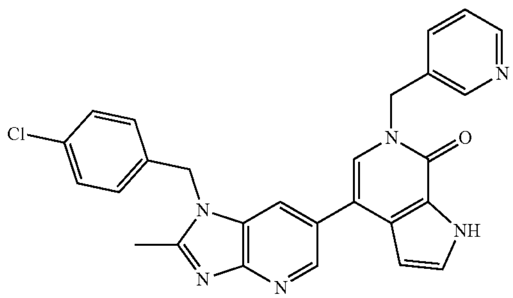 [SMILES: Cc1nc2ncc(-c3cn(Cc4cccnc4)c(=O)c4[nH]ccc34)cc2n1Cc1ccc(Cl)cc1] | 4-(1-(4-chlorobenzyl)-2-methyl-1H-imidazo[4,5-b]pyridin-6-yl)-6-(pyridin-3-ylmethyl)-1,6-dihydro-7H-pyrrolo[2,3-c]pyridin-7-one | 481.1 |

Example 18: Synthesis of Compound 18 (4-(1-(4-chlorobenzyl)-2-methyl-1H-imidazo[4,5-b]pyrazin-6-yl)-6-methyl-1H-pyrrolo[2,3-c]pyridin-7(6H)-one)

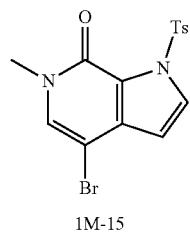

1M-15

KAcO/(BPin)$_2$
—————————→
XPhos/Pd$_2$(dba)$_3$

-continued

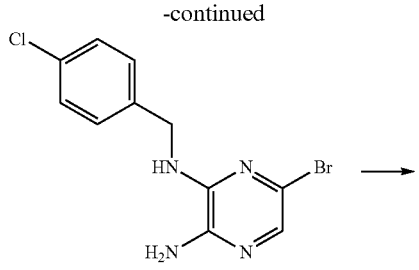

18-1

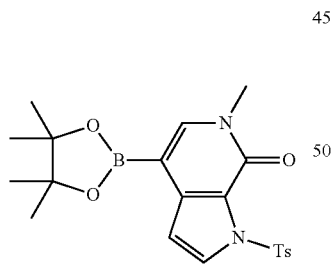

2M-1

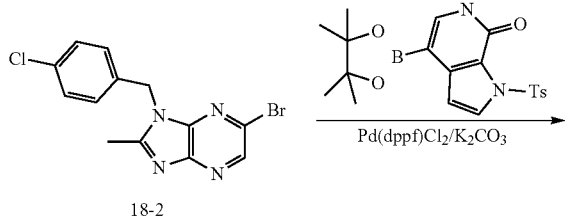

18-2

Pd(dppf)Cl$_2$/K$_2$CO$_3$
—————————→

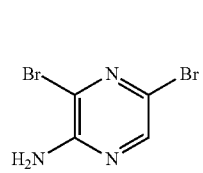

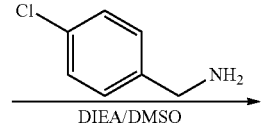

DIEA/DMSO
—————————→

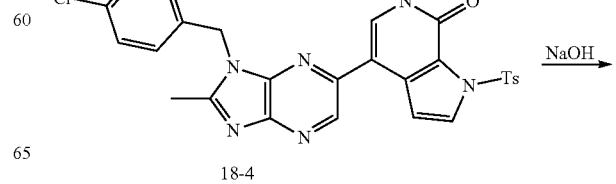

18-4

NaOH
——→

-continued

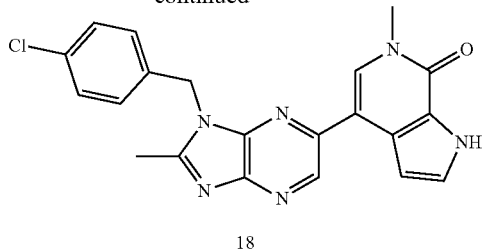

18

1. Synthesis of Compound 2M-1

Compound 1M-15(6.00 g), (BPin)$_2$(8.00 g), XPhos (0.90 g), Pd$_2$(dba)$_3$(0.43 g) and KAcO (3.40 g) were dissolved in dioxane (90 mL), protected by nitrogen, stirred reaction at 80° C. for 4 h. Cooled, the reaction solution was poured into a mixed solvent of EA (200 mL) and saturated Na$_2$CO$_3$ (200 mL), separated the liquid, aqueous phase was extracted 3 times with EA, combined the organic phases, washed with saturated brine 3 times, dried over anhydrous sodium sulfate, and concentrated. The crude product was purified by column chromatography with PE:EA=100:30, to obtain a white solid, which is compound 2M-1, 3.45 g.

2. Synthesis of Compound 18-1

2-amino-3,5-dibromopyrazine (10.00 g), 4-chlorobenzylamine (16.90 g) and DIEA (25.54 g) was dissolved in DMSO (40 mL), heated and stirred at 120° C. for 4 h, LCMS confirmed the end of the reaction. Cooled, cold water (200 mL) was added, extracted 3 times with EA, combined organic phases, washed with saturated brine 3 times, dried with anhydrous sodium sulfate, concentrated, and purified the crude product by column chromatography with PE:EA=100:15-100:30, to obtain a yellow solid, which is compound 18-1, 13.91 g.

3. Synthesis of Compound 18-2

Compound 18-1 (13.90 g), triethyl orthoacetate (35.96 g) and glacial acetic acid (200 mL) were mixed and reacted at 100° C. overnight. Cooled, concentrated, diluted the crude product with EA, wash 3 times with saturated Na$_2$CO$_3$ solution, 3 times with saturated brine, dried over anhydrous sodium sulfate, and concentrated. The crude product was purified by column chromatography with PE:EA=100:20-100:50, to obtain a yellow solid, which is compound 18-2, 12.05 g.

4. Synthesis of Compound 18-4

Compound 18-2 (1.00 g), 2M-1(1.27 g), Pd(dppf)Cl$_2$.DCM (0.25 g) were dissolved in dioxane (20 mL), K$_2$CO$_3$ (0.61 g) and water (4 mL) were added, protected by nitrogen, heated and stirred at 100° C. overnight. Cooled, the reaction solution was poured into a mixed solvent of EA (50 mL) and saturated Na$_2$CO$_3$ (50 mL), separated the liquid, aqueous phase was extracted 3 times with EA, organic phases were combined, washed with saturated brine 3 times, dried over anhydrous sodium sulfate, and concentrated, the crude product was purified by column chromatography with DCM:MeOH=100:2, to obtain a yellow solid, which is compound 18-4, 0.95 g.

5. Synthesis of Compound 18

Compound 18-4 (0.95 g) was dissolved in MeOH (10 mL) and DCM (20 mL), NaOH (0.40 g) was added, stirred at room temperature overnight, concentrated. The crude product was dissolved in 10 mL DMF, which was dropped into saturated ammonium chloride solution (100 mL), the solid was collected by filtration, the crude product was slurried with EA (10 mL), the solid was collected by filtration, and dried under reduced pressure to give compound 18 as a light brown solid, 0.51 g.

LCMS: [M+1]+=405.8.

$^1$HNMR (400 MHz, DMSO) δ 12.15 (s, 1H), 8.93 (s, 1H), 8.04 (s, 1H), 7.58-7.13 (m, 5H), 6.86 (t, J=2.3 Hz, 1H), 5.58 (s, 2H), 3.64 (s, 3H), 2.62 (s, 3H).

Using a method basically similar to that of Example 18, the corresponding p-chlorobenzylamine derivative is used to replace

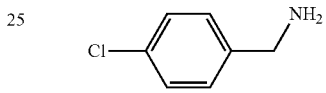

(p-chlorobenzylamine) to prepare the example in Table 5 below. The corresponding p-chlorobenzylamine derivative, such

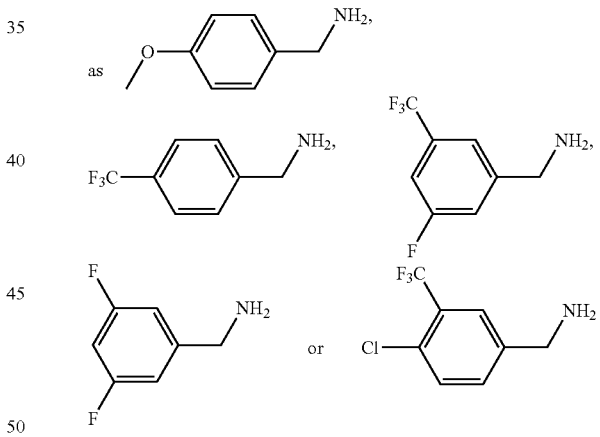

etc, can all be purchased through commercially available channels.

TABLE 5

| Example | Structure | Chemical Name | Physical data (MS) (M + H)+ |
|---|---|---|---|
| 18 | 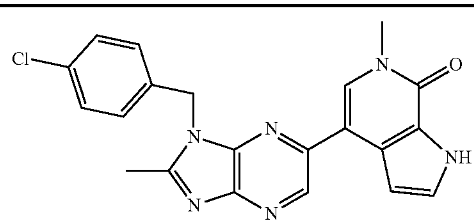 | 4-(1-(4-chlorobenzyl)-2-methyl-1H-imidazo[4,5-b]pyrazin-6-yl)-6-methyl-1H-pyrrolo[2,3-c]pyridin-7(6H)-one | 405.8 |

TABLE 5-continued

| Example | Structure | Chemical Name | Physical data (MS) (M + H)+ |
|---|---|---|---|
| 19 | 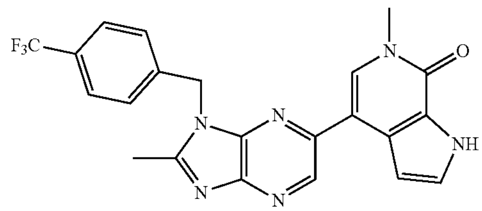 [SMILES: Cc1nc2ncc(-c3cn(C)c(=O)c4[nH]ccc34)nc2n1Cc1ccc(C(F)(F)F)cc1] | 6-methyl-4-(2-methyl-1-(4-(trifluoromethyl)benzyl)-1H-imidazo[4,5-b]pyrazin-6-yl)-1H-pyrrolo[2,3-c]pyridin-7(6H)-one | 439.1 |
| 20 | 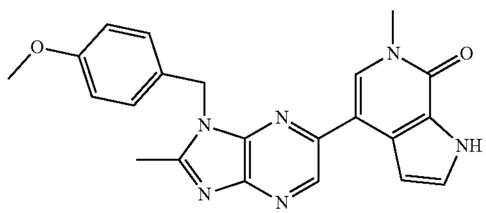 [SMILES: COc1ccc(Cn2c(C)nc3ncc(-c4cn(C)c(=O)c5[nH]ccc45)nc32)cc1] | 4-(1-(4-methoxybenzyl)-2-methyl-1H-imidazo[4,5-b]pyrazin-6-yl)-6-methyl-1H-pyrrolo[2,3-c]pyridin-7(6H)-one | 401.2 |
| 21 | 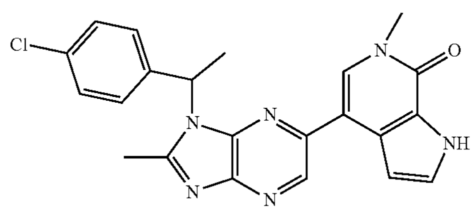 [SMILES: Cc1nc2ncc(-c3cn(C)c(=O)c4[nH]ccc34)nc2n1C(C)c1ccc(Cl)cc1] | 4-(1-(1-(4-chlorophenyl)ethyl)-2-methyl-1H-imidazo[4,5-b]pyrazin-6-yl)-6-methyl-1,6-dihydro-7H-pyrrolo[2,3-c]pyridin-7-one | 419.1 |
| 22 | 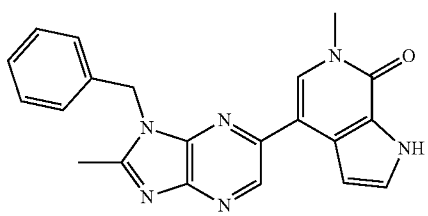 [SMILES: Cc1nc2ncc(-c3cn(C)c(=O)c4[nH]ccc34)nc2n1Cc1ccccc1] | 4-(1-benzyl-2-methyl-1H-imidazo[4,5-b]pyrazin-6-yl)-6-methyl-1H-pyrrolo[2,3-c]pyridin-7(6H)-one | 371.1 |
| 23 | 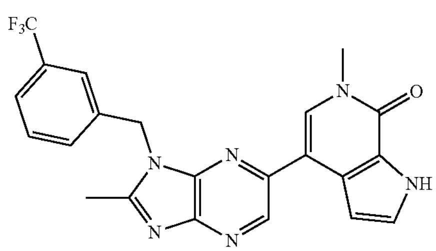 [SMILES: Cc1nc2ncc(-c3cn(C)c(=O)c4[nH]ccc34)nc2n1Cc1cccc(C(F)(F)F)c1] | 4-(1-(3-trifluoromethylbenzyl)-2-methyl-1H-imidazo[4,5-b]pyrazin-6-yl)-6-methyl-1H-pyrrolo[2,3-c]pyridin-7(6H)-one | 439.1 |
| 24 | 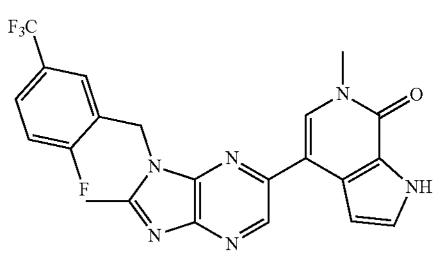 [SMILES: Cc1nc2ncc(-c3cn(C)c(=O)c4[nH]ccc34)nc2n1Cc1cc(C(F)(F)F)ccc1F] | 4-(1-(2-fluoro-5-trifluoromethyl-benzyl)-2-methyl-1H-imidazo[4,5-b]pyrazin-6-yl)-6-methyl-1H-pyrrolo[2,3-c]pyridin-7(6H)-one | 457.1 |

TABLE 5-continued

| Example | Structure | Chemical Name | Physical data (MS) (M + H)+ |
|---|---|---|---|
| 25 | 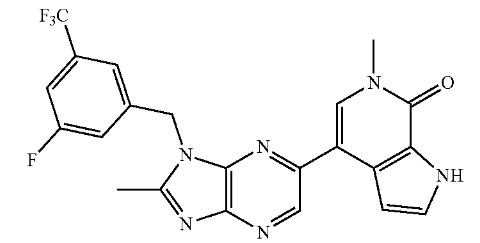 [SMILES: Cc1nc2ncc(-c3cn(C)c(=O)c4[nH]ccc34)nc2n1Cc1cc(F)cc(C(F)(F)F)c1] | 4-(1-(3-fluoro-5-trifluoromethyl-benzyl)-2-methyl-1H-imidazo[4,5-b]pyrazin-6-yl)-6-methyl-1H-pyrrolo[2,3-c]pyridin-7(6H)-one | 457.1 |
| 26 | 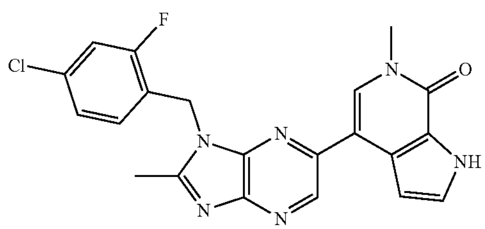 [SMILES: Cc1nc2ncc(-c3cn(C)c(=O)c4[nH]ccc34)nc2n1Cc1ccc(Cl)cc1F] | 4-(1-(2-fluoro-4-chlorobenzyl)-2-methyl-1H-imidazo[4,5-b]pyrazin-6-yl)-6-methyl-1H-pyrrolo[2,3-c]pyridin-7(6H)-one | 423.1 |
| 27 | 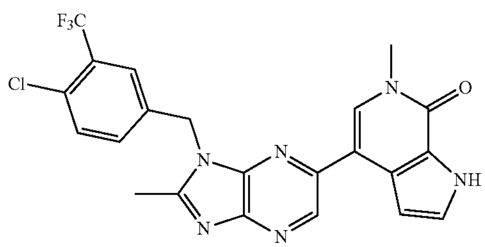 [SMILES: Cc1nc2ncc(-c3cn(C)c(=O)c4[nH]ccc34)nc2n1Cc1ccc(Cl)c(C(F)(F)F)c1] | 4-(1-(3-trifluoromethyl-4-chlorobenzyl)-2-methyl-1H-imidazo[4,5-b]pyrazin-6-yl)-6-methyl-1H-pyrrolo[2,3-c]pyridin-7(6H)-one | 473.1 |
| 28 | 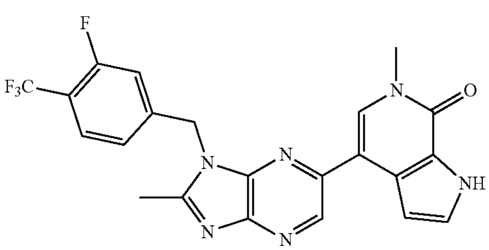 [SMILES: Cc1nc2ncc(-c3cn(C)c(=O)c4[nH]ccc34)nc2n1Cc1ccc(C(F)(F)F)c(F)c1] | 4-(1-(3-fluoro-4-trifluoromethyl-benzyl)-2-methyl-1H-imidazo[4,5-b]pyrazin-6-yl)-6-methyl-1H-pyrrolo[2,3-c]pyridin-7(6H)-one | 457.1 |
| 29 | 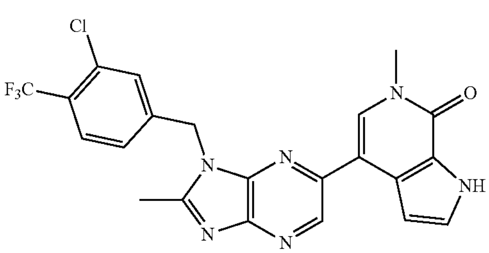 [SMILES: Cc1nc2ncc(-c3cn(C)c(=O)c4[nH]ccc34)nc2n1Cc1ccc(C(F)(F)F)c(Cl)c1] | 4-(1-(3-chloro-4-trifluoro-methylbenzyl)-2-methyl-1H-imidazo[4,5-b]pyrazin-6-yl)-6-methyl-1H-pyrrolo[2,3-c]pyridin-7(6H)-one | 473.1 |
| 30 | 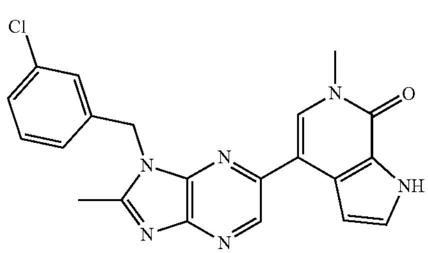 [SMILES: Cc1nc2ncc(-c3cn(C)c(=O)c4[nH]ccc34)nc2n1Cc1cccc(Cl)c1] | 4-(1-(3-chlorobenzyl)-2-methyl-1H-imidazo[4,5-b]pyrazin-6-yl)-6-methyl-1H-pyrrolo[2,3-c]pyridin-7(6H)-one | 405.1 |

TABLE 5-continued

| Example | Structure | Chemical Name | Physical data (MS) (M + H)+ |
|---------|-----------|---------------|------------------------------|
| 31 | 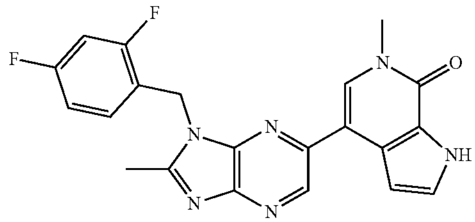 [SMILES: Cc1nc2ncc(-c3cn(C)c(=O)c4[nH]ccc34)nc2n1Cc1ccc(F)cc1F] | 4-(1-(2,4-difluorobenzyl)-2-methyl-1H-imidazo[4,5-b]pyrazin-6-yl)-6-methyl-1H-pyrrolo[2,3-c]pyridin-7(6H)-one | 407.1 |
| 32 | 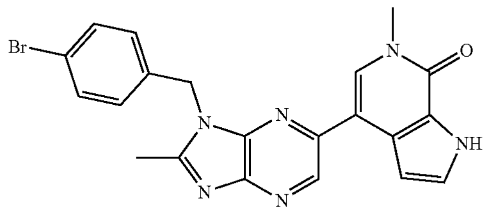 | 4-(1-(4-bromobenzyl)-2-methyl-1H-imidazo[4,5-b]pyrazin-6-yl)-6-methyl-1H-pyrrolo[2,3-c]pyridin-7(6H)-one | 449.06 |
| 33 | 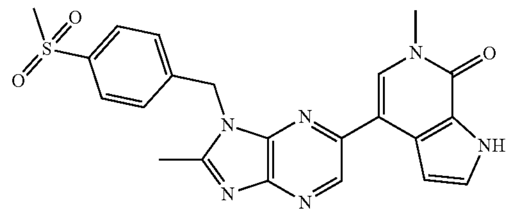 [SMILES: Cc1nc2ncc(-c3cn(C)c(=O)c4[nH]ccc34)nc2n1Cc1ccc(S(C)(=O)=O)cc1] | 6-methyl-4-(2-methyl-1-(4-(methylsulfonyl)benzyl)-1H-imidazo[4,5-b]pyrazin-6-yl)-1H-pyrrolo[2,3-c]pyridin-7(6H)-one | 449.1 |

Example 34 Synthesis of Compound 34 (1-(4-chlorobenzyl)-6-(6-methyl-7-oxo-6,7-dihydro-1H-pyrrolo[2,3-c]pyridin-4-yl)-1,3-dihydro-2H-imidazo[4,5-b]pyridin-2-one)

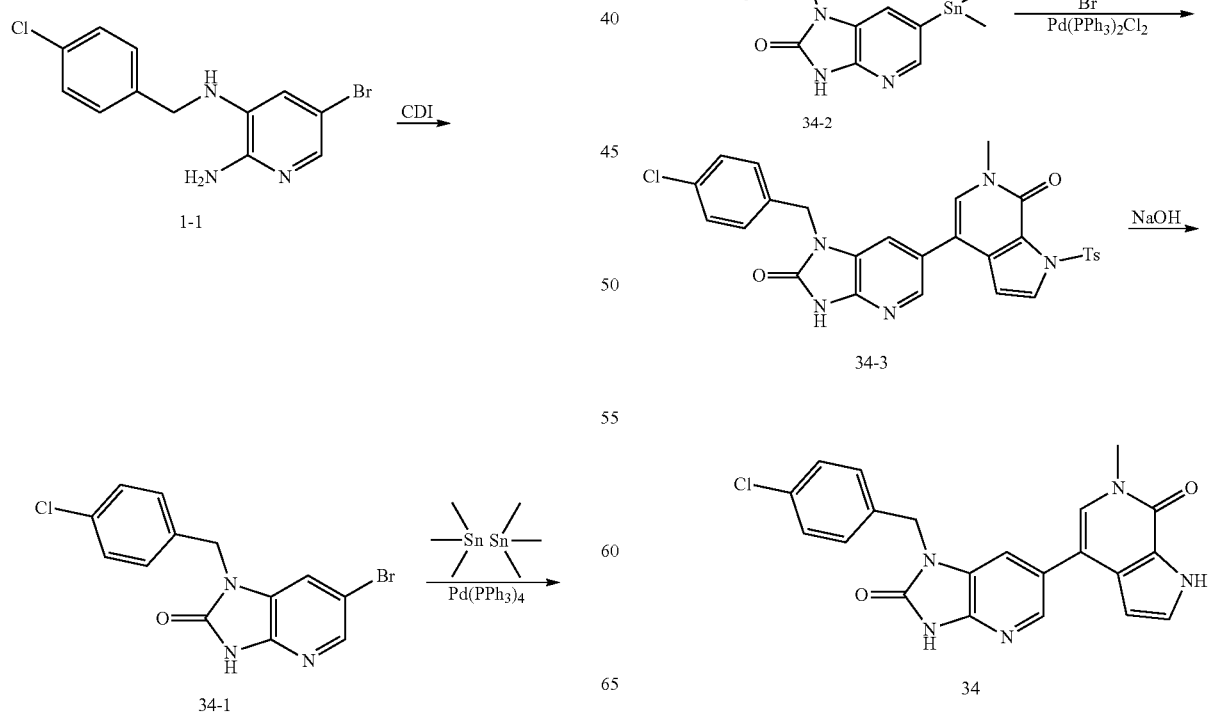

1. Synthesis of Compound 34-1

Compound 1-1 (4.43 g) was dissolved in CH₃CN (25 mL), CDI (11.51 g) was added, and stirred at room temperature overnight. The solid was collected by suction filtration, and the filter cake was washed with n-hexane and dried to give a white solid as compound 34-1, 4.24 g.

2. Synthesis of Compound 34-2

Compound 34-1 (1.00 g), hexamethylditin (1.16 g) and tetrakis (triphenylphosphine) palladium (0.68 g) were dissolved in 1,4-dioxane (25 mL), protected by nitrogen, stirred overnight at 100° C. After cooling and concentration, the crude product was purified by column chromatography with PE:EA=100:25, and the off-white solid was obtained as compound 34-2, 1.23 g.

3. Synthesis of Compound 34-3

Compound 34-2 (0.35 g), compound 34-5 (0.31 g) and Pd(PPh₃)₂Cl₂(0.06 g) was added to DMF (5 mL) and dioxane (2.5 mL), under nitrogen protection, reacted overnight at 100° C. After cooling, water (50 mL) was added, and the mixture was extracted with DCM 3 times, the organic phases were combined, concentrated, purified by column chromatography with DCM:MeOH=100:3, and off-white solid was obtained as compound 34-3, 0.13 g.

4. Synthesis of Compound 34

Compound 34-3 (0.21 g) was dissolved in MeOH (50 mL), NaOH (0.20 g) was added, and the mixture was stirred overnight at room temperature. Water (500 mL) and DCM (500 mL) were added to the system. The solid was collected by filtration. The filter cake was dissolved with MeOH:DCM=1:1, the organic phases were combined and concentrated to obtain compound 34, 0.06 g.

LCMS: [M+1]⁺=406.1.

¹HNMR: (400 MHz, DMSO) δ 12.12 (s, 1H), 8.23-6.38 (m, 9H), 6.22 (t, J=2.8 Hz, 1H), 5.05 (s, 2H), 3.64 (s, 3H).

Example 35 Synthesis of Compound 35 (4-(3-(1-(2, 6-dichloro-3-fluorophenyl)ethyl)-2-methyl-1H-pyrrolo[2,3-b]pyridin-5-yl)-6-methyl-1,6-dihydro-7H-pyrrolo[2,3-c]pyridin-7-one)

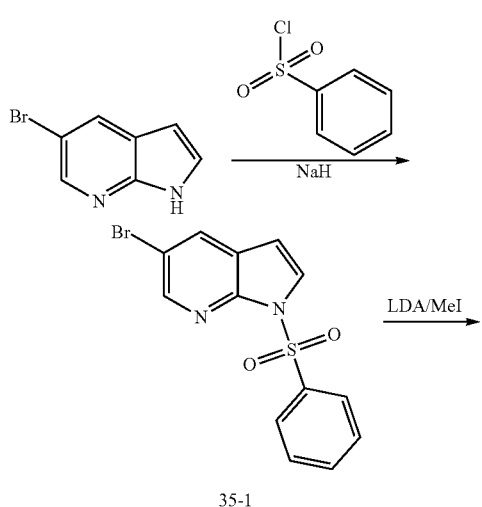

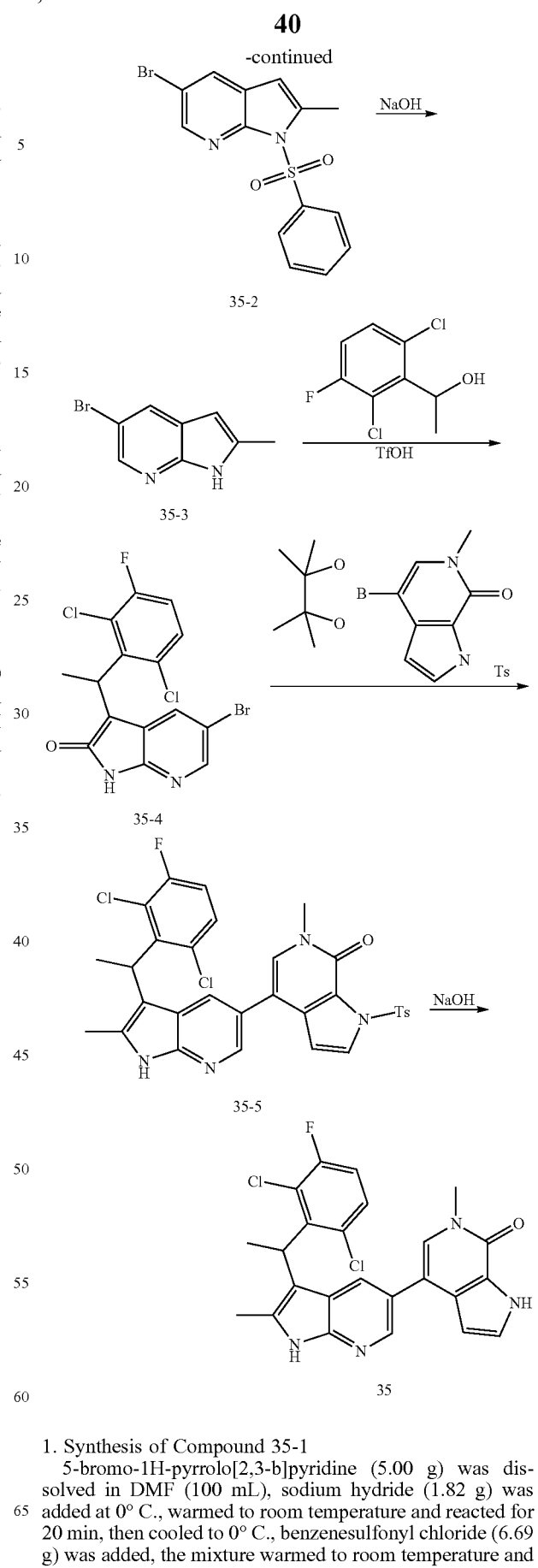

1. Synthesis of Compound 35-1

5-bromo-1H-pyrrolo[2,3-b]pyridine (5.00 g) was dissolved in DMF (100 mL), sodium hydride (1.82 g) was added at 0° C., warmed to room temperature and reacted for 20 min, then cooled to 0° C., benzenesulfonyl chloride (6.69 g) was added, the mixture warmed to room temperature and reacted for 1 h. Quenched with 100 mL of saturated ammonium chloride solution, extracted three times with DCM, the organic phases were combined, washed with saturated brine twice, dried over anhydrous sodium sulfate, and concentrated to obtain 8.37 g of crude product.

2. Synthesis of Compound 35-2

2-isopropylamine (4.20 g) was dissolved in THF (100 mL), protected by nitrogen, the temperature was lowered to −78° C., then n-butyllithium (16 mL) was added, reacted at low temperature for 60 min, and compound 35-1 (5.00 g) in THF (30 mL) was added, reacted at −78° C. for 60 min, added methyl iodide (6.31 g), warmed to room temperature and reacted for 2 h. Saturated ammonium chloride solution (50 mL) was added to quench the reaction, concentrated, extracted three times with EA, the organic phases were combined, washed with saturated brine, dried over anhydrous sodium sulfate, and purified by column chromatography with PE:EA=100:40, to obtain 4.52 g product as white solid.

3. Synthesis of Compound 35-3

Compound 35-2 (4.52 g) was dissolved in methanol (100 mL), sodium hydroxide (4.52 g) was added, and stirred at room temperature overnight. Saturated ammonium chloride solution (50 mL) was added, concentrated, and extracted twice with EA. The organic phases were combined, washed twice with saturated brine, dried over anhydrous sodium sulfate, and concentrated to obtain 2.80 g of crude product.

4. Synthesis of Compound 35-4

Compound 35-3 (2.80 g) was dissolved in DCM (65 mL), protected by nitrogen, trifluoromethanesulfonic acid (7.96 g) was added, and 1-(2,6-dichloro-3-fluorophenyl)-ethanol (11.09 g) in DCM (20 mL) was added, reacted at room temperature overnight. Then reacted at 35° C. for 4 h, saturated sodium carbonate solution (200 mL) was added, extract 3 times with DCM (500 mL), washed twice with saturated brine, dried over anhydrous sodium sulfate, concentrated, the crude product was slurried with EA (50 mL), the product is obtained as white solid, 2.40 g.

5. Synthesis of Compound 35-5

Compound 35-4 (0.10 g), 2M-1 (0.11 g) and Pd(dppf)Cl$_2$ (0.02 g) were dissolved in DMF (2 mL), potassium carbonate (0.07 g) was added, nitrogen protection, reacted at 115° C. overnight. Cooled, filtered, the filtrate was added with water (10 mL), extracted three times with DCM (10 mL), washed three times with saturated brine (10 mL), and directly concentrated to obtain 0.21 g of brown oil, which was directly used in the next reaction.

6. Synthesis of Compound 35

Compound 35-5 (0.21 g) was dissolved in methanol (10 mL), sodium hydroxide (0.10 g) was added, stirred at 40° C. for 4 h, added saturated ammonium chloride solution (10 mL), extracted twice with DCM (50 mL), washed twice with saturated brine, the organic phase was concentrated, and purified by column chromatography with DCM:MeOH=100:5 to obtain 0.07 g of product.

LCMS: [M+1]+=469.1.

$^1$HNMR: (400 MHz, DMSO) δ 12.12 (s, 1H), 11.42 (s, 1H), 8.24 (d, J=1.9 Hz, 1H), 7.83 (d, J=1.7 Hz, 1H), 7.50 (dd, J=8.9, 5.1 Hz, 1H), 7.44-7.13 (m, 3H), 6.22-5.96 (m, 1H), 5.22 (q, J=7.2 Hz, 1H), 3.58 (s, 3H), 2.30 (s, 3H), 1.87 (d, J=7.5 Hz, 3H).

Example 36 Synthesis of Compound 36 (4-(1-(2,6-dichlorobenzyl)-1H-pyrrolo[3,2-b]pyridin-6-yl)-6-methyl-1,6-dihydro-7H-pyrrolo[2,3-c]pyridin-7-one)

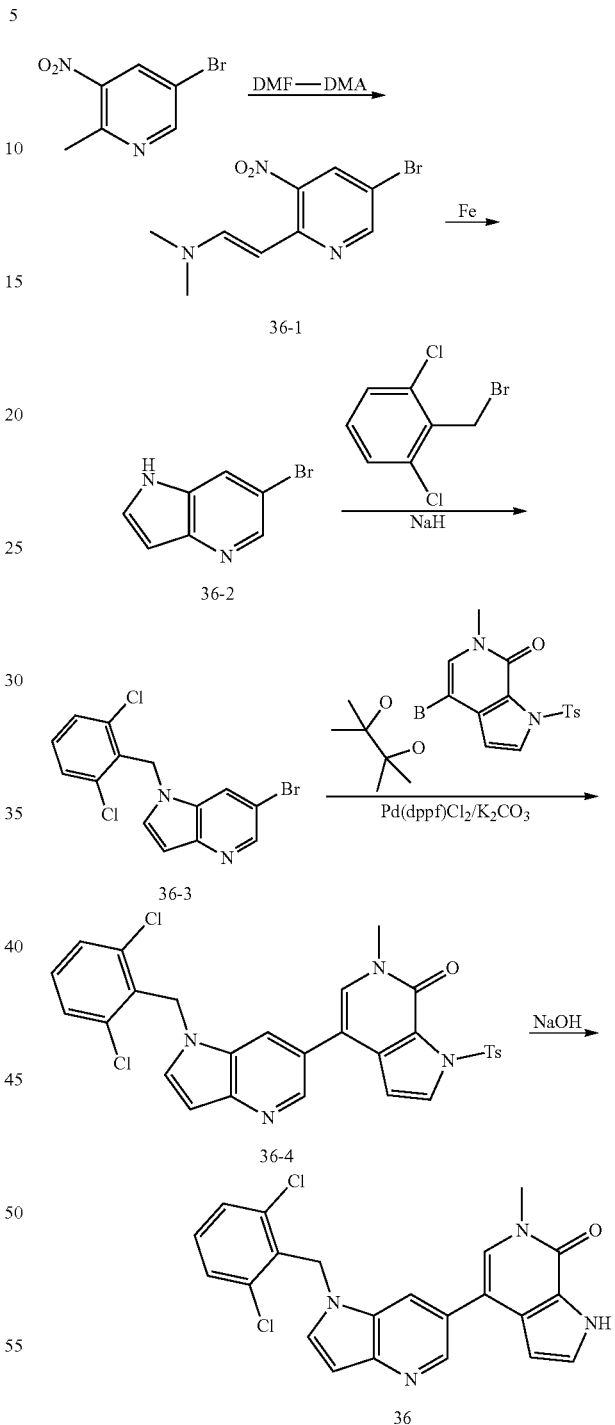

1. Synthesis of Compound 36-1

5-bromo-2-methyl-3-nitropyrimidine (1.00 g) was dissolved in DMF (10 mL), added N, N-dimethylformamide dimethyl acetal (5 mL), and reacted at 100° C. for 1 h, cooled, quenched with saturated ammonium chloride solution (25 mL), then extracted twice with EA (25 mL), the organic phases were combined, washed with saturated brine, dried over anhydrous sodium sulfate, and concentrated to obtain 1.45 g of crude product, which was directly used for the next reaction.

2. Synthesis of Compound 36-2

Compound 36-1 (1.45 g) and iron powder (2.38 g) were added to glacial acetic acid (50 mL), raised the temperature to 80° C. and reacted for 5 h, filtered while hot, the filter cake was washed with EA, the filtrate was combined, concentrated, and saturated Na$_2$CO$_3$ solution was added, After filtering again, the filter cake was washed with EA, the filtrate was separated, and the organic phase was washed with saturated brine, dried over anhydrous sodium sulfate, and concentrated. The crude product was purified by column chromatography with PE:EA=100:50 to obtain 0.73 g of product.

3. Synthesis of Compound 36-3

Compound 36-2 (0.70 g) was dissolved in DMF (25 mL), protected by nitrogen, sodium hydride (0.19 g) was added at 0° C., and the temperature was naturally raised to room temperature and stirred for 1 h. Added 2,6-dichlorobenzyl bromide (0.85 g) at 0° C., naturally rised to room temperature and reacted for 3 h. 50 mL of ice-water mixture was added to quench the reaction, extracted with EA 3 times, the organic phases were combined, washed with saturated brine 3 times, dried over anhydrous sodium sulfate, concentrated, to obtain the yellow solid 1.30 g.

4. Synthesis of Compound 36-4

Compound 36-3 (0.40 g), compound 2M-1 (0.48 g) and Pd(dppf)Cl$_2$.DCM (0.10 g) were dissolved in dioxane (8 mL), potassium carbonate (0.23 g) in water (1.5 mL) was added, protected by nitrogen, and stirred at 100° C. overnight. Cooled, a mixed solution of EA (50 mL) and saturated Na$_2$CO$_3$ (50 mL) was added, collect the organic phase, extracted the aqueous phase 3 times with EA, the organic phases were combined, washed with saturated brine 3 times, dried over anhydrous sodium sulfate, concentrated, and the crude product was purified by column chromatography with DCM:MeOH=100:2, to obtain 0.50 g of brown solid.

5. Synthesis of Compound 36

Compound 36-4 (0.50 g) was dissolved in a mixed solution of MeOH/DCM=10 mL:10 mL, sodium hydroxide (0.30 g) was added, and stirred at room temperature overnight. After concentration, the crude product was purified by column chromatography with DCM:MeOH=100:5 to obtain 0.21 g of light brown solid.

LCMS: [M+1]+=423.1.

$^1$HNMR: (400 MHz, DMSO) δ 12.17 (s, 1H), 7.69-7.55 (m, 2H), 7.52-7.23 (m, 6H), 6.62 (dd, J=3.3, 0.7 Hz, 1H), 6.30 (dd, J=2.6, 2.1 Hz, 1H), 5.67 (s, 2H), 3.61 (s, 3H).

Example 37 Synthesis of Compound 37 (4-(4-((4-chlorophenyl)amino)pyrido[2,3-d]pyrimidin-6-yl)-6-methyl-1,6-dihydro-7H-pyrrolo[2,3-c]pyridin-7-one)

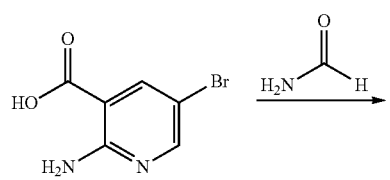

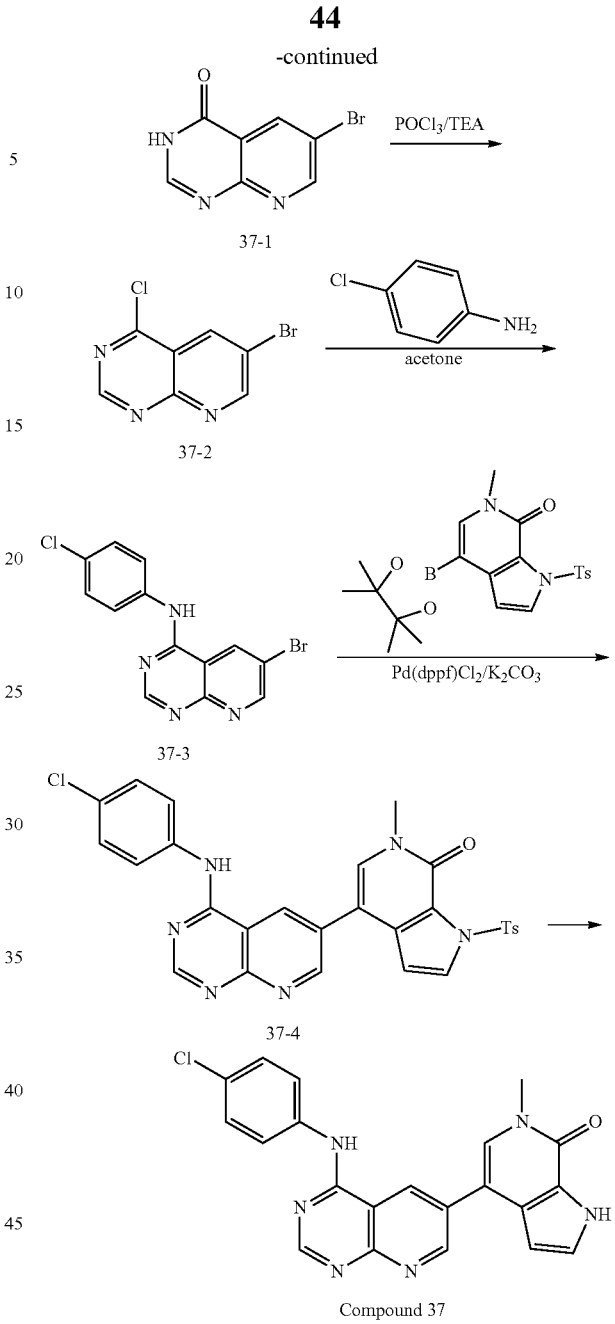

1. Synthesis of Compound 37-1

2-amino-5-bromonicotinic acid (3.00 g) was dissolved in formamide (15 mL), stirred at 160° C. for 4 h, then added formamide (20 mL), continued the reaction at 160° C. for 6 h, cooled, poured into 150 mL of water, and filtered to collect the solid, giving 2.20 g of a yellow solid.

2. Synthesis of Compound 37-2

Compound 37-1 (0.40 g) was dissolved in phosphorus oxychloride (5 mL), triethylamine (0.5 mL) was added, reacted at 120° C. for 3 h, concentrated, toluene (20 mL) was added to the crude product, concentrated, and repeated three times to obtain 0.60 g of the brown solid, which was directly used in the next reaction.

3. Synthesis of Compound 37-3

Compound 37-2 (0.60 g) was dissolved in DCM (10 mL), p-chloroaniline (0.30 g), triethylamine (1 mL) was added, stirred at room temperature for 5 h, concentrated, the crude product was purified by column chromatography with DCM:MeOH=100:5-100:10, the product was 0.70 g of brown-red solid.

4. Synthesis of Compound 37-4

Compound 37-3 (0.30 g), compound 2M-1 (0.38 g) and Pd(dppf)Cl$_2$.DCM (0.07 g) was dissolved in dioxane, potassium carbonate (0.19 g) and water (1.5 mL) were added, protected by nitrogen, stirred at 100° C. overnight. Cooled, EA (30 mL) and saturated Na$_2$CO$_3$ solution (30 mL) were added, separated the liquid, the aqueous phase was extracted 3 times with EA, the organic phases were combined, washed with saturated brine 3 times, dried over anhydrous sodium sulfate, and concentrated. The crude product was purified by column chromatography with DCM:MeOH=100:3, the product was 0.29 g of yellow solid.

5. Synthesis of Compound 37

Compound 37-4 (0.29 g) was dissolved in methanol (15 mL), sodium hydroxide (0.21 g) was added, stirred at room temperature overnight, concentrated, and the crude product was purified by column chromatography with DCM:MeOH=100:5, the product was a yellow solid as compound 37, 0.07 g.

LCMS: [M+1]+=403.1.

$^1$HNMR: (400 MHz, DMSO) δ 12.28 (s, 1H), 8.76 (s, 1H), 7.92 (d, J=8.8 Hz, 2H), 7.68 (s, 1H), 7.61-7.53 (m, 2H), 7.52-7.45 (m, 3H), 7.43 (t, J=2.8 Hz, 1H), 6.67-6.53 (m, 1H), 3.60 (s, 3H).

Example 38 Synthesis of Compound 38 (4-(1-(2,6-dichlorobenzyl)-2-methyl-1H-pyrrolo[3,2-b]pyridin-6-yl)-6-methyl-1,6-dihydro-7H-pyrrolo[2,3-c]pyridin-7-one)

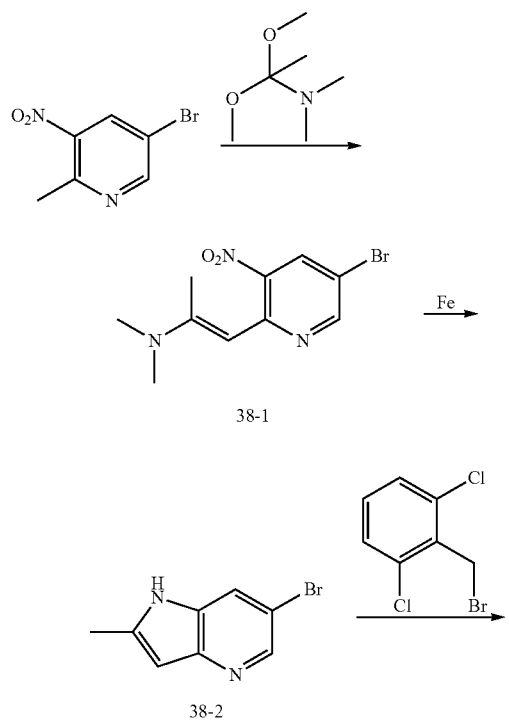

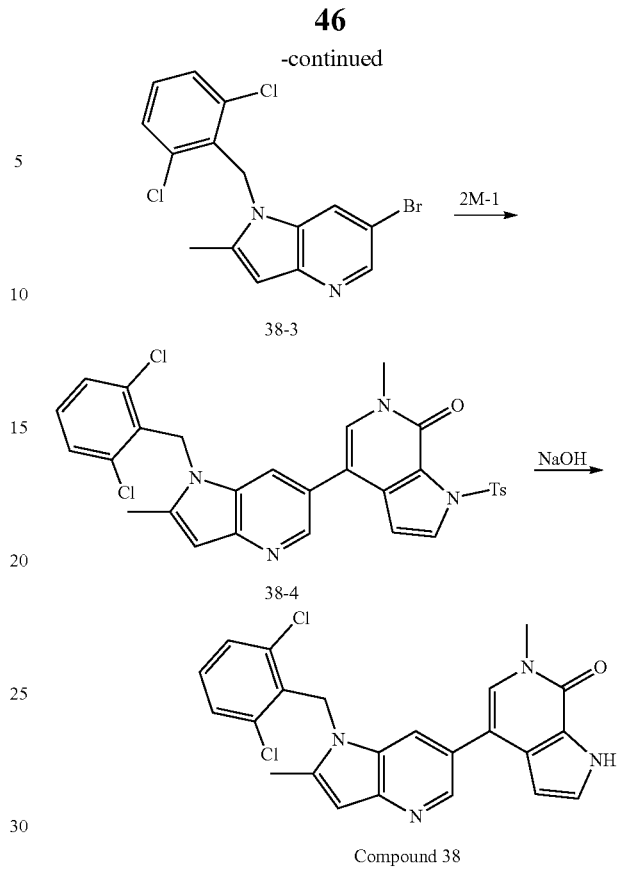

1. Synthesis of Compound 38-1

5-Bromo-2-methyl-3-nitropyridine (1.00 g) and N,N-dimethylacetamide dimethyl acetal (1.22 g) were dissolved in DMF (5 mL) and heated at 100° C. for 1 h. Cooled, diluted with EA (300 mL), washed 3 times with saturated brine, dried over anhydrous sodium sulfate, and concentrated. The product was 1.30 g of brownish red solid.

2. Synthesis of Compound 38-2

Compound 38-1 (1.30 g) and iron powder (3.00 g) were dissolved in glacial acetic acid (30 mL), stirred at 80° C. for 90 min, cooled, poured into saturated Na$_2$CO$_3$ solution (200 mL), filtered through celite, filter cake was washed with EA, the filtrate was extracted 3 times with EA, the organic phases were combined, washed 3 times with saturated brine, dried over anhydrous sodium sulfate, and concentrated. The crude product was purified by basic alumina column chromatography with PE:EA=100:30-100:50, the product was 0.63 g of earth yellow solid.

3. Synthesis of Compound 38-3

Compound 38-2 (0.53 g) was dissolved in DMF (25 mL), protected by nitrogen, cooled to 0° C., sodium hydride (0.13 g) was added, naturally raised to room temperature and stirred for 1 h, cooled to 0° C., and 2,6-dichlorobenzyl bromide (0.60 g) was added, naturally warmed to room temperature and reacted for 2.5 h, poured into ice water to quench, extracted 3 times with EA, the organic phases were combined, washed with saturated brine 3 times, dried over anhydrous sodium sulfate, and concentrated. The crude product was purified by column chromatography with PE:EA=100:10-100:30, the product was 0.84 g of yellow solid.

4. Synthesis of Compound 38-4

Compound 38-3 (0.20 g), compound 2M-1 (0.23 g) and Pd(dppf)Cl$_2$.DCM (0.04 g) were dissolved in dioxane (5 mL), K₂CO₃ (0.11 g) and water (1 mL) were added, protected by nitrogen, heated and reacted at 100° C. overnight. Cooled, EA (50 mL) and saturated Na₂CO₃ solution (50 mL) were added, mixed the solution, separated the liquid, extract the aqueous phase 3 times with EA, the organic phases were combined, washed 3 times with saturated brine, dried over anhydrous sodium sulfate, concentrated, and the crude product was purified by column chromatography with DCM:MeOH=100:3 to obtain 0.30 g of crude brown oil.

5. Synthesis of Compound 38

Compound 38-4 (0.30 g) was added to methanol (15 mL), sodium hydroxide (0.20 g) was added, stirred at room temperature for 3 h, silica gel sample column chromatography was added to purify with DCM:MeOH=100:2-100:3, the product was 0.08 g of yellow solid.

LCMS: [M+1]+=437.1.

¹HNMR: (400 MHz, DMSO) δ 12.13 (s, 1H), 8.42 (d, J=1.8 Hz, 1H), 7.63-7.40 (m, 4H), 7.39-7.20 (m, 3H), 6.43 (s, 1H), 5.65 (s, 2H), 3.60 (s, 3H), 2.49 (s, 3H).

Example 39 Synthesis of Compound 39 (4-(1-(4-chlorobenzyl)-1H-pyrazolo[4,3-b]pyridin-6-yl)-6-methyl-1,6-dihydro-7H-pyrrolo[2,3-c]pyridin-7-one)

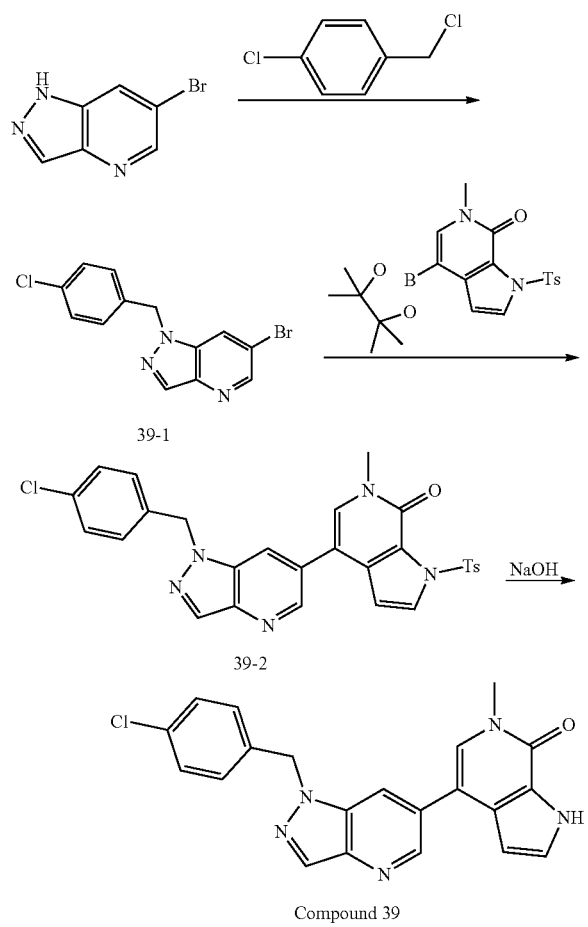

1. Synthesis of Compound 39-1

6-bromo-1H-pyrazolo[4,3-b]pyridine (1.00 g) was dissolved in DMF (30 mL), protected by nitrogen, added sodium hydride (0.24 g) at 0° C., warmed to room temperature and reacted for 1 h, p-chlorobenzyl chloride (0.90 g) was added at 0° C., reacted overnight at room temperature. Poured into ice water (100 mL) to quench, extracted 3 times with EA, the organic phases were combined, washed with saturated brine, dried over anhydrous sodium sulfate, concentrated, and purified the crude product by column chromatography with PE:EA=100:4-100:20, The product was 0.80 g of white solid.

2. Synthesis of Compound 39-2

Compound 39-1 (0.30 g), 2M-1 (0.40 g) and Pd(dppf)Cl₂.DCM (0.08 g) were dissolved in dioxane (8 mL), potassium carbonate (0.19 g) and water (1.5 mL) were added, protected by nitrogen, heated and stirred at 100° C. overnight. Cooled, poured into EA (100 mL)/saturated Na₂CO₃ solution (100 mL), separated the layers, extracted the aqueous phase 3 times with EA, the organic phases were combined, wash with saturated brine, dry over anhydrous sodium sulfate, and concentrated. The crude product was purified by column chromatography with DCM:MeOH=100:2.5, the product was 0.52 g of yellow semi-solid.

3. Synthesis of Compound 39

Compound 39-2 (0.52 g) was dissolved in methanol (10 mL) and DCM (10 mL), sodium hydroxide (0.12 g) was added, stirred at room temperature, concentrated, and purified by crude column chromatography with DCM:MeOH=100:2.5-100:3, to obtain compound 39 as a yellow solid, 0.10 g.

LCMS: [M+1]⁺=390.1;

¹HNMR: (400 MHz, DMSO) δ 12.23 (s, 1H), 8.78 (d, J=1.8 Hz, 1H), 8.43-8.20 (m, 2H), 7.58 (d, J=4.1 Hz, 1H), 7.49-7.17 (m, 5H), 6.57-6.21 (m, 1H), 5.76 (d, J=5.8 Hz, 2H), 3.62 (s, 3H).

Example 40 Synthesis of Compound 40 (4-(1-((4-chlorophenyl)sulfonyl)-1H-pyrrolo[2,3-b]pyridin-6-yl)-6-methyl-1,6-dihydro-7H-pyrrolo[2,3-c]pyridin-7-one)

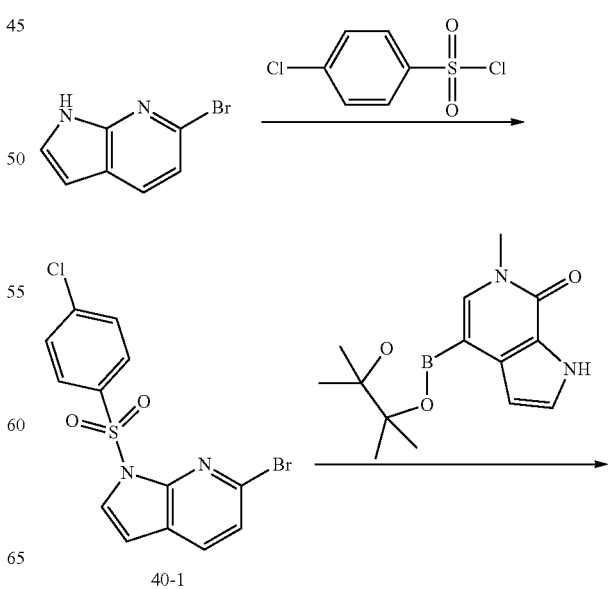

-continued

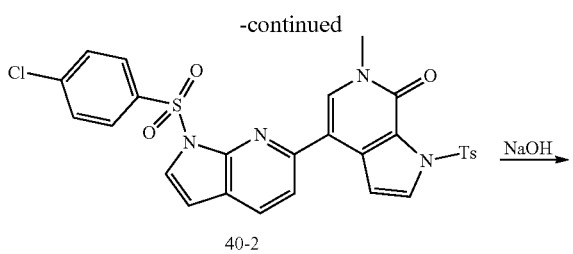

40-2

Compound 40

1. Synthesis of Compound 40-1

6-bromo-7-azaindole (1.00 g) was dissolved in DMF (15 mL), protected by nitrogen, sodium hydride (0.31 g) was added at 0° C., stirred at room temperature for 1 h, and p-chlorobenzenesulfonyl chloride was added at 0° C. (1.30 g), stirred at room temperature for 2 h, quenched with the addition of ice water (50 mL), extracted 3 times with EA, organic phases were combined, washed 3 times with saturated brine, dried over anhydrous sodium sulfate, concentrated, the product was 1.30 g of yellow solid.

2. Synthesis of Compound 40-2

Compound 40-1 (0.35 g), compound 2M-1 (0.49 g) and Pd(PPh$_3$)$_4$ (0.06 g) were dissolved in dioxane (7 mL), potassium carbonate (0.20 g) and water (7 mL) were added, protected by nitrogen, reacted overnight at 100° C. Cooled, poured into EA (50 mL)/saturated Na$_2$CO$_3$ solution (50 mL), separated the liquid, extracted the aqueous phase 3 times with EA, the organic phases were combined, washed with saturated brine, dried over anhydrous sodium sulfate, concentrated, and the crude product was purified by column chromatography with DCM:MeOH=100:3, the product was 0.35 g of light yellow solid.

3. Synthesis of Compound 40

Compound 40-2 (0.28 g) was dissolved in methanol (10 mL) and dichloromethane (0 mL), sodium hydroxide (0.07 g) was added, stirred at room temperature overnight. After concentration, the crude product was purified by column chromatography with DCM:MeOH=100:3. The crude product was added EA (10 mL) for beating. The solid was collected by filtration to obtain 0.04 g of product.

LCMS: [M+1]$^+$=439.1;

$^1$HNMR: (400 MHz, DMSO) δ 12.12 (s, 1H), 8.11 (ddd, J=14.8, 8.4, 5.5 Hz, 3H), 7.96 (s, 1H), 7.85 (dd, J=16.1, 6.2 Hz, 2H), 7.71-7.52 (m, 2H), 7.42 (dt, J=4.9, 2.7 Hz, 2H), 6.85 (d, J=4.0 Hz, 1H), 3.65 (s, 3H).

Example 41 Synthesis of Compound 41 (N-(1-(4-chlorobenzyl)-2-methyl-6-(6-methyl-7-oxo-6,7-dihydro-1H-pyrrolo[2,3-c]pyridin-4-yl)-1H-benzo[d]imidazol-4-yl)ethanesulfonamide)

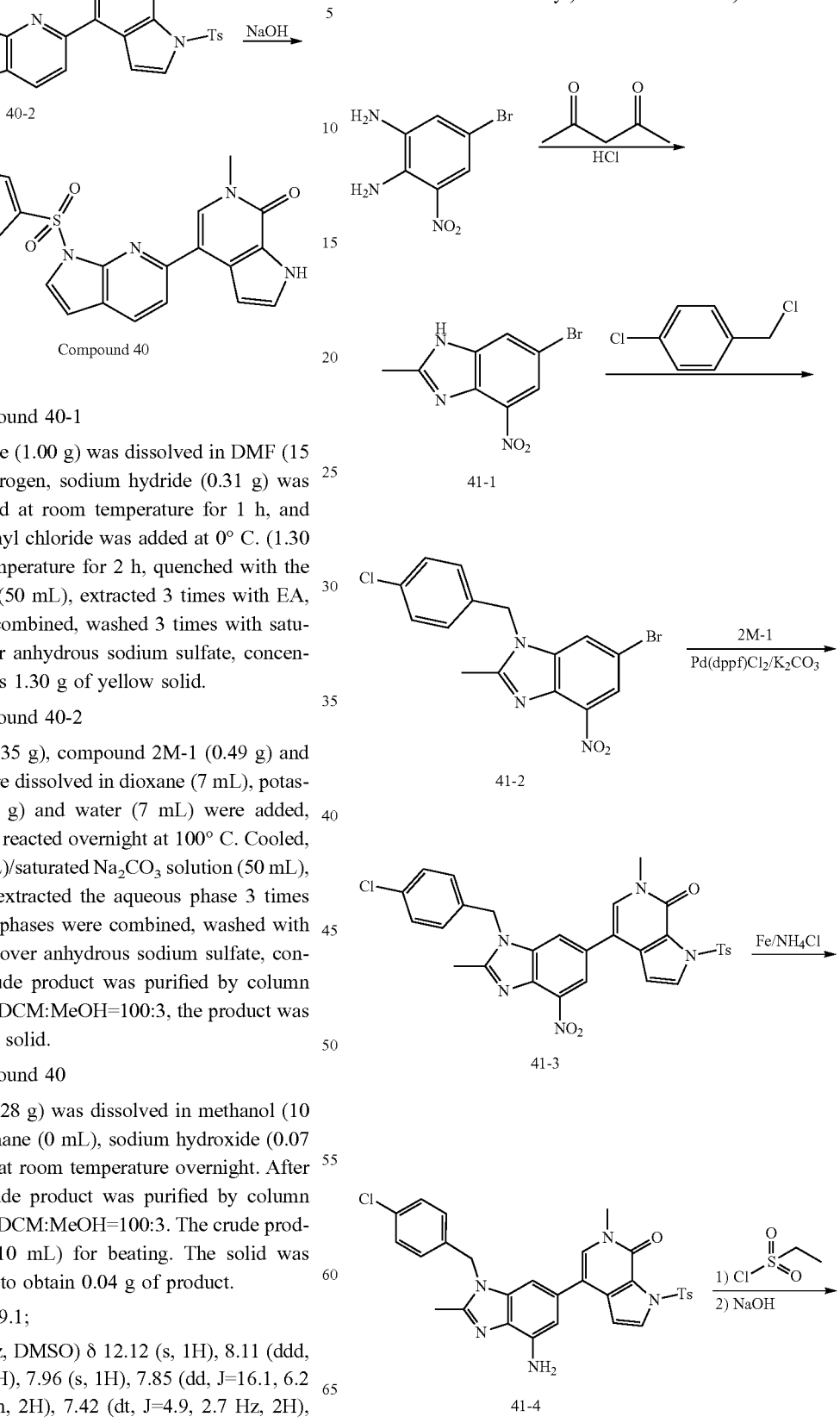

41-1

41-2

41-3

41-4

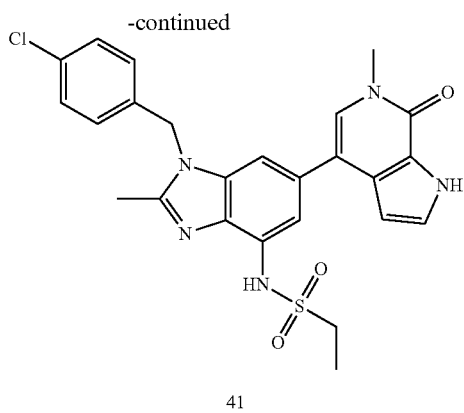

41

1. Synthesis of Compound 41-1

5-bromo-3-nitro-benzene-1,2-diamine (1.00 g) and acetylacetone (0.86 g) was dissolved in ethanol (20 mL), 5N hydrochloric acid (6 mL) was added, stirred at 100° C. for 4 h, cooled, concentrated and purified by column chromatography with PE:EA=100:30 to obtain 0.90 g of yellow solid product.

2. Synthesis of Compound 41-2

Compound 41-1 (0.85 g) and potassium carbonate (0.92 g) were dissolved in acetonitrile (20 mL) and DMF (4 mL), p-chlorobenzyl chloride (0.98 g) was added, and stirred at 60° C. overnight. Cooled, poured into 100 mL of water, extracted 3 times with EA, the organic phases were combined, washed 3 times with saturated brine, dried over anhydrous sodium sulfate, and concentrated. The crude product was purified by column chromatography with PE:EA=100:30 to obtain 1.04 g of yellow solid.

3. Synthesis of Compound 41-3

Compound 41-2 (0.50 g), compound 2M-1 (0.56 g) and Pd(dppf)Cl$_2$.DCM (0.11 g) were dissolved in dioxane (10 mL), potassium carbonate (0.27 g) and water (2 mL) were added, protected by nitrogen, stirred at 90° C. overnight. Cooled, poured into 50 mL of water, extracted three times with EA, the organic phases were combined, washed with saturated brine 3 times, dried over anhydrous sodium sulfate, and concentrated. The crude product was purified by column chromatography with DCM:MeOH=100:3, to give 0.83 g of yellow solid.

4. Synthesis of Compound 41-4

Compound 41-3 (0.80 g) was dissolved in THF (15 mL) and ethanol (15 mL), iron powder (0.37 g), ammonium chloride (0.14 g) and water (10 mL) were added, stirred at 90° C. overnight. Filtered while hot, the filter cake was washed with methanol 3 times, concentrated the filtrate, added saturated sodium carbonate (50 mL), extracted 3 times with EA, the organic phases were combined, washed with saturated brine 3 times, dried over anhydrous sodium sulfate, concentrated, the crude product was purified by column chromatography with DCM:MeOH=100:4 to obtain 0.43 g of dark yellow solid.

5. Synthesis of Compound 41

Compound 41-4 (0.43 g) was dissolved in DCM (10 mL), triethylamine (0.31 g) and ethylsulfonyl chloride (0.19 g) were added, stirred at room temperature for 2 h, concentrated, added dioxane (7.5 mL) and sodium hydroxide (10%, V/V, 2.5 mL), stirred and heated at 70° C. for 3 h, cooled, poured into saturated ammonium chloride (100 mL), separated, and the aqueous phase was extracted 3 times with EA, the organic phases were combined, washed three times with saturated brine, dried over anhydrous sodium sulfate, concentrated, and purified by crude column chromatography with DCM:MeOH=100:3 to obtain 0.08 g of yellow solid.

LCMS: [M+1]$^+$=511.1.

1HNMR (300 MHz, DMSO) δ 12.13 (s, 1H), 9.65 (s, 1H), 7.50-7.35 (m, 4H), 7.35-7.30 (m, 2H), 7.25-7.20 (m, 2H), 6.40 (s, 1H), 5.55 (s, 2H), 3.60 (s, 3H), 3.35-3.20 (m, 2H) 2.60-2.50 (m, 3H). 1.45-1.20 (m, 3H).

Using a method basically similar to that of Example 41, the corresponding p-chlorobenzyl chloride derivative is is used to replace

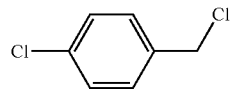

(P-chlorobenzyl chloride) in the example to prepare the example in Table 6 below. The corresponding p-chlorobenzyl chloride derivative, such as

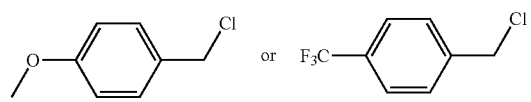

etc, can all be purchased through commercially available channels.

TABLE 6

| Example | Structure | Chemical Name | Physical data (MS) (M + H)$^+$ |
| --- | --- | --- | --- |
| 41 | ![structure] | N-(1-(4-chlorobenzyl)-2-methyl-6-(6-methyl-7-oxo-6,7-dihydro-1H-pyrrolo[2,3-c]pyridin-4-yl)-1H-benzo[d]imidazol-4-yl)ethanesulfonamide | 511.1 |

TABLE 6-continued

| Example | Structure | Chemical Name | Physical data (MS) (M + H)+ |
|---|---|---|---|
| 42 | 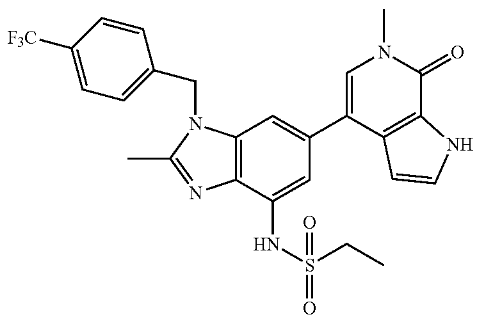 [SMILES: CCS(=O)(=O)Nc1cc(-c2cn(C)c(=O)c3[nH]ccc23)cc2c1nc(C)n2Cc1ccc(C(F)(F)F)cc1] | N-(2-methyl-6-(6-methyl-7-oxo-6,7-dihydro-1H-pyrrolo[2,3-c]pyridin-4-yl)-1-(4-(trifluoromethyl)benzyl)-1H-benzo[d]imidazol-4-yl)ethanesulfonamide | 544.6 |
| 43 | 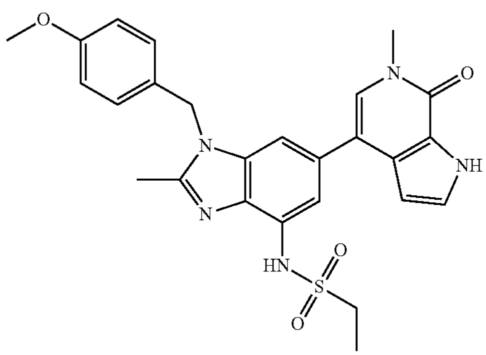 [SMILES: CCS(=O)(=O)Nc1cc(-c2cn(C)c(=O)c3[nH]ccc23)cc2c1nc(C)n2Cc1ccc(OC)cc1] | N-(1-(4-methoxybenzyl)-2-methyl-6-(6-methyl-7-oxo-6,7-dihydro-1H-pyrrolo[2,3-c]pyridin-4-yl)-1H-benzo[d]imidazol-4-yl)ethanesulfonamide | 506.6 |
| 44 | 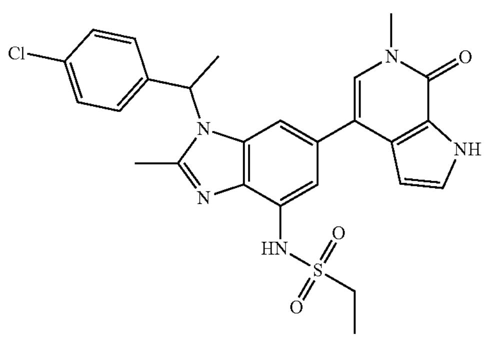 [SMILES: CCS(=O)(=O)Nc1cc(-c2cn(C)c(=O)c3[nH]ccc23)cc2c1nc(C)n2C(C)c1ccc(Cl)cc1] | N-(1-(1-(4-chlorophenyl)ethyl)-2-methyl-6-(6-methyl-7-oxo-6,7-dihydro-1H-pyrrolo[2,3-c]pyridin-4-yl)-1H-benzo[d]imidazol-4-yl)ethanesulfonamide | 525.1 |
| 45 | 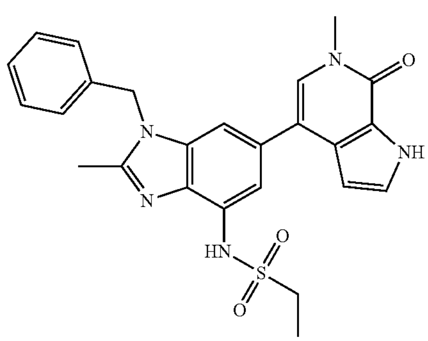 [SMILES: CCS(=O)(=O)Nc1cc(-c2cn(C)c(=O)c3[nH]ccc23)cc2c1nc(C)n2Cc1ccccc1] | N-(1-benzyl-2-methyl-6-(6-methyl-7-oxo-6,7-dihydro-1H-pyrrolo[2,3-c]pyridin-4-yl)-1H-benzo[d]imidazol-4-yl)ethanesulfonamide | 476.5 |

TABLE 6-continued

| Example | Structure | Chemical Name | Physical data (MS) (M + H)+ |
|---|---|---|---|
| 46 | 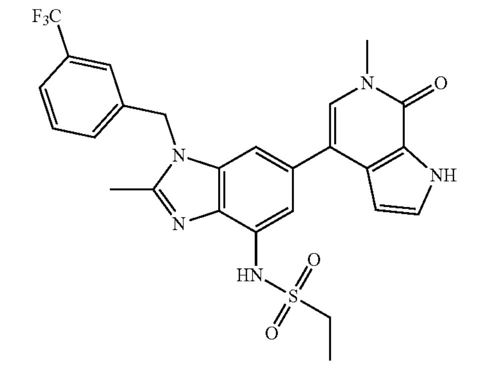 [SMILES: CCS(=O)(=O)Nc1cc(-c2cn(C)c(=O)c3[nH]ccc23)cc2c1nc(C)n2Cc1cccc(C(F)(F)F)c1] | N-(2-methyl-6-(6-methyl-7-oxo-6,7-dihydro-1H-pyrrolo[2,3-c]pyridin-4-yl)-1-(3-(trifluoromethyl)benzyl)-1H-benzo[d]imidazol-4-yl)ethanesulfonamide | 544.5 |
| 47 | 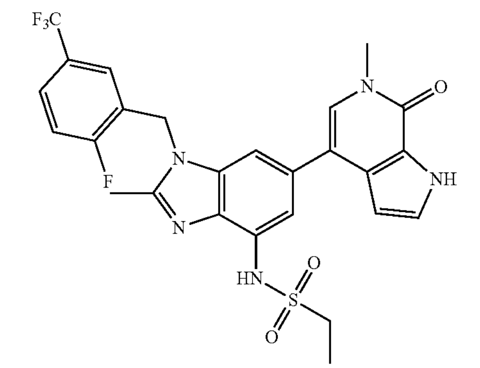 [SMILES: CCS(=O)(=O)Nc1cc(-c2cn(C)c(=O)c3[nH]ccc23)cc2c1nc(C)n2Cc1cc(C(F)(F)F)ccc1F] | N-(2-methyl-6-(6-methyl-7-oxo-6,7-dihydro-1H-pyrrolo[2,3-c]pyridin-4-yl)-1-(2-fluoro-5-(trifluoromethyl)benzyl)-1H-benzo[d]imidazol-4-yl)ethanesulfonamide | 562.5 |
| 48 | 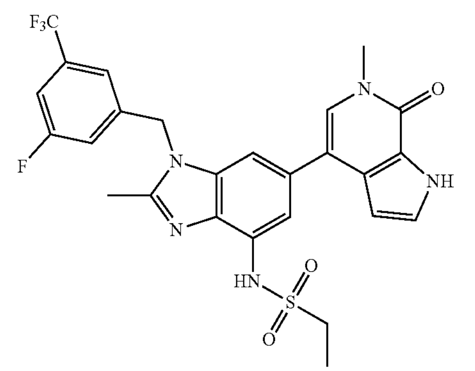 [SMILES: CCS(=O)(=O)Nc1cc(-c2cn(C)c(=O)c3[nH]ccc23)cc2c1nc(C)n2Cc1cc(F)cc(C(F)(F)F)c1] | N-(2-methyl-6-(6-methyl-7-oxo-6,7-dihydro-1H-pyrrolo[2,3-c]pyridin-4-yl)-1-(3-fluoro-5-(trifluoromethyl)benzyl)-1H-benzo[d]imidazol-4-yl)ethanesulfonamide | 562.5 |
| 49 | 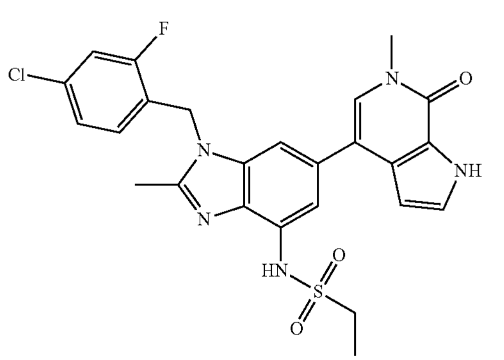 [SMILES: CCS(=O)(=O)Nc1cc(-c2cn(C)c(=O)c3[nH]ccc23)cc2c1nc(C)n2Cc1ccc(Cl)cc1F] | N-(2-methyl-6-(6-methyl-7-oxo-6,7-dihydro-1H-pyrrolo[2,3-c]pyridin-4-yl)-1-(2-fluoro-4-chlorobenzyl)-1H-benzo[d]imidazol-4-yl)ethanesulfonamide | 529.0 |

TABLE 6-continued

| Example | Structure | Chemical Name | Physical data (MS) (M + H)+ |
|---------|-----------|---------------|------------------------------|
| 50 | 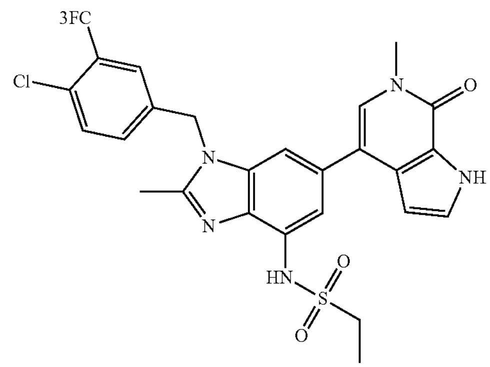 | N-(2-methyl-6-(6-methyl-7-oxo-6,7-dihydro-1H-pyrrolo[2,3-c]pyridin-4-yl)-1-(3-(trifluoromethyl)-4chlorobenzyl)-1H-benzo[d]imidazol-4-yl)ethanesulfonamide | 579.0 |
| 51 | 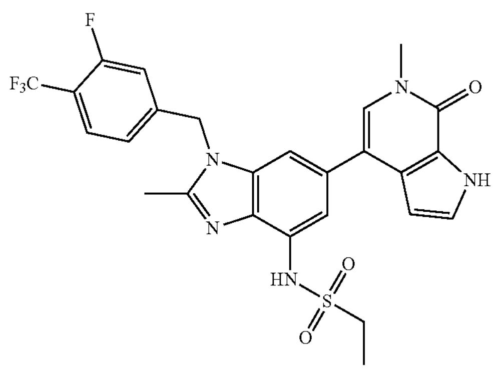 [SMILES: CCS(=O)(=O)Nc1cc(-c2cn(C)c(=O)c3[nH]ccc23)cc2c1nc(C)n2Cc1ccc(C(F)(F)F)c(F)c1] | N-(2-methyl-6-(6-methyl-7-oxo-6,7-dihydro-1H-pyrrolo[2,3-c]pyridin-4-yl)-1-(3-fluoro-4-(trifluoromethyl)benzyl)-1H-benzo[d]imidazol-4-yl)ethanesulfonamide | 562.5 |
| 52 | 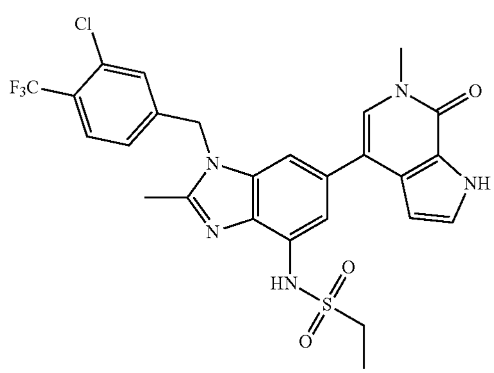 [SMILES: CCS(=O)(=O)Nc1cc(-c2cn(C)c(=O)c3[nH]ccc23)cc2c1nc(C)n2Cc1ccc(C(F)(F)F)c(Cl)c1] | N-(2-methyl-6-(6-methyl-7-oxo-6,7-dihydro-1H-pyrrolo[2,3-c]pyridin-4-yl)-1-(3-chloro-4-(trifluoromethyl)benzyl)-1H-benzo[d]imidazol-4-yl)ethanesulfonamide | 579.0 |
| 53 | 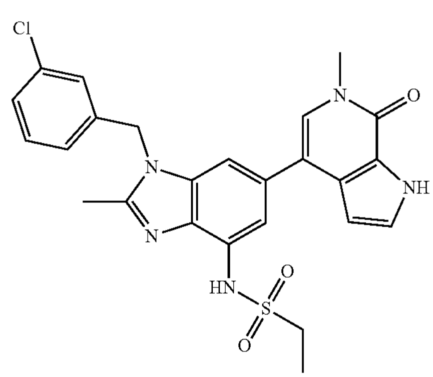 [SMILES: CCS(=O)(=O)Nc1cc(-c2cn(C)c(=O)c3[nH]ccc23)cc2c1nc(C)n2Cc1cccc(Cl)c1] | N-(2-methyl-6-(6-methyl-7-oxo-6,7-dihydro-1H-pyrrolo[2,3-c]pyridin-4-yl)-1-(3-chlorobenzyl)-1H-benzo[d]imidazol-4-yl)ethanesulfonamide | 511.0 |

TABLE 6-continued

| Example | Structure | Chemical Name | Physical data (MS) (M + H)+ |
|---|---|---|---|
| 54 | 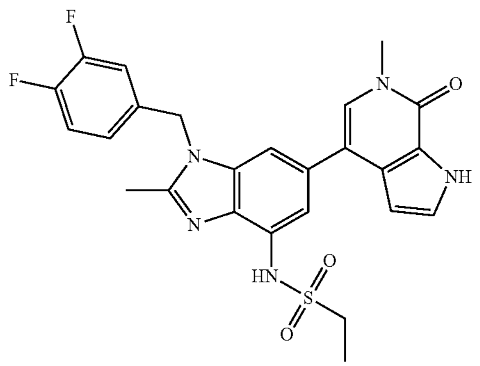 [SMILES: CCS(=O)(=O)Nc1cc(-c2cn(C)c(=O)c3[nH]ccc23)cc2c1nc(C)n2Cc1ccc(F)c(F)c1] | N-(2-methyl-6-(6-methyl-7-oxo-6,7-dihydro-1H-pyrrolo[2,3-c]pyridin-4-yl)-1-(2,4-difluorobenzyl)-1H-benzo[d]imidazol-4-yl)ethanesulfonamide | 512.5 |
| 55 | 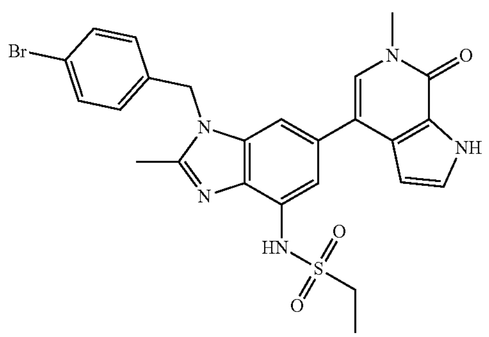 | N-(2-methyl-6-(6-methyl-7-oxo-6,7-dihydro-1H-pyrrolo[2,3-c]pyridin-4-yl)-1-(4-bromobenzyl)-1H-benzo[d]imidazol-4-yl)ethanesulfonamide | 555.4 |
| 56 | 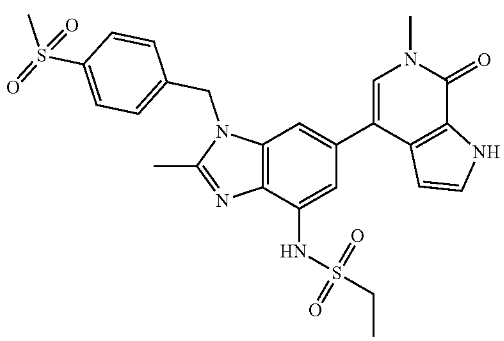 [SMILES: CCS(=O)(=O)Nc1cc(-c2cn(C)c(=O)c3[nH]ccc23)cc2c1nc(C)n2Cc1ccc(S(C)(=O)=O)cc1] | N-(2-methyl-6-(6-methyl-7-oxo-6,7-dihydro-1H-pyrrolo[2,3-c]pyridin-4-yl)-1-(4-(methylsulfonyl)benzyl)-1H-benzo[d]imidazol-4-yl)ethanesulfonamide | 554.6 |
| 57 | 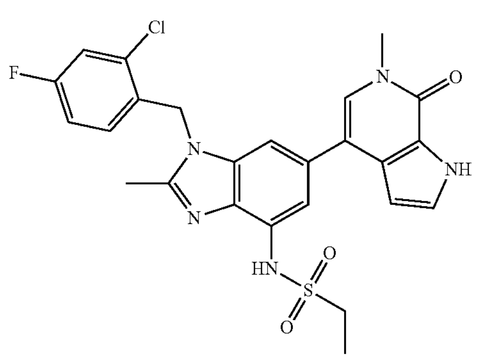 [SMILES: CCS(=O)(=O)Nc1cc(-c2cn(C)c(=O)c3[nH]ccc23)cc2c1nc(C)n2Cc1ccc(F)cc1Cl] | N-(1-(2-chloro-4-fluorobenzyl)-2-methyl-6-(6-methyl-7-oxo-6,7-dihydro-1H-pyrrolo[2,3-c]pyridin-4-yl)-1H-benzo[d]imidazol-4-yl)ethanesulfonamide | 529.0 |

Example 58 Synthesis of Compound 58 (N-(5-(6-methyl-7-oxo-6,7-dihydro-1H-pyrrolo[2,3-c]pyridin-4-yl)-3-(4-(trifluoromethyl)benzyl)-3H-imidazo[4,5-b]pyridin-7-yl)ethanesulfonamide)

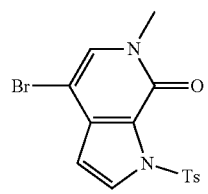

1M-15

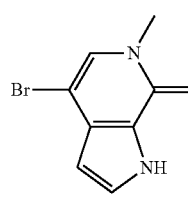

58-1

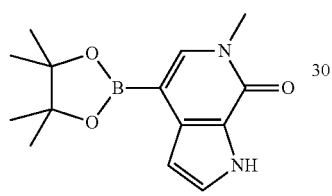

58-2

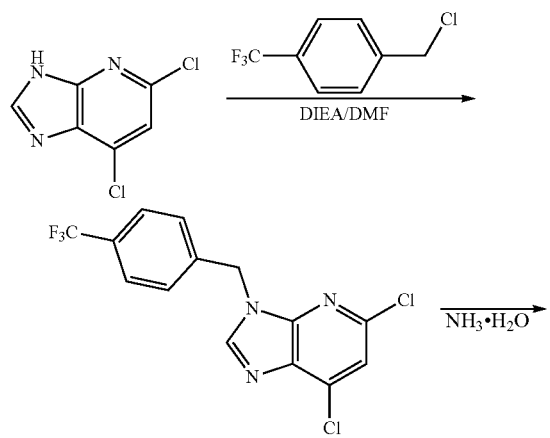

58-3

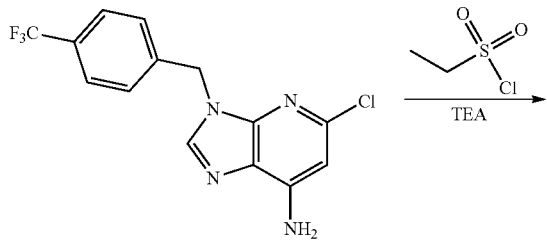

58-4

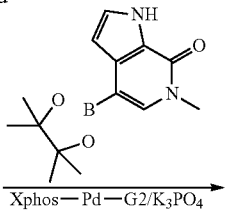

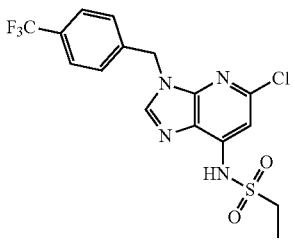

58-5

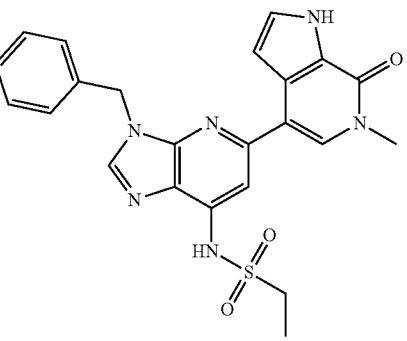

58

1. Synthesis of Compound 58-1

1M-15 (7.60 g) and NaOH (1.60 g) were dissolved in dioxane and water, reacted at 80° C. for 4 h. Cooled, poured into H₂O, extracted three times with DCM, the organic phases were combined, washed with saturated brine, dried over anhydrous sodium sulfate, and concentrated. The crude product was purified by column with DCM:MeOH=90:10 to obtain 3.20 g of gray solid.

2. Synthesis of Compound 58-2

Compound 58-1(6.00 g), (Bpin)₂ (8.00 g), SPhos (1.29 g), PdCl₂(CH₃CN)₂ (0.68 g) and KOAc (3.40 g) were dissolved in dioxane, protected by nitrogen, reacted at 80° C. for 4 h. Cooled, poured into water, extracted three times with EA, the organic phases were combined, washed with saturated brine, dried over anhydrous sodium sulfate, and concentrated. The crude product was purified by column with PE:EA=50:50 to obtain 3.20 g of gray solid.

3. Synthesis of Compound 58-3

5,7-dichloro-1H-imidazo[4,5-B]pyridine (1.88 g), p-trifluoromethylbenzyl chloride (1.94 g) and DIEA (1.56 g) were dissolved in DMF and reacted overnight at room temperature. The reaction was poured into water, extracted three times with EA, the organic phases were combined, washed with saturated brine, dried over anhydrous sodium sulfate, and concentrated. The crude product was purified by column chromatography with PE:EA=50:50 to obtain 1.50 g of gray solid.

4. Synthesis of Compound 58-4

58-3 (1.50 g) was placed in ammonia water and reacted at 150° C. overnight. After cooling, filtering with suction, the filter cake was washed with water, and the solid was dried in vacuum to obtain 1.10 g of white solid.

5. Synthesis of Compound 58-5

58-4 (1.10 g) and TEA (1.70 g) was dissolved in DCM, ethylsulfonyl chloride (0.86 g) was added dropwise, reacted at room temperature for 2 h. Poured into water, extracted three times with DCM, the organic phases were combined, washed with saturated brine, dried over anhydrous sodium sulfate, and concentrated. The crude product was purified by column chromatography with PE:EA=30:70 to give 0.80 g of gray solid.

6. Synthesis of Compound 58

58-2 (0.42 g), 58-5 (0.27 g), K₂CO₃ (0.41 g) and Xphos-Pd-G2 (0.08 g) were placed in dioxane and water, reacted at 80° C. for 4 h. Cooled, poured into water, extracted three times with EA, the organic phases were combined, washed with saturated brine, dried over anhydrous sodium sulfate, and concentrated. The crude product was purified by column chromatography with MeOH:DCM=10:90 to give 0.10 g of gray solid.

LCMS: [M+1]⁺=531.1.

¹H NMR (400 MHz, DMSO) δ 12.13 (s, 1H), 10.61 (s, 1H), 8.56 (s, 1H), 7.75 (d, J=10.1 Hz, 3H), 7.67-7.53 (m, 3H), 7.32 (t, J=2.8 Hz, 1H), 6.73-6.54 (m, 1H), 5.65 (s, 2H), 3.72-3.53 (m, 5H), 1.31 (t, J=7.3 Hz, 3H).

Example 59 Synthesis of Compound 59 (N-(3-(2,4-difluorobenzyl)-5-(6-methyl-7-oxo-6,7-dihydro-1H-pyrrolo[2,3-c]pyridin-4-yl)-3H-imidazo[4,5-b]pyridin-7-yl)ethanesulfonamide)

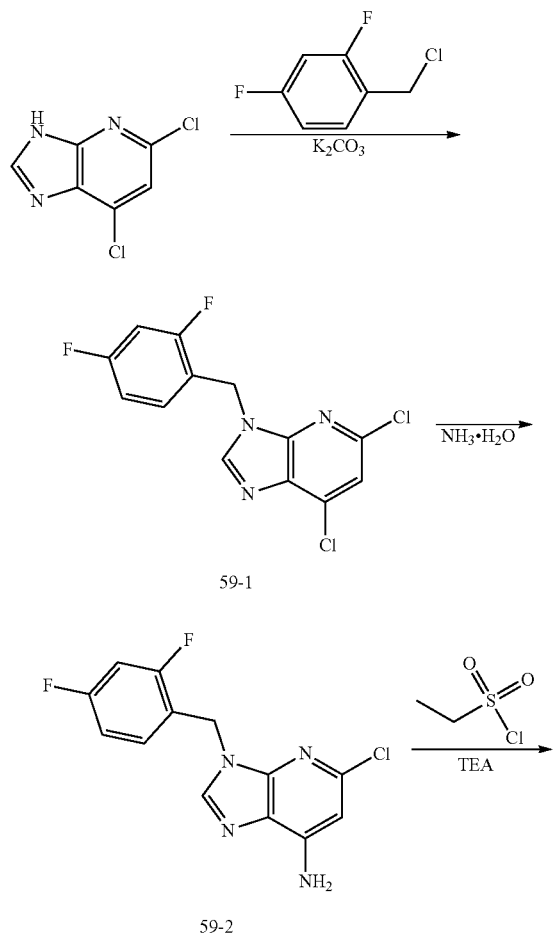

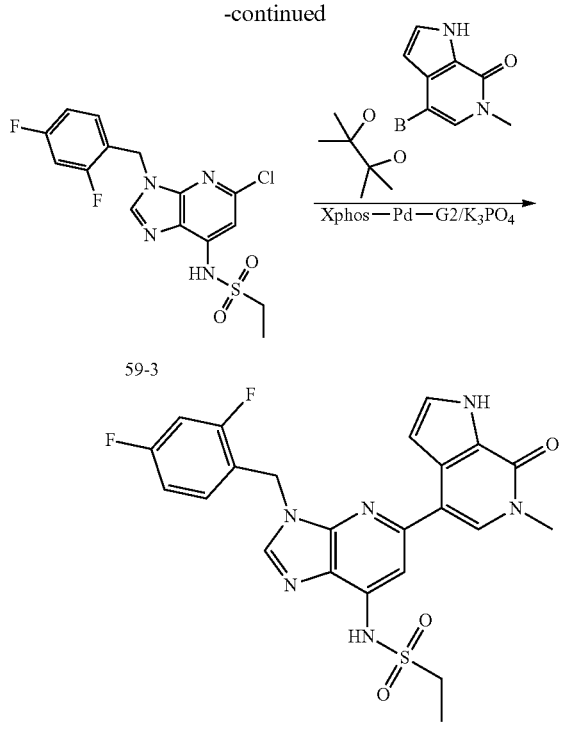

1. Synthesis of Compound 59-1

5,7-dichloro-1H-imidazo[4,5-B]pyridine (5.00 g), K₂CO₃ (11.00 g) and 2,4-difluorochlorobenzyl (6.50 g) was dissolved in DMF (50 ml), stirred at room temperature for 8 h. The reaction was poured into ice water, filtered with suction, and the filter cake was washed three times with water. The crude product was purified by column chromatography with PE:EA=70:30 to obtain 6.0 g of white solid.

2. Synthesis of Compound 59-2

59-1 (0.60 g) and ammonia (25 mL) was added to the sealed tube and stirred at 150° C. overnight. Poured into 100 mL of water, extracted 3 times with EA, the organic phases were combined, washed three times with saturated brine, dried over anhydrous sodium sulfate, and concentrated to obtain 0.30 g of a white solid.

3. Synthesis of Compound 59-3

59-2(0.15 g), TEA (0.16 g) was dissolved in DCM (5 mL), ethylsulfonyl chloride (0.19 g) was slowly added dropwise at 0° C., after the dropwise addition, the temperature was rised to room temperature, and the mixture was stirred for 5 h. Water was added to the reaction mixture, extracted three times with EA, the organic phases were combined, washed three times with brine, dried over anhydrous sodium sulfate, concentrated, and the crude product was purified by Flash-Prep-HPLC(H2O/CH3CN=40% 45%), to afford light yellow solid 0.10 g.

4. Synthesis of Compound 59

59-3(0.10 g), 8-2(0.07 g), Xphos-Pd-G2(0.02 g) and K₃PO₄(0.11 g) were dissolved in dioxane (5 mL), water (1 mL) was added, the reaction solution was reacted at 80° C. for 8 h under N₂ protect. Cooled, water was added, extracted three times with EA, the organic phases were combined, washed with saturated brine, dried over anhydrous sodium sulfate, concentrated, the crude product was purified by column chromatography to give 0.06 g of brown solid.

LCMS: [M+1]+=499.1.

1H NMR (400 MHz, DMSO) δ 12.12 (d, J=17.8 Hz, 1H), 8.46 (s, 1H), 7.80 (d, J=21.7 Hz, 1H), 7.64-7.59 (m, 1H), 7.55-7.42 (m, 1H), 7.39 (t, J=2.8 Hz, 1H), 7.36-6.97 (m, 3H), 6.80-6.74 (m, 1H), 5.56 (s, 2H), 3.76-3.51 (m, 5H), 1.38-1.25 (m, 3H).

Example 64 Synthesis of Compound 64 (N-(3-(2,4-difluorobenzyl)-2-methyl-5-(6-methyl-7-oxo-6,7-dihydro-1H-pyrrolo[2,3-c]pyridin-4-yl)-3H-imidazo[4,5-b]pyridin-7-yl)ethanesulfonamide)

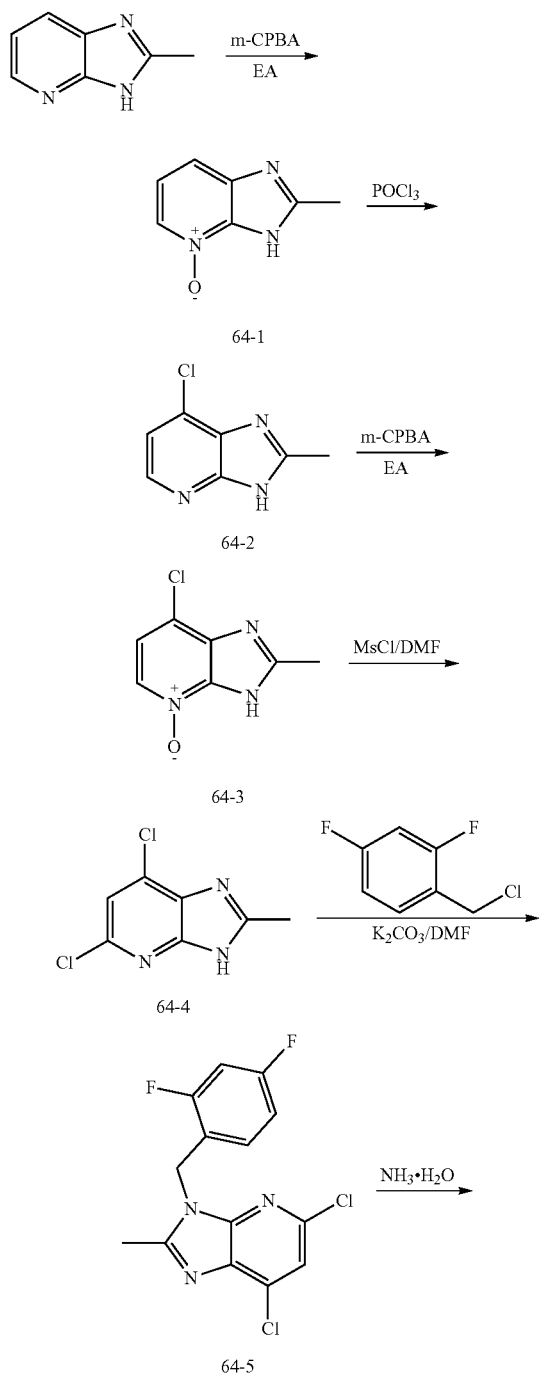

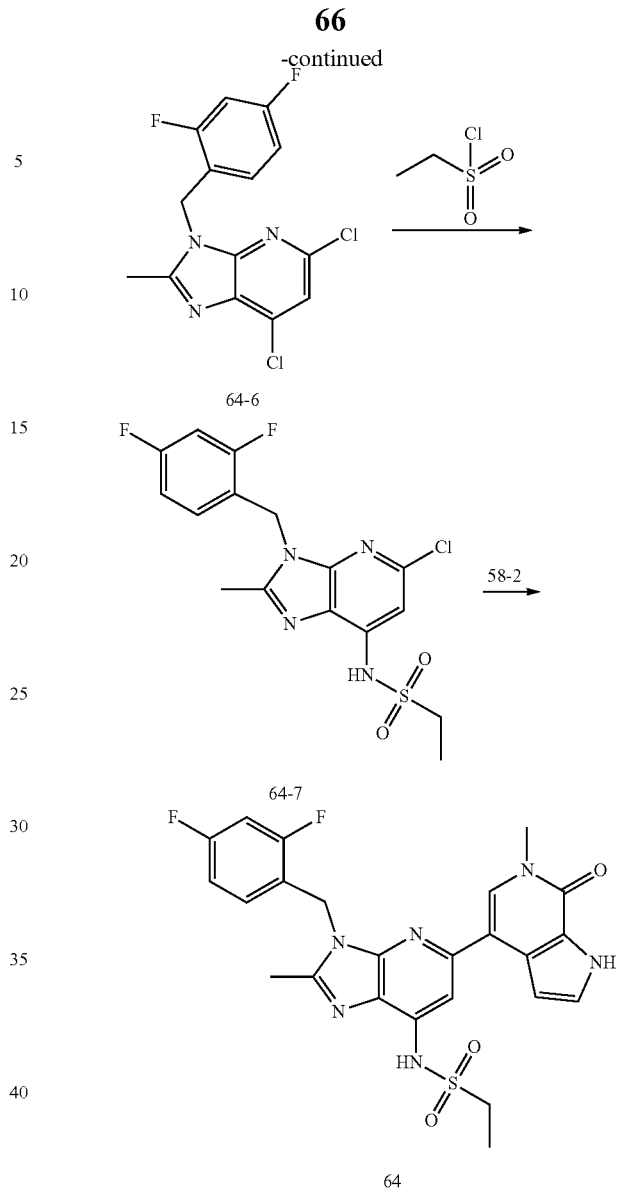

1. Synthesis of Compound 64-1
   2-methyl-1H-imidazo[4,5-b]pyridine (1.08 g) was dissolved in EA (15 mL), m-CPBA (1.86 g) was added, stirred overnight at room temperature, filtered, the filter cake was washed with EA, dried to get white solid 1.05 g.
2. Synthesis of Compound 64-2
   64-1(1.05 g) was dissolved in POCl₃(10 mL), reacted at 80° C. for 15 min, the temperature was raised to 120° C., and reacted for 3 h, the mixture was poured into ice water, extracted three times with EA, the organic layers were combined, concentrated, purified by column chromatography (PE:EA=50:50) to give 0.80 g of white solid.
3. Synthesis of Compound 64-3
   64-2(0.80 g) was dissolved in EA (10 mL), m-CPBA (1.25 g) was added, the mixture was stirred overnight at room temperature, filtered, the filter cake was washed with EA, dried to get 0.70 g of white solid.
4. Synthesis of Compound 64-4
   64-3(0.70 g) was dissolved in DMF (10 mL), Methanesulfonyl chloride (0.38 mL) was added, and reacted at 80° C. for 3 h, the reaction mixture was poured into ice water, extracted three times with EA, the organic layers were combined, concentrated, purified by column chromatography (PE:EA=50:50) to give 0.60 g of white solid.
5. Synthesis of Compound 64-5
64-4(0.70 g), 2,4-difluorochlorobenzyl (0.70 g) and K₂CO₃(0.95 g) were dissolved in DMF, the mixture was reacted overnight at room temperature. The mixture was poured into water, extracted three times with EA, washed three times with saturated brine, dried over anhydrous sodium sulfate, concentrated. The crude product was purified by column chromatography (PE:EA=30:70) to give 0.65 g of yellow solid.
6. Synthesis of Compound 64-6
64-5(0.65 g) was placed in ammonia (10 mL), the mixture was reacted overnight at 150° C. Cooled, filtered with suction, the filter cake was washed with water, the solid was dried in vacuo to give a white solid 0.50 g.
7. Synthesis of Compound 64-7
Compound 64-6(0.50 g), TEA (0.49 g) was dissolved in DCM (10 mL), ethylsulfonyl chloride (0.42 g) was added, the mixture was reacted at room temperature for 2 h. The reaction mixture was poured into water, extracted three times with DCM, the organic layers were combined, washed with saturated brine, dried over anhydrous sodium sulfate, and concentrated. The crude product was purified by column chromatography (PE:EA=30:70) to give 0.40 g of white solid.
8. Synthesis of Compound 64
Compound 64-7(0.40 g), 58-2(0.27 g), K₂CO₃(0.41 g), Xphos-Pd-G2(0.08 g) were added in dioxane and water, reacted at 80° C. for 4 h. The reaction mixture was cooled, poured into water, extracted three times with EA, the organic layers were combined, washed three times with saturated brine, dried over anhydrous sodium sulfate, and concentrated. The crude product was purified by column chromatography (MeOH:DCM=10:90) to give 0.1 g of gray solid. LCMS: [M+1]+=513.1.
1H NMR (400 MHz, DMSO) δ 12.12 (d, J=17.8 Hz, 1H), 8.46 (s, 1H), 7.64-7.59 (m, 1H), 7.55-7.42 (m, 1H), 7.39 (t, J=2.8 Hz, 1H), 7.36-6.97 (m, 3H), 6.80-6.74 (m, 1H), 5.56 (s, 2H), 3.76-3.51 (m, 5H), 2.62 (s, 3H), 1.38-1.25 (m, 3H).

Using a method basically similar to that of Example 58, 59 and 64, for example, using corresponding intermediates and raw materials, for example, use

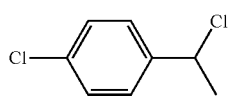

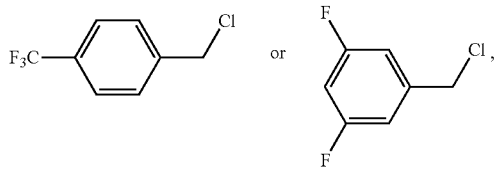 [SMILES: FC(F)(F)c1ccc(CCl)cc1 ; Fc1cc(F)cc(CCl)c1]

to prepare the compounds described in Table 7 below.

TABLE 7

| Example | Structure | Chemical Name | Physical data (MS) (M + H)+ |
|---|---|---|---|
| 58 | 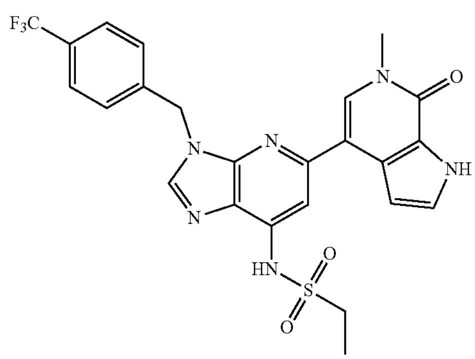 [SMILES: CCS(=O)(=O)Nc1cc(-c2cn(C)c(=O)c3[nH]ccc23)nc2c1ncn2Cc1ccc(C(F)(F)F)cc1] | N-(5-(6-methyl-7-oxo-6,7-dihydro-1H-pyrrolo[2,3-c]pyridin-4-yl)-3-(4-(trifluoromethyl)benzyl)-3H-imidazo[4,5-b]pyridin-7-yl)ethanesulfonamide | 531.1 |
| 59 | 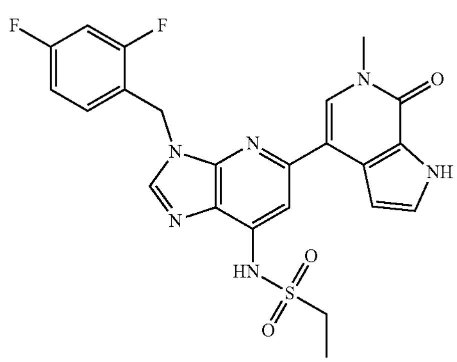 [SMILES: CCS(=O)(=O)Nc1cc(-c2cn(C)c(=O)c3[nH]ccc23)nc2c1ncn2Cc1ccc(F)cc1F] | N-(3-(2,4-difluorobenzyl)-5-(6-methyl-7-oxo-6,7-dihydro-1H-pyrrolo[2,3-c]pyridin-4-yl)-3H-imidazo[4,5-b]pyridin-7-yl)ethanesulfonamide | 499.1 |

TABLE 7-continued

| Example | Structure | Chemical Name | Physical data (MS) (M + H)+ |
|---|---|---|---|
| 60 | 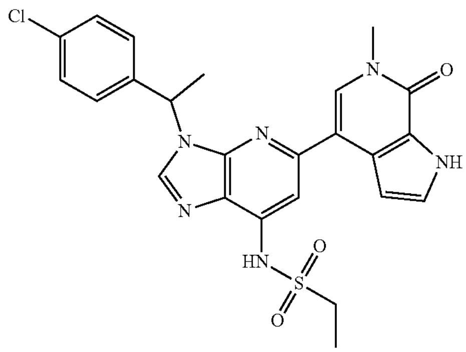 [SMILES: CCS(=O)(=O)Nc1cc(-c2cn(C)c(=O)c3[nH]ccc23)nc2c1ncn2C(C)c1ccc(Cl)cc1] | N-(3-(1-(4-chlorobenzyl)ethyl)-5-(6-methyl-7-oxo-6,7-dihydro-1H-pyrrolo[2,3-c]pyridin-4-yl)-3H-imidazo[4,5-b]pyridin-7-yl)ethanesulfonamide | 511.1 |
| 61 | 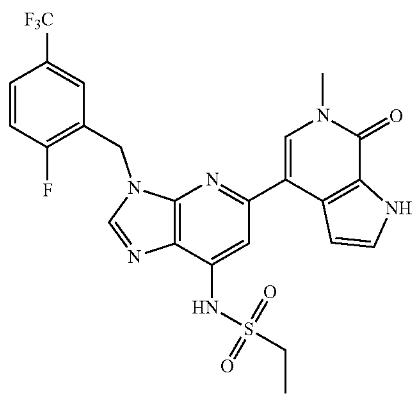 [SMILES: CCS(=O)(=O)Nc1cc(-c2cn(C)c(=O)c3[nH]ccc23)nc2c1ncn2Cc1cc(C(F)(F)F)ccc1F] | N-(3-(2-fluoro-5-(trifluoromethyl)benzyl)-5-(6-methyl-7-oxo-6,7-dihydro-1H-pyrrolo[2,3-c]pyridin-4-yl)-3H-imidazo[4,5-b]pyridin-7-yl)ethanesulfonamide | 549.1 |
| 62 | 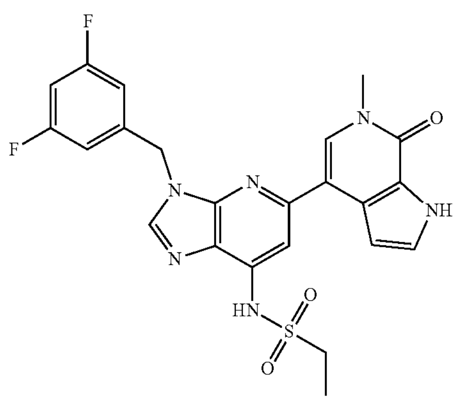 [SMILES: CCS(=O)(=O)Nc1cc(-c2cn(C)c(=O)c3[nH]ccc23)nc2c1ncn2Cc1cc(F)cc(F)c1] | N-(3-(3,5-difluorobenzyl)-5-(6-methyl-7-oxo-6,7-dihydro-1H-pyrrolo[2,3-c]pyridin-4-yl)-3H-imidazo[4,5-b]pyridin-7-yl)ethanesulfonamide | 499.1 |
| 63 | 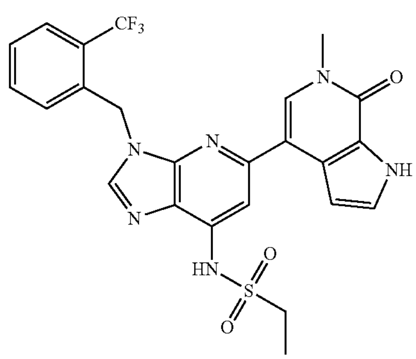 [SMILES: CCS(=O)(=O)Nc1cc(-c2cn(C)c(=O)c3[nH]ccc23)nc2c1ncn2Cc1ccccc1C(F)(F)F] | N-(5-(6-methyl-7-oxo-6,7-dihydro-1H-pyrrolo[2,3-c]pyridin-4-yl)-3-(2-(trifluoromethyl)benzyl)-3H-imidazo[4,5-b]pyridin-7-yl)ethanesulfonamide | 531.1 |

TABLE 7-continued

| Example | Structure | Chemical Name | Physical data (MS) (M + H)+ |
|---|---|---|---|
| 64 | 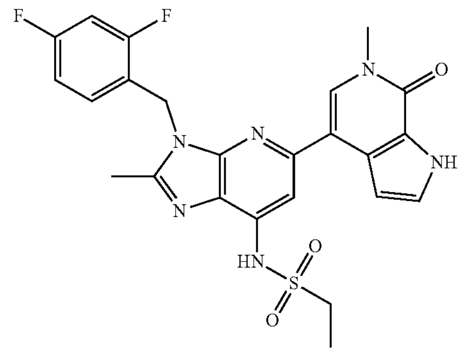 [SMILES: CCS(=O)(=O)Nc1cc(-c2cn(C)c(=O)c3[nH]ccc23)nc2c1nc(C)n2Cc1ccc(F)cc1F] | N-(3-(2,4-difluorobenzyl)-2-methyl-5-(6-methyl-7-oxo-6,7-dihydro-1H-pyrrolo[2,3-c]pyridin-4-yl)-3H-imidazo[4,5-b]pyridin-7-yl)ethanesulfonamide | 513.1 |
| 65 | 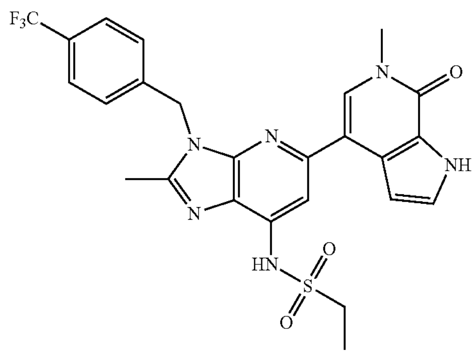 [SMILES: CCS(=O)(=O)Nc1cc(-c2cn(C)c(=O)c3[nH]ccc23)nc2c1nc(C)n2Cc1ccc(C(F)(F)F)cc1] | N-(2-methyl-5-(6-methyl-7-oxo-6,7-dihydro-1H-pyrrolo[2,3-c]pyridin-4-yl)-3-(4-(trifluoromethyl)benzyl)-3H-imidazo[4,5-b]pyridin-7-yl)ethanesulfonamide | 545.2 |
| 66 | 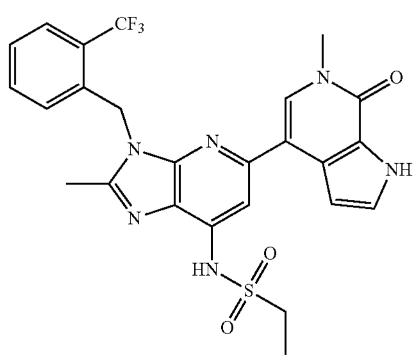 [SMILES: CCS(=O)(=O)Nc1cc(-c2cn(C)c(=O)c3[nH]ccc23)nc2c1nc(C)n2Cc1ccccc1C(F)(F)F] | N-(2-methyl-5-(6-methyl-7-oxo-6,7-dihydro-1H-pyrrolo[2,3-c]pyridin-4-yl)-3-(2-(trifluoromethyl)benzyl)-3H-imidazo[4,5-b]pyridin-7-yl)ethanesulfonamide | 545.2 |
| 67 | 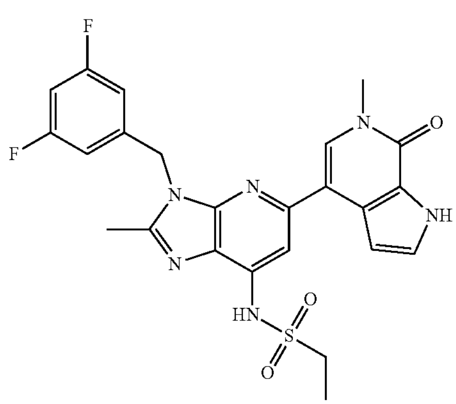 [SMILES: CCS(=O)(=O)Nc1cc(-c2cn(C)c(=O)c3[nH]ccc23)nc2c1nc(C)n2Cc1cc(F)cc(F)c1] | N-(3-(3,5-difluorobenzyl)-2-methyl-5-(6-methyl-7-oxo-6,7-dihydro-1H-pyrrolo[2,3-c]pyridin-4-yl)-3H-imidazo[4,5-b]pyridin-7-yl)ethanesulfonamide | 513.1 |

TABLE 7-continued

| Example | Structure | Chemical Name | Physical data (MS) (M + H)+ |
|---|---|---|---|
| 68 | 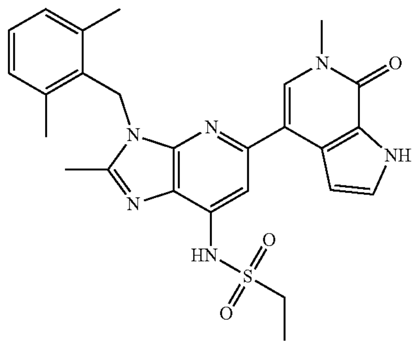 [SMILES: CCS(=O)(=O)Nc1cc(-c2cn(C)c(=O)c3[nH]ccc23)nc2c1nc(C)n2Cc1c(C)cccc1C] | N-(3-(2,6-dimethylbenzyl)-2-methyl-5-(6-methyl-7-oxo-6,7-dihydro-1H-pyrrolo[2,3-c]pyridin-4-yl)-3H-imidazo[4,5-b]pyridin-7-yl)ethanesulfonamide | 505.2 |

Example 69 Stability Test of Compound 19 Crystalline Form I

The X-ray powder diffraction pattern detection equipment and method of the present invention are shown in Table 2.

Crystalline Form I of compound 19 was dried and placed at 80° C. for 24 hours, or 25° C.-60% RH for 10 days, or 40° C.-75% RH for 14 days, the crystal form showed no solid form change under such stability conditions.

Figure 3:
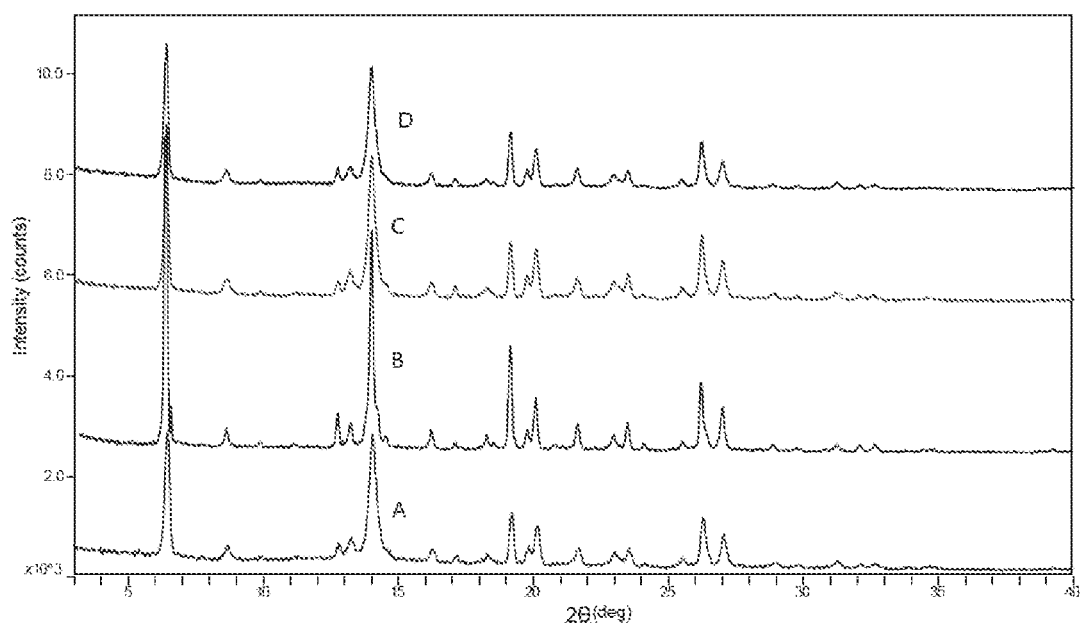
FIG. 3: XRD comparison pattern for crystalline form I of Compound 19 under different stability conditions. In the figure, A is the XRD pattern of crystalline form I at day 0; B is the XRD pattern of crystalline form I dried at 80° C. for 24 hours; C is the XRD pattern of crystalline form I placed at 25° C.-60% RH for 10 days; D is the XRD pattern of crystalline form I placed at 40° C.-75% RH for 14 days.

The XRD comparison of Compound 19 Crystal Form I under different stability conditions is shown in FIG. 3, which shows that the Compound 19 Crystalline Form I has a good stability.

Example 70 Dynamic Vapor Sorption (DVS) Test

The dynamic vapor sorption instrument and method of the present invention are shown in Table 3.

Crystalline Form A of compound II: The weight change is about 0.1% under 0% RH-80% RH condition, not hygroscopic, suitable for the preparation of solid formulations.

Comparison Example 1

Comparison example 1-1

Comparison example 2-2

Comparison example 1-3

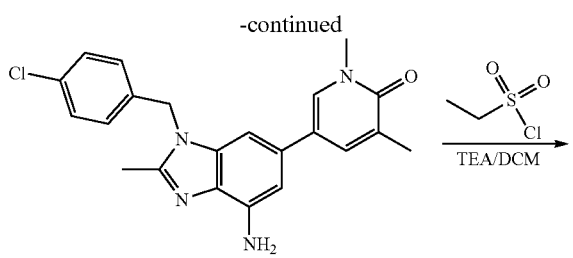

Comparison example 1-4

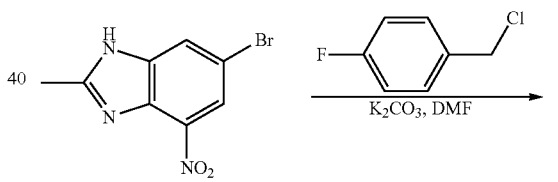

Comparison example 1

Synthesis of Compound 1-M1

A mixture of 5-bromo-1,3-dimethyl-2-pyridone (0.50 g), bis(pinacolato)diboron (1.27 g), Pd(dppf)Cl$_2$.DCM (0.20 g), potassium acetate (0.73 g), 1,4-dioxane (8 mL) was reacted at 90° C. for 3 h under N$_2$ protect. The reaction mixture was poured into the mixture of EA (50 mL) and Saturated ammonium chloride solution (50 mL), the organic layer was separated, the water layer was extracted three times with EA, the organic layers were combined, washed three times with saturated brine, dried over anhydrous sodium sulfate, concentrated, purified by column chromatography (PE:EA=100:20) to obtain an off-white solid, which was compound 1-M1, 0.67 g.

Synthesis of Comparison Example 1-1

A mixture of 5-bromo-3-nitrophenyl-1,2-diamine (1.00 g), acetylacetone (0.86 g), ethanol 20 mL, hydrochloric acid (6 mL, 5 mol/L) was stirred at 100° C. for 4 h, cooled to room temperature, concentrated, purified by column chromatography (PE:EA=100:30-100:45) to obtain an yellow solid, which was comparison example 1-1, 0.90 g.

Synthesis of Comparison Example 1-2

A mixture of comparison example 1-1(0.85 g), P-chlorobenzyl chloride (0.70 g), potassium carbonate (0.92 g), acetonitrile 20 mL, DMF (4 mL) was reacted overnight at 60° C. Cooled, poured into saturated Sodium chloride solution (100 mL), separated, the aqueous phase was extracted three times with EA, the organic phases were combined, washed three times with saturated brine, dried over anhydrous sodium sulfate, concentrate, purified by column chromatography (PE:EA=100:30-100:50) to obtain a yellow solid, which was comparison example 0.40 g.

Synthesis of Comparison Example 1-3

A mixture of comparison example 1-2(0.45 g), compound 1-M1(0.29 g), Pd(dppf)Cl$_2$.DCM (0.10 g), anhydrous potassium carbonate (0.24 g), 1,4-dioxane (10 mL) and water (2 mL) was stirred overnight at 90° C. Cooled, poured into a mixture of EA (50 mL) and saturated ammonium chloride solution (50 mL), separated and the organic layer was collected, the aqueous phase was extracted three times by EA, the organic phases were combined, washed with three times saturated brine, dried over anhydrous sodium sulfate, concentrated, purified by column chromatography with DCM:MeOH=100:3 to obtain a brown solid, which was comparison example 1-3(0.49 g).

Synthesis of Comparison Example 1-4

A mixture of comparison example 1-3(0.49 g), iron powder (0.33 g), ammonium chloride (0.13 g), THF (10 mL), ethanol (10 mL) and water (3 mL) was reacted overnight at 90° C. The mixture was filtered through celite, the filter cake was washed with methanol three times, the filtrate was concentrate, and the EA (50 mL) and saturated sodium carbonate solution (50 mL) were added, separated, the organic phase was collected, the aqueous phase was extracted three times by EA, the organic phases were combined, washed with three times saturated brine, dried over anhydrous sodium sulfate, concentrated, get a brown black solid, which was comparison example 1-4(0.30 g).

Synthesis of Comparison Compound 1

Comparison example 1-4(0.30 g) was dissolved in DCM (10 mL), added triethylamine (0.31 g) and ethylsulfonyl chloride (0.30 g), the mixture was stirred at room temperature for 2 h, concentrated. 1,4-dioxane (7.5 mL) and aqueous sodium hydroxide solution (10%, 2.5 mL) were added, stirred at 70° C. for 3 h, cooled, added saturated ammonium chloride solution (100 mL), extracted with EA 3 times, the organic phases were combined, washed with saturated brine 3 times, dried over anhydrous sodium sulfate, purified by column chromatography with DCM:MeOH=100:3 to obtain 0.08 g of a yellow solid, which was comparison example 1. LCMS: [M+1]+=485.1.

Comparison Example 2

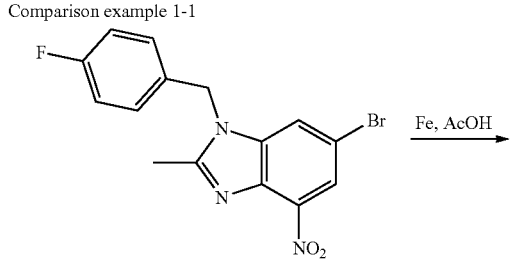

Comparison example 1-1

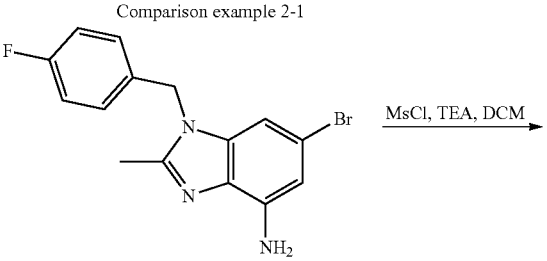

Comparison example 2-1

Comparison example 2-2

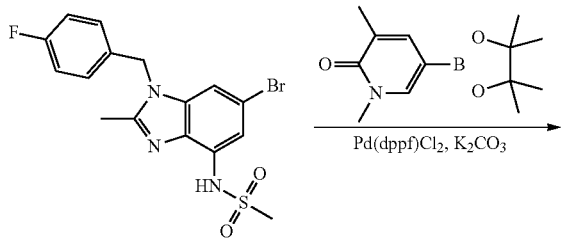

Comparison example 2-3

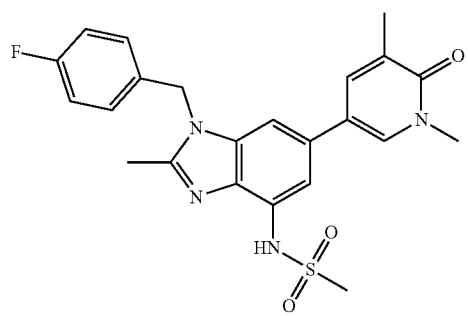

Comparison example 2

Synthesis of Comparison Example 2-1

Comparison example 1-1 (1.00 g) was dissolved in 15 ml DMF, Potassium carbonate (2.00 g), 4-fluorochlorobenzyl (0.67 g) were added, stirred overnight at room temperature, added 50 mL water, extracted with 50 ml EA three times, the organic phases were combined, concentrated, purified by crude column chromatography (PE:EA=50:50) to obtain a yellow solid, which was comparison example 2-1, 0.80 g.

Synthesis of Comparison Example 2-2

Comparison example 2-1 (0.80 g) was dissolved in 10 ml acetic acid, iron powder was added, reacted at 60° C. for 2 h, concentrated, added saturated sodium carbonate aqueous solution 100 mL, extracted with EA, concentrated, purified by crude column chromatography (PE:EA=20:80) to obtain a yellow solid, which was comparison example 2-2, 0.60 g.

Synthesis of Comparison Compound 2-3

Comparison example 2-2(0.60 g), triethylamine (0.55 g) was dissolved in 10 ml DCM, methanesulfonyl chloride was added dropwise, reacted at room temperature for 2 h. poured into water (50 mL), extracted with DCM (20 mL) three times, washed with saturated brine (20 mL) 3 times, dried over anhydrous sodium sulfate, concentrated. Purified by crude column chromatography with PE:EA=30:70 to obtain a yellow solid, which was comparison example 2-3, 0.50 g.

Synthesis of Comparison Compound 2

Added comparison example 2-3(0.41 g), 1-M1(0.25 g), $K_2C_3$(0.41 g), Pd(dppf)$Cl_2$(0.08 g) in dioxane 10 mL and water 2 mL, reacted at 80° C. for 4 h. Cooled, poured into 30 mL water, extracted with EA (30 mL) three times, the organic phases combined, washed with saturated brine, dried over anhydrous sodium sulfate, concentrated, and purified by crude column chromatography with MeOH:DCM=10:90 to obtain a grey solid, which was comparison example 2 2.40 mg.

LCMS: [M+1]+=455.1

Pharmacological Test

Example 1 the Inhibitory Activity of Compounds of the Invention Against BRD4(D1) and BRD4(D2) Test (IC50)

(+)-JQ1 was used as comparison compound, to evaluated the inhibitory activity of compounds of the invention against BRD4(D1) and BRD4(D2) in vitro.

The assays of BRD4 (D1) and BRD4 (D2) were conducted in a 384-well polystyrene plate. The test compounds were first serially diluted in DMSO and the test compound/DMSO were transferred to 384-well plates. The final concentration of DMSO in the assay was 0.1%. 2 volumes of protein/peptide mixture were added into 384-well plates, then 2 volumes of assay mixture were added, and shake for 30 s. The plate was incubated at room temperature for 2 h. Then the HTRF signal on EnVision was readed.

Use equation (1) to fit the date in Excel to obtain the value of the inhibition rate.

Inhibition rate (%)=(maximum value−signal value)/(maximum value−minimum value)*100   Equation(1):

IC50 determination was performed by fitting the data using GraphPad Prism 5.0 software and equation (2).

$Y$=bottom+(Top−bottom)/(1+10^((Log $IC_{50}$−X)*Hill-Slope));   Equation(2):

wherein, Y represents the percentage of inhibition (%); X represents the concentration of test compounds.

The $IC_{50}$ data of the examples were provided in the following table, wherein, A stands for $IC_{50}$<100 nM; B stands for $IC_{50}$ is 100-300 nM; C stands for $IC_{50}$>300 nM.

TABLE 8

| Example | BRD4(D1) $IC_{50}$(nM) | BRD4(D2) $IC_{50}$(nM) |
|---|---|---|
| (+)-JQ1 | 16 | 50 |
| 1 | 7.0 | 2.5 |
| 2 | 10.4 | 3.0 |
| 3 | 12.7 | 3.2 |
| 4 | 14.6 | 4.0 |
| 5 | 4.2 | 1.4 |
| 6 | 7.6 | 2.8 |
| 7 | 52.4 | 10.8 |
| 8 | 39.9 | 6.0 |
| 9 | B | B |
| 10 | C | C |
| 11 | C | B |
| 12 | B | B |
| 13 | B | B |
| 14 | B | C |
| 15 | C | B |
| 16 | B | A |
| 17 | C | C |
| 18 | 6.9 | 1.7 |
| 19 | 9.1 | 1.6 |
| 20 | 12.8 | 2.5 |
| 21 | 6.1 | 1.8 |
| 22 | A | A |
| 23 | A | A |
| 24 | A | A |
| 25 | A | A |
| 26 | A | A |
| 27 | A | A |
| 28 | A | A |
| 29 | A | A |
| 30 | A | A |
| 31 | A | A |
| 32 | A | A |
| 33 | A | A |
| 34 | 106.6 | 31.0 |
| 35 | 45.1 | 5.3 |
| 36 | 15.0 | 2.9 |
| 37 | C | C |

TABLE 8-continued

| Example | BRD4(D1) IC$_{50}$(nM) | BRD4(D2) IC$_{50}$(nM) |
|---|---|---|
| 38 | 7.3 | 2.2 |
| 39 | 21.2 | 7.9 |
| 40 | 10.5 | 2.5 |
| 41 | 1.0 | 0.4 |
| 42 | A | A |
| 43 | A | A |
| 44 | A | A |
| 45 | A | A |
| 46 | A | A |
| 47 | A | A |
| 48 | A | A |
| 49 | A | A |
| 50 | A | A |
| 51 | A | A |
| 52 | A | A |
| 53 | A | A |
| 54 | A | A |
| 55 | A | A |
| 56 | A | A |
| 57 | A | A |
| 58 | 1.6 | 0.5 |
| 59 | 1.2 | 0.5 |
| 60 | B | B |
| 61 | A | A |
| 62 | 1.3 | 1.2 |
| 63 | A | A |
| 64 | 1.1 | 0.5 |
| 65 | A | A |
| 66 | A | A |
| 67 | A | A |
| 68 | A | A |

Table 8 exemplarily lists the inhibitory ability of compounds of the invention against BRD4(D1) and BRD4(D2), it can be see that, the compound of the present invention exhibits equivalent, even stronger inhibition activity of BRD4 than positive comparison compound (+)-JQ1.

Example 2 Pharmacokinetic Assay

Male SD rats were offered by Beijing Vital River Laboratory Animal Technology Co., Ltd., the rats were divided into groups of 3, and the suspension of the test sample (5 mg/kg-20 mg/kg) was given by single gavage. The animals were fasted overnight before the experiment, the fasting time was from 10 hours before the administration to 4 hours after the administration. Blood was collected at 0.25, 0.5, 1, 2, 4, 7, and 24 hours after administration. Blood was collected from fundus venous plexus, and placed in EDTA-K2 anticoagulation tube. The sample was centrifuged at 4° C. and 4000 rpm for 10 min, the plasma was transferred into centrifuge tubes and the compound to be test was extracted by protein precipitation, the extract was analyzed by LC-MS/MS. Table 9 shows the PK data of the compound in rats.

TABLE 9

| compound | Oral dose (mg/kg) | T$_{1/2}$ (hr) | Cmax (ng/mL) | AUClast (h * ng/mL) |
|---|---|---|---|---|
| Comparison Example 1 | 10 | 8.8 | 140 | 526 |
| Comparison Example 2 | 10 | 3.7 | 206 | 592 |
| Example 18 | 10 | 3.4 | 224 | 2286 |
| Example 19 | 10 | 4.5 | 730 | 9433 |
| Example 23 | 10 | 3.3 | 407.3 | 2826 |
| Example 25 | 20 | 12.1 | 1230 | 13479 |
| Example 27 | 10 | 3.8 | 1003 | 8497 |
| Example 39 | 10 | 4.1 | 1700 | 23988 |

TABLE 9-continued

| compound | Oral dose (mg/kg) | T$_{1/2}$ (hr) | Cmax (ng/mL) | AUClast (h * ng/mL) |
|---|---|---|---|---|
| Example 58 | 10 | 2.3 | 1960 | 5097 |
| Example 59 | 5 | 2.3 | 3287 | 10241 |
| Example 64 | 6.7 | 3.5 | 1475 | 5586 |

The compound of the present invention is preferably a pharmaceutical composition having multiple modes of administration. Most preferably, the pharmaceutical composition is administered orally. This pharmaceutical composition and its preparation process are well known in the art, for example, REMINGTO: THE SCIENCE AND PRACTICE OF PHARMACY, A. Gennaro, et al., eds., 19$^{th}$ ed., Mack Publishing Co., 1995. The compound shown in formula (I) is effective in a relatively wide dose range.

For example, the normal daily dose range is usually about 1 mg to about 200 mg of the total daily dose (total daily dose), preferably, the total daily dose is from 1 mg to 150 mg, more preferably, the total daily dose is from 1 mg to 50 mg. In some cases, dose levels below the lower limit of the above range may be sufficient, while in other cases, large doses are still available. The above dosage range does not limit the protection scope of the present invention in any way. It is understandable that the actual dose of compound provided by the present invention will be decided by the doctor according to the relevant circumstances, including the treatment conditions, the choice of administration route, the compound and compound actually administered, age, weight, The reaction and the severity of the patient's symptoms.

The invention claimed is:
1. A compound of Formula (I), or a pharmaceutically acceptable salt thereof,

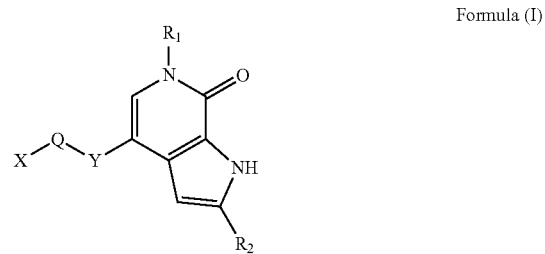

Formula (I)

wherein,
R$_1$ and R$_2$ are each independently selected from H, C$_{1-6}$ alkyl, C$_{1-6}$ alkoxy, C$_{6-10}$ aryl or C$_{5-10}$ heteroaryl, wherein the C$_{1-6}$ alkyl, C$_{1-6}$ alkoxy, C$_{6-10}$ aryl or C$_{5-10}$ heteroaryl is optionally substituted by C$_{1-6}$ alkyl, —NH$_2$, —OH, C$_{6-10}$ aryl or C$_{5-10}$ heteroaryl; and the C$_{5-10}$ heteroaryl has 1, 2, or 3 heteroatoms independently selected from nitrogen, oxygen or sulfur;
Q is absent or selected from C$_{1-6}$ alkylene, —SO$_2$— or —NH—, wherein the C$_{1-6}$ alkylene or —NH— is optionally substituted by halogen, C$_{1-6}$ alkyl or C$_{1-6}$ alkoxy;
X is selected from H, C$_{1-6}$ alkyl, C$_{6-10}$ aryl or C$_{5-10}$ heteroaryl, wherein the C$_{1-6}$ alkyl, C$_{6-10}$ aryl or C$_{5-10}$ heteroaryl is optionally substituted by halogen, halo C$_{1-6}$ alkyl, C$_{1-6}$ alkyl, C$_{1-6}$ alkoxy, C$_{1-6}$ alkylthio, C$_{1-6}$ alkoxycarbonyl or C$_{1-6}$ alkyl-SO$_2$—;

Y is selected from

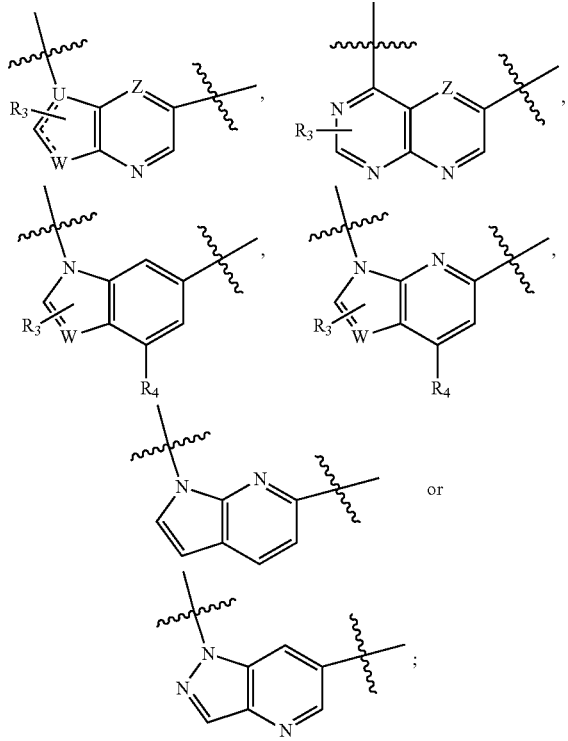

or

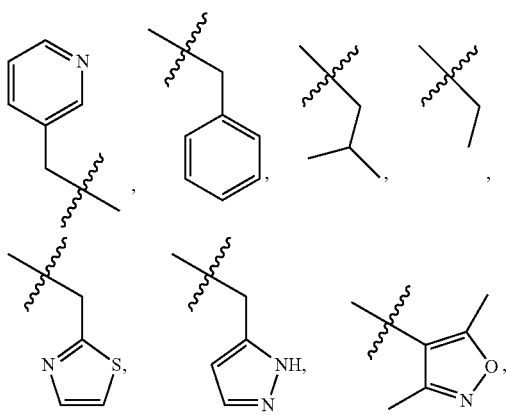

wherein, ⚌ represents a single bond or a double bond, the U, W or Z is independently selected from C or N; $R_3$ is selected from H, halogen, hydroxyl, amino, $C_{1-6}$ alkyl, $C_{1-6}$ alkoxy, cyano or oxo; $R_4$ is H or —N($R_5$)—$SO_2$—$R_6$; wherein $R_5$ and $R_6$ are each independently selected from H, $C_{1-6}$ alkyl or $C_{1-6}$ halogenoalkyl.

2. The compound according to claim 1, wherein $R_1$ is selected from H, $C_{1-4}$ alkyl, phenyl or $C_{5-6}$ heteroaryl, wherein the $C_{1-4}$ alkyl, phenyl or $C_{5-6}$ heteroaryl is optionally substituted by $C_{1-6}$ alkyl, —$NH_2$, phenyl, or $C_{5-6}$ heteroaryl.

3. The compound according to claim 1, wherein the heteroaryl has 1, 2 or 3 heteroatoms each independently selected from nitrogen or sulfur.

4. The compound according to claim 1, wherein $R_1$ is H, —$CH_3$,

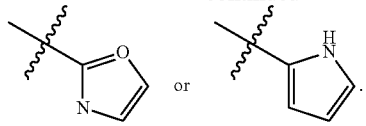

-continued

5. The compound according to claim 1, wherein $R_1$ is H, —$CH_3$,

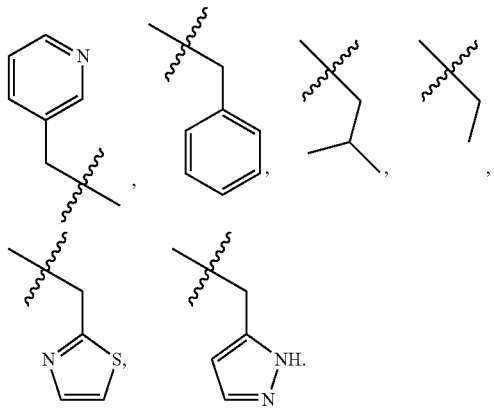

6. The compound according to claim 1, wherein $R_2$ is H or $C_{1-3}$ alkyl.

7. The compound according to claim 1, wherein $R_2$ is H or —$CH_3$.

8. The compound according to claim 1, wherein Q is absent or is selected from —$CH_2$—,

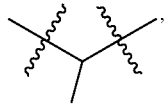 [SMILES: *C(*)C]

—NH— or —$SO_2$—.

9. The compound according to claim 1, wherein X is selected from H, $C_{1-3}$ alkyl or phenyl, wherein the phenyl is unsubstituted or optionally substituted by halogen, halo $C_{1-3}$ alkyl, $C_{1-3}$ alkyl, $C_{1-3}$ alkoxy, $C_{1-3}$ alkylthio, $C_{1-3}$ alkoxycarbonyl, or $C_{1-3}$ alkyl-$SO_2$—.

10. The compound according to claim 1, wherein X is selected from H, $C_{1-3}$ alkyl or phenyl, wherein the phenyl is unsubstituted or optionally substituted by F, Cl, methyl, trifluoromethyl, methoxy, methylthio, methoxycarbonyl or methyl-$SO_2$—.

11. The compound according to claim 1, wherein X is —$CH_3$, H,

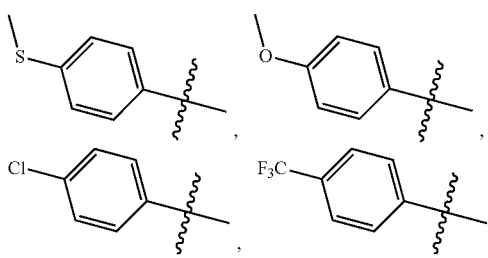

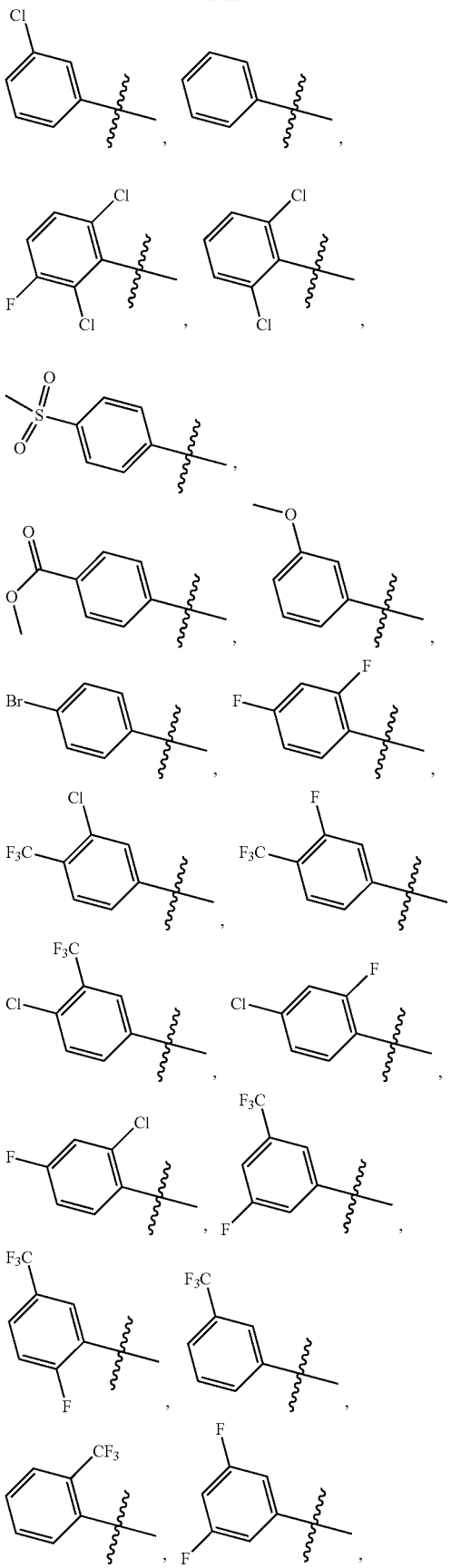
,

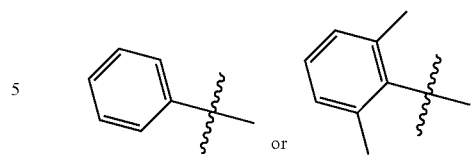
or

12. The compound according to claim 1, wherein $R_3$ is H, $C_{1-6}$ alkyl, $C_{1-6}$ alkoxy, cyano or oxo.

13. The compound of claim 1, wherein $R_3$ is H, methyl or oxo.

14. The compound of claim 1, wherein $R_4$ is —N($R_5$)—$SO_2$—$R_6$.

15. The compound of claim 1, wherein $R_5$ and $R_6$ are independently selected from H or $C_{1-6}$ alkyl.

16. The compound of claim 1, wherein $R_5$ and $R_6$ are independently selected from H, methyl or ethyl.

17. The compound of claim 1, wherein Y is

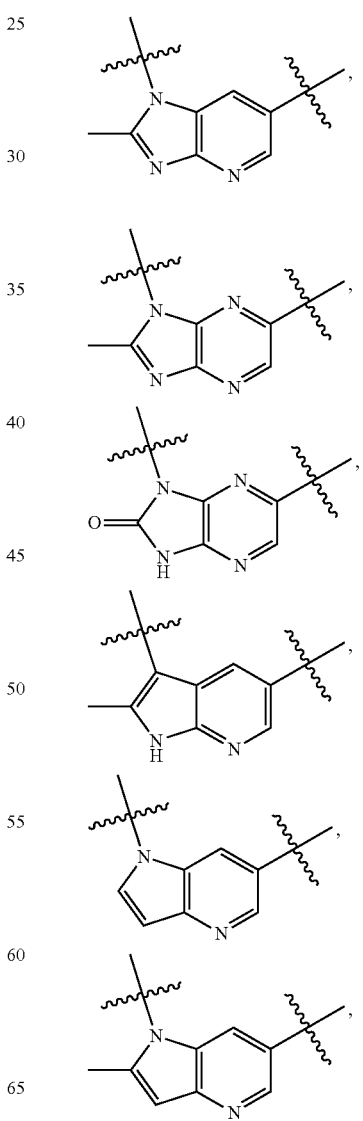

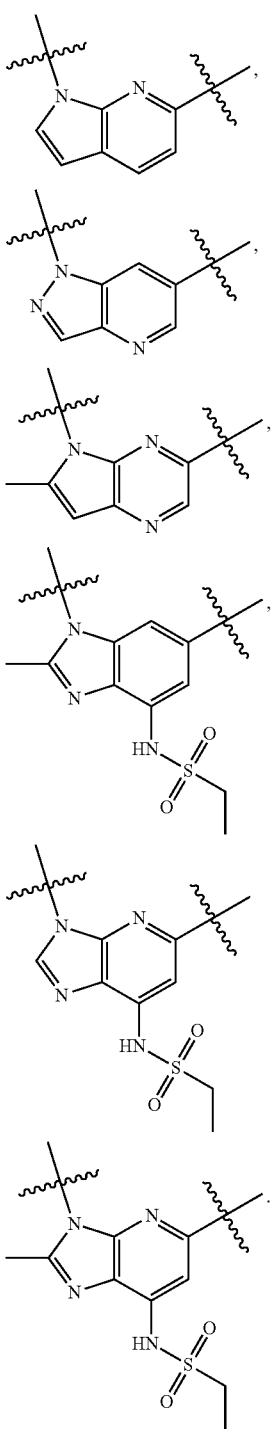

18. The compound of claim 1, wherein Y

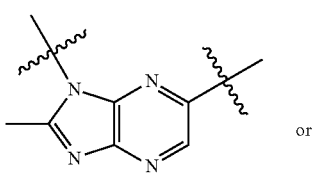 or

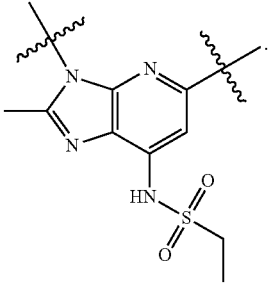

19. A compound or a pharmaceutically acceptable salt thereof, wherein the compound is:
1) 4-(1-(4-chlorobenzyl)-2-methyl-1H-imidazo[4,5-b]pyridin-6-yl)-6-methyl-1H-pyrrolo[2,3-c]pyridin-7(6H)-one;
2) 4-(1-(4-methoxybenzyl)-2-methyl-1H-imidazo[4,5-b]pyridin-6-yl)-6-methyl-1H-pyrrolo[2,3-c]pyridin-7(6H)-one;
3) 6-methyl-4-(2-methyl-1-(4-(methylthio)benzyl)-1H-imidazo[4,5-b]pyridin-6-yl)-1H-pyrrolo[2,3-c]pyridin-7(6H)-one;
4) 6-methyl-4-(2-methyl-1-(4-(trifluoromethyl)benzyl)-1H-imidazo[4,5-b]pyridin-6-yl)-1H-pyrrolo[2,3-c]pyridin-7(6H)-one;
5) 4-(1-(3-chlorobenzyl)-2-methyl-1H-imidazo[4,5-b]pyridin-6-yl)-6-methyl-1H-pyrrolo[2,3-c]pyridin-7(6H)-one;
6) 4-(1-benzyl-2-methyl-1H-imidazo[4,5-b]pyridin-6-yl)-6-methyl-1H-pyrrolo[2,3-c]pyridin-7(6H)one;
7) 4-(1,2-dimethyl-1H-imidazo[4,5-b]pyridin-6-yl)-6-methyl-1,6-dihydro-7H-pyrrolo[2,3-c]pyridin-7-one;
8) 6-methyl-4-(2-methyl-1H-imidazo[4,5-b]pyridin-6-yl)-1,6-dihydro-7H-pyrrolo[2,3-c]pyridin-7-one;
9) Methyl 4-((2-methyl-6-(6-methyl-7-oxo-6,7-dihydro-1H-pyrrolo[2,3-c]pyridin-4-yl)-1H-imidazo[4,5-b]pyridin-1-yl)methyl)benzoate;
10) 6-benzyl-4-(1-(4-methoxybenzyl)-2-methyl-1H-imidazo[4,5-b]pyridin-6-yl)-1,6-dihydro-7H-pyrrolo[2,3-c]pyridin-7-one;
11) 6-isobutyl-4-(1-(4-methoxybenzyl)-2-methyl-1H-imidazo[4,5-b]pyridin-6-yl)-1,6-dihydro-7H-pyrrolo[2,3-c]pyridin-7-one;
12) 6-ethyl-4-(1-(4-methoxybenzyl)-2-methyl-1H-imidazo[4,5-b]pyridin-6-yl)-1,6-dihydro-7H-pyrrolo[2,3-c]pyridin-7-one;
13) 4-(1-(4-methoxybenzyl)-2-methyl-1H-imidazo[4,5-b]pyridin-6-yl)-2-methyl-1,6-dihydro-7H-pyrrolo[2,3-c]pyridin-7-one;
14) 4-(1-(4-methoxybenzyl)-2-methyl-1H-imidazo[4,5-b]pyridin-6-yl)-6-(thiazol-2-methyl)-1,6-dihydro-7H-pyrrolo[2,3-c]pyridin-7-one;
15) 4-(1-(4-methoxybenzyl)-2-methyl-1H-imidazo[4,5-b]pyridin-6-yl)-6-(pyrazol-2-methyl)-1,6-dihydro-7H-pyrrolo[2,3-c]pyridin-7-one;
16) 4-(1-(3-methoxybenzyl)-2-methyl-1H-imidazo[4,5-b]pyridin-6-yl)-2-methyl-1,6-dihydro-7H-pyrrolo[2,3-c]pyridin-7-one;
17) 4-(1-(4-chlorobenzyl)-2-methyl-1H-imidazo[4,5-b]pyridin-6-yl)-6-(pyridin-3-methyl)-1,6-dihydro-7H-pyrrolo[2,3-c]pyridin-7-one;
18) 4-(1-(4-chlorobenzyl)-2-methyl-1H-imidazo[4,5-b]pyrazin-6-yl)-6-methyl-1H-pyrrolo[2,3-c]pyridin-7(6H)-one;

19) 6-methyl-4-(2-methyl-1-(4-(trifluoromethyl)benzyl)-1H-imidazo[4,5-b]pyrazin-6-yl)-1H-pyrrolo[2,3-c]pyridin-7(6H)-one;
20) 4-(1-(4-methoxybenzyl)-2-methyl-1H-imidazo[4,5-b]pyrazin-6-yl)-6-methyl-1H-pyrrolo[2,3-c]pyridin-7(6H)-one;
21) 4-(1-(1-(4-chlorophenyl)ethyl)-2-methyl-1H-imidazo[4,5-b]pyrazin-6-yl)-6-methyl-1,6-dihydro-7H-pyrrolo[2,3-c]pyridin-7-one;
22) 4-(1-benzyl-2-methyl-1H-imidazo[4,5-b]pyrazin-6-yl)-6-methyl-1H-pyrrolo[2,3-c]pyridin-7(6H)-one;
23) 4-(1-(3-trifluoromethylbenzyl)-2-methyl-1H-imidazo[4,5-b]pyrazin-6-yl)-6-methyl-1H-pyrrolo[2,3-c]pyridin-7(6H)-one;
24) 4-(1-(2-fluoro-5-trifluoromethylbenzyl)-2-methyl-1H-imidazo[4,5-b]pyrazin-6-yl)-6-methyl-1H-pyrrolo[2,3-c]pyridin-7(6H)-one;
25) 4-(1-(3-fluoro-5-trifluoromethylbenzyl)-2-methyl-1H-imidazo[4,5-b]pyrazin-6-yl)-6-methyl-1H-pyrrolo[2,3-c]pyridin-7(6H)-one;
26) 4-(1-(2-fluoro-4-chlorobenzyl)-2-methyl-1H-imidazo[4,5-b]pyrazin-6-yl)-6-methyl-1H-pyrrolo[2,3-c]pyridin-7(6H)-one;
27) 4-(1-(3-trifluoromethyl-4-chlorobenzyl)-2-methyl-1H-imidazo[4,5-b]pyrazin-6-yl)-6-methyl-1H-pyrrolo[2,3-c]pyridin-7(6H)-one;
28) 4-(1-(3-fluoro-4-trifluoromethylbenzyl)-2-methyl-1H-imidazo[4,5-b]pyrazin-6-yl)-6-methyl-1H-pyrrolo[2,3-c]pyridin-7(6H)-one;
29) 4-(1-(3-chloro-4-trifluoromethylbenzyl)-2-methyl-1H-imidazo[4,5-b]pyrazin-6-yl)-6-methyl-1H-pyrrolo[2,3-c]pyridin-7(6H)-one;
30) 4-(1-(3-chlorobenzyl)-2-methyl-1H-imidazo[4,5-b]pyrazin-6-yl)-6-methyl-1H-pyrrolo[2,3-c]pyridin-7(6H)-one;
31) 4-(1-(2,4-difluorobenzyl)-2-methyl-1H-imidazo[4,5-b]pyrazin-6-yl)-6-methyl-1H-pyrrolo[2,3-c]pyridin-7(6H)-one;
32) 4-(1-(4-bromobenzyl)-2-methyl-1H-imidazo[4,5-b]pyrazin-6-yl)-6-methyl-1H-pyrrolo[2,3-c]pyridin-7(6H)-one;
33) 6-methyl-4-(2-methyl-1-(4-(methylsulfonyl)benzyl)-1H-imidazo[4,5-b]pyrazin-6-yl)-1H-pyrrolo[2,3-c]pyridin-7(6H)-one;
34) 1-(4-chlorobenzyl)-6-(6-methyl-7-oxo-6,7-dihydro-1H-pyrrolo[2,3-c]pyridin-4-yl)-1,3-dihydro-2H-imidazo[4,5-b]pyridin-2-one;
35) 4-(3-(1-(2,6-dichloro-3-fluorophenyl)ethyl)-2-methyl-1H-pyrrolo[2,3-b]pyridin-5-yl)-6-methyl-1,6-dihydro-7H-pyrrolo[2,3-c]pyridin-7-one;
36) 4-(1-(2,6-dichlorobenzyl)-1H-pyrrolo[3,2-b]pyridin-6-yl)-6-methyl-1,6-dihydro-7H-pyrrolo[2,3-c]pyridin-7-one;
37) 4-(4-((4-chlorophenyl)amino)pyrido[2,3-d]pyrimidin-6-yl)-6-methyl-1,6-dihydro-7H-pyrrolo[2,3-c]pyridin-7-one;
38) 4-(1-(2,6-dichlorobenzyl)-2-methyl-1H-pyrrolo[3,2-b]pyridin-6-yl)-6-methyl-1,6-dihydro-7H-pyrrolo[2,3-c]pyridin-7-one;
39) 4-(1-(4-chlorobenzyl)-1H-pyrazolo[4,3-b]pyridin-6-yl)-6-methyl-1,6-dihydro-7H-pyrrolo[2,3-c]pyridin-7-one;
40) 4-(1-((4-chlorophenyl)sulfonyl)-1H-pyrrolo[2,3-b]pyridin-6-yl)-6-methyl-1,6-dihydro-7H-pyrrolo[2,3-c]pyridin-7-one;
41) N-(1-(4-chlorobenzyl)-2-methyl-6-(6-methyl-7-oxo-6,7-dihydro-1H-pyrrolo[2,3-c]pyridin-4-yl)-1H-benzo[d]imidazol-4-yl)ethanesulfonamide;
42) N-(2-methyl-6-(6-methyl-7-oxo-6,7-dihydro-1H-pyrrolo[2,3-c]pyridin-4-yl)-1-(4-(trifluoromethyl)benzyl)-1H-benzo[d]imidazol-4-yl)ethanesulfonamide;
43) N-(1-(4-methoxybenzyl)-2-methyl-6-(6-methyl-7-oxo-6,7-dihydro-1H-pyrrolo[2,3-c]pyridin-4-yl)-1H-benzo[d]imidazol-4-yl)ethanesulfonamide;
44) N-(1-(1-(4-chlorophenyl)ethyl)-2-methyl-6-(6-methyl-7-oxo-6,7-dihydro-1H-pyrrolo[2,3-c]pyridin-4-yl)-1H-benzo[d]imidazol-4-yl)ethanesulfonamide;
45) N-(1-benzyl-2-methyl-6-(6-methyl-7-oxo-6,7-dihydro-1H-pyrrolo[2,3-c]pyridin-4-yl)-1H-benzo[d]imidazol-4-yl)ethanesulfonamide;
46) N-(2-methyl-6-(6-methyl-7-oxo-6,7-dihydro-1H-pyrrolo[2,3-c]pyridin-4-yl)-1-(3-(trifluoromethyl)benzyl)-1H-benzo[d]imidazol-4-yl)ethanesulfonamide;
47) N-(2-methyl-6-(6-methyl-7-oxo-6,7-dihydro-1H-pyrrolo[2,3-c]pyridin-4-yl)-1-(2-fluoro-5-(trifluoromethyl)benzyl)-1H-benzo[d]imidazol-4-yl)ethanesulfonamide;
48) N-(2-methyl-6-(6-methyl-7-oxo-6,7-dihydro-1H-pyrrolo[2,3-c]pyridin-4-yl)-1-(3-fluoro-5-(trifluoromethyl)benzyl)-1H-benzo[d]imidazol-4-yl)ethanesulfonamide;
49) N-(2-methyl-6-(6-methyl-7-oxo-6,7-dihydro-1H-pyrrolo[2,3-c]pyridin-4-yl)-1-(2-fluoro-4-chlorobenzyl)-1H-benzo[d]imidazol-4-yl)ethanesulfonamide;
50) N-(2-methyl-6-(6-methyl-7-oxo-6,7-dihydro-1H-pyrrolo[2,3-c]pyridin-4-yl)-1-(3-(trifluoromethyl)-4chlorobenzyl)-1H-benzo[d]imidazol-4-yl)ethanesulfonamide;
51) N-(2-methyl-6-(6-methyl-7-oxo-6,7-dihydro-1H-pyrrolo[2,3-c]pyridin-4-yl)-1-(3-fluoro-4-(trifluoromethyl)benzyl)-1H-benzo[d]imidazol-4-yl)ethanesulfonamide;
52) N-(2-methyl-6-(6-methyl-7-oxo-6,7-dihydro-1H-pyrrolo[2,3-c]pyridin-4-yl)-1-(3-chloro-4-(trifluoromethyl)benzyl)-1H-benzo[d]imidazol-4-yl)ethanesulfonamide;
53) N-(2-methyl-6-(6-methyl-7-oxo-6,7-dihydro-1H-pyrrolo[2,3-c]pyridin-4-yl)-1-(3-chlorobenzyl)-1H-benzo[d]imidazol-4-yl)ethanesulfonamide;
54) N-(2-methyl-6-(6-methyl-7-oxo-6,7-dihydro-1H-pyrrolo[2,3-c]pyridin-4-yl)-1-(2,4-difluorobenzyl)-1H-benzo[d]imidazol-4-yl)ethanesulfonamide;
55) N-(2-methyl-6-(6-methyl-7-oxo-6,7-dihydro-1H-pyrrolo[2,3-c]pyridin-4-yl)-1-(4-bromobenzyl)-1H-benzo[d]imidazol-4-yl)ethanesulfonamide;
56) N-(2-methyl-6-(6-methyl-7-oxo-6,7-dihydro-1H-pyrrolo[2,3-c]pyridin-4-yl)-1-(4-(methylsulfonyl)benzyl)-1H-benzo[d]imidazol-4-yl)ethanesulfonamide;
57) N-(1-(2-chloro-4-fluorobenzyl)-2-methyl-6-(6-methyl-7-oxo-6,7-dihydro-1H-pyrrolo[2,3-c]pyridin-4-yl)-1H-benzo[d]imidazol-4-yl)ethanesulfonamide;
58) N-(5-(6-methyl-7-oxo-6,7-dihydro-1H-pyrrolo[2,3-c]pyridin-4-yl)-3-(4-(trifluoromethyl)benzyl)-3H-imidazo[4,5-b]pyridin-7-yl)ethanesulfonamide;
59) N-(3-(2,4-difluorobenzyl)-5-(6-methyl-7-oxo-6,7-dihydro-1H-pyrrolo[2,3-c]pyridin-4-yl)-3H-imidazo[4,5-b]pyridin-7-yl)ethanesulfonamide;
60) N-(3-(1-(4-chlorophenyl)ethyl)-5-(6-methyl-7-oxo-6,7-dihydro-1H-pyrrolo[2,3-c]pyridin-4-yl)-3H-imidazo[4,5-b]pyridin-7-yl)ethanesulfonamide;

61) N-(3-(2-fluoro-5-(trifluoromethyl)benzyl)-5-(6-methyl-7-oxo-6,7-dihydro-1H-pyrrolo[2,3-c]pyridin-4-yl)-3H-imidazo[4,5-b]pyridin-7-yl)ethanesulfonamide;

62) N-(3-(3,5-difluorobenzyl)-5-(6-methyl-7-oxo-6,7-dihydro-1H-pyrrolo[2,3-c]pyridin-4-yl)-3H-imidazo[4,5-b]pyridin-7-yl)ethanesulfonamide;

63) N-(5-(6-methyl-7-oxo-6,7-dihydro-1H-pyrrolo[2,3-c]pyridin-4-yl)-3-(2-(trifluoromethyl)benzyl)-3H-imidazo[4,5-b]pyridin-7-yl)ethanesulfonamide;

64) N-(3-(2,4-difluorobenzyl)-2-methyl-5-(6-methyl-7-oxo-6,7-dihydro-1H-pyrrolo[2,3-c]pyridin-4-yl)-3H-imidazo[4,5-b]pyridin-7-yl)ethanesulfonamide;

65) N-(2-methyl-5-(6-methyl-7-oxo-6,7-dihydro-1H-pyrrolo[2,3-c]pyridin-4-yl)-3-(4-(trifluoromethyl)benzyl)-3H-imidazo[4,5-b]pyridin-7-yl)ethanesulfonamide;

66) N-(2-methyl-5-(6-methyl-7-oxo-6,7-dihydro-1H-pyrrolo[2,3-c]pyridin-4-yl)-3-(2-(trifluoromethyl)benzyl)-3H-imidazo[4,5-b]pyridin-7-yl)ethanesulfonamide;

67) N-(3-(3,5-difluorobenzyl)-2-methyl-5-(6-methyl-7-oxo-6,7-dihydro-1H-pyrrolo[2,3-c]pyridin-4-yl)-3H-imidazo[4,5-b]pyridin-7-yl)ethanesulfonamide; or 68) N-(3-(2,6-dimethylbenzyl)-2-methyl-5-(6-methyl-7-oxo-6,7-dihydro-1H-pyrrolo[2,3-c]pyridin-4-yl)-3H-imidazo[4,5-b]pyridin-7-yl)ethanesulfonamide.

20. A method for treating a BET-mediated disease in a subject comprising administering to the subject the compound of claim 1, wherein the BET-mediated disease is selected from the group consisting of B acute lymphoblastic leukemia, Burkitt's lymphoma, diffuse large B-cell lymphoma, chronic lymphocytic leukemia, Hodgkin's lymphoma, follicular lymphoma, primary plasma cell leukemia, large cell neuroendocrine carcinoma, colon cancer, rectal cancer, mantle cell lymphoma, multiple myeloma, breast cancer, prostate cancer, glioblastoma tumor, squamous cell esophageal cancer, liposarcoma, melanoma, pancreatic cancer, brain cancer, and lung cancer.

21. The method according to claim 20, wherein the BET includes BRD4.

22. The method according to claim 20, wherein the subject is human.

* * * * *